(12) United States Patent
Leow et al.

(10) Patent No.: US 8,742,100 B2
(45) Date of Patent: Jun. 3, 2014

(54) SMALL MOLECULE INHIBITORS OF ISOPRENYLCYSTEINE CARBOXYL METHYLTRANSFERASE WITH POTENTIAL ANTICANCER ACTIVITY

(75) Inventors: Jo Lene Leow, Singapore (SG); Mei-Wang Casey, Singapore (SG); Patrick J. Casey, Singapore (SG); Mei Lin Go, Singapore (SG); Kumar Gorla Suresh, Waltham, MA (US)

(73) Assignee: National University of Singapore, Singapore (SG)

( * ) Notice: Subject to any disclaimer, the term of this patent is extended or adjusted under 35 U.S.C. 154(b) by 95 days.

(21) Appl. No.: 13/388,050

(22) PCT Filed: Jul. 30, 2010

(86) PCT No.: PCT/SG2010/000286
§ 371 (c)(1),
(2), (4) Date: Apr. 16, 2012

(87) PCT Pub. No.: WO2011/014128
PCT Pub. Date: Feb. 3, 2011

(65) Prior Publication Data
US 2012/0197014 A1     Aug. 2, 2012

(30) Foreign Application Priority Data

Jul. 30, 2009  (SG) ................................. 200905128
Nov. 20, 2009  (SG) ................................. 200907728

(51) Int. Cl.
C07D 209/14   (2006.01)
C07D 401/06   (2006.01)
C07D 403/06   (2006.01)
C07D 413/06   (2006.01)

(52) U.S. Cl.
CPC ............ *C07D 403/06* (2013.01); *C07D 413/06* (2013.01); *C07D 209/14* (2013.01); *C07D 401/06* (2013.01)
USPC ............ 544/143; 544/373; 546/201; 548/504

(58) Field of Classification Search
None
See application file for complete search history.

(56) References Cited

U.S. PATENT DOCUMENTS

2004/0138222 A1   7/2004  Stack et al.

FOREIGN PATENT DOCUMENTS

| CN | 1092765 A | 9/1994 |
|---|---|---|
| CN | 1729174 A | 2/2006 |
| CN | 101130515 A | 2/2008 |
| EP | 0 376 607 A1 | 7/1990 |
| EP | 2 141 163 A1 | 1/2010 |
| WO | WO 94/14771 A1 | 7/1994 |
| WO | WO 01/34146 A1 | 5/2001 |
| WO | WO 2004/056769 A2 | 7/2004 |
| WO | WO 2004/082586 A2 | 9/2004 |
| WO | WO 2006/058088 A2 | 6/2006 |
| WO | WO 2006/102126 A2 | 9/2006 |
| WO | WO 2008/100867 A2 | 8/2008 |
| WO | WO 2009/102805 A1 | 8/2009 |

OTHER PUBLICATIONS

Kilic et al., Synthesis and pp60c-Src Tyrosine Kinase Inhibitory Activities of Novel Indole-3-Imine and Amine Derivatives substituted at N1 and N5. Archiv der Pharmazie Chemistry in Life Science 2009, 342, 333-343.*

EPO Communication containing Extended European Search Report for European Patent Application No. 10804801.8, 16 pages, (Dec. 13, 2012).

Charles S. Sell, "Terpenoids", Kirk-Othmer Encyclopedia of Chemical Technology, vol. 24, John Wiley & Sons, Inc., pp. 1-143, (Sep. 15, 2006).

Jo-Lene Leow, et al., "Quantitative Structure-Activity Relationship (QSAR) of Indoloacetamides as Inhibitors of Human Isoprenylcysteine Carboxyl Methyltransferase", Bioorganic & Medicinal Chemistry Letters, vol. 17, pp. 1025-1032, (2007).

Zuhal Kilic, et al., "Synthesis and pp60$^{c-Src}$ Tyrosine Kinase Inhibitory Activities of Novel Indole-3-Imine and Amine Derivatives Substituted at N1 and C5", Arch. Pharm. Chem. Life Sci., vol. 342, pp. 333-343, (2009).

PCT International Search Report for PCT Counterpart Application No. PCT/SG2010/000286, 6 pgs., (Oct. 22, 2010).

PCT Written Opinion of the International Searching Authority for PCT Counterpart Application No. PCT/SG2010/000286, 9 pgs., (Oct. 22, 2010).

PCT International Preliminary Report on Patentability (Chapter II of the Patent Cooperation Treaty) for PCT Counterpart Application No. PCT/SG2010/000286, 23 pgs., (Aug. 26, 2011).

First Office Action for corresponding Chinese Patent Application No. 201080043545.0, 16 pages, (Apr. 27, 2013), (English translation only).

Ann M. Winter-Vann, et al., "Post-prenylation-processing enzymes as new targets in oncogenesis", Nature Reviews: Cancer, vol. 5, pp. 405-412, (May 2005).

Ann M. Winter-Vann, et al., "A small-molecule inhibitor of isoprenylcysteine carboxyl methyltransferase with antitumor activity in cancer cells", PNAS, vol. 102, No. 12, pp. 4336-4341, (Mar. 22, 2005).

(Continued)

*Primary Examiner* — Michael Barker
*Assistant Examiner* — Po-Chih Chen
(74) *Attorney, Agent, or Firm* — Blakely, Sokoloff, Taylor & Zafman LLP

(57) ABSTRACT

The present invention generally relates to inhibitors of isoprenylcysteine carboxyl methyltransferase (Icmt), in particularly to compounds that inhibit Icmt activity and pharmaceutical compositions thereof. The invention also relates to methods of disease treatment using the same.

13 Claims, 9 Drawing Sheets

(56) References Cited

OTHER PUBLICATIONS

Tony Magee, et al., "Fatty acylation and prenylation of proteins: what's hot in fat", Current Opinion in Cell Biology, vol. 17, pp. 190-196, (2005).

Patrick J. Casey, et al., "Protein Prenyltransferases", The Journal of Biological Chemistry, vol. 271, No. 10, pp. 5289-5292, (Mar. 8, 1996).

Steven Clarke, "Protein Isoprenylation and Methylation at Carboxyl-Terminal Cysteine Residues", Annu. Rev. Biochem., vol. 61, pp. 355-386, (1992).

Walter K. Schmidt, et al., "Endoplasmic reticulum membrane localization of Rce1p and Ste24p, yeast proteases involved in carboxyl-terminal CAAX protein processing and amino-terminal a-factor cleavage", Proc. Natl. Acad. Sci, USA, vol. 95, pp. 11175-11180. (Sep. 1998).

Steven Clarke, et al., "Posttranslational modification of the Ha-*ras* oncogene protein: Evidence for a third class of protein carboxyl methyltransferases", Proc. Natl. Acad. Sci. USA, vol. 85, pp. 4643-4647, (Jul. 1988).

Johannes L. Bos, "*ras* Oncogenes in Human Cancer: A Review", Cancer Research, vol. 49, pp. 4682-4689, (Sep. 1, 1989).

Marcos Malumbres, et al., "*RAS* oncogenes: the first 30 years", Nature Reviews: Cancer, vol. 3, pp. 7-13, (Jun. 2003).

Joseph Schlessinger, "Cell Signaling by Receptor Tyrosine Kinases", Cell, vol. 103, pp. 211-225, (Oct. 13, 2000).

Andreas Gschwind, et al., "The discovery of receptor tyrosine kinases: targets for cancer therapy", Nature Reviews: Cancer, vol. 4, pp. 361-370, (May 2004).

W. Robert Bishop, et al., "Farnesyl transferase inhibitors: Mechanism of Action, Translational Studies and Clinical Evaluation", Cancer Biology & Therapy, vol. 2, No. 4, Suppl. 1, pp. S96-S104, (Jul./Aug. 2003).

Saïd M. Sebti, "Protein farnesylation: Implications for normal physiology, malignant transformation, and cancer therapy", Cancer Cell, vol. 7, pp. 297-300, (Apr. 2005).

David B. Whyte, et al., "K- and N-Ras Are Geranylgeranylated in Cells Treated with Farnesyl Protein Transferase Inhibitors", The Journal of Biological Chemistry, vol. 272, No. 22, pp. 14459-14464, (May 30, 1997).

Matthew N. Ashby, "CaaX converting enzymes", Current Opinion in Lipidology, vol. 9, No. 2, pp. 99-102, (Apr. 1998).

Martin O. Bergo, et al., "Inactivation of *Icmt* inhibits transformation by oncogenic K-Ras and B-Raf", The Journal of Clinical Investigation, vol. 113, No. 4, pp. 539-550, (Feb. 2004).

Yi-Qun Shi, et al., "Kinetic Mechanism of Isoprenylated Protein Methyltransferase", The Journal of Biological Chemistry, vol. 267, No. 14, pp. 9547-9551, (May 15, 1992).

Ann M. Winter-Vann, et al., "Targeting Ras signaling through inhibition of carboxyl methylation: An unexpected property of methotrexate", PNAS, vol. 100, No. 11, pp. 6529-6534, (May 27, 2003).

Kristina Kramer, et al., "Isoprenylcysteine Carboxyl Methyltransferase Activity Modulates Endothelial Cell Apoptosis", Molecular Biology of the Cell, vol. 14, pp. 848-857, (Mar. 2003).

Dolores Perez-Sala, et al., "Prenylated protein methyltransferases do not distinguish between farnesylated and geranylgeranylated substrates", Biochem. J., vol. 284, pp. 835-840, (1992).

Rudi A. Baron, et al., "Time-Dependent Inhibition of Isoprenylcysteine Carboxyl Methyltransferase by Indole-Based Small Molecules", Biochemistry, vol. 46, No. 2, pp. 554-560, (2007).

Mei Wang, et al., "A Small Molecule Inhibitor of Isoprenylcysteine Carboxymethyltransferase Induces Autophagic Cell Death in PC3 Prostate Cancer Cells", The Journal of Biological Chemistry, vol. 283, No. 27, pp. 18678-18684, (Jul. 4, 2008).

Malcolm S, Buchanan, et al., "Spermatinamine, the first natural product inhibitor of isoprenylcysteine carboxyl methyltransferase, a new cancer target", Bioorganic & Medicinal Chemistry Letters, vol. 17, pp. 6860-6863, (2007).

Malcolm S. Buchanan, et al., "Small-molecule inhibitors of the cancer target, isoprenylcysteine carboxyl methyltransferase, from *Hovea parvicalyx*", Phytochemistry, vol. 69, pp. 1886-1889, (2008).

James L. Donelson, et al., "Amide-substituted farnesylcysteine analogs as inhibitors of human isoprenylcysteine carboxyl methyltransferase", Bioorganic & Medicinal Chemistry Letters, vol. 16, pp. 4420-4423, (2006).

Mei-Lin Go, et al., "Amino Derivatives of Indole As Potent Inhibitors of Isoprenylcysteine Carboxyl Methyltransferase", J. Med. Chem., vol. 53, pp. 6838-6850, (2010).

Fang L. Zhang, et al., "Protein Prenylation: Molecular Mechanisms and Functional Consequences", Annu. Rev. Biochem., vol. 65, pp. 241-269, (1996).

Yoel Kloog, et al., "Prenyl-binding domains: potential targets for Ras inhibitors and anti-cancer drugs", Seminars in Cancer Biology, vol. 14, pp. 253-261, (2004).

Victor L. Boyartchuk, et al., "Modulation of Ras and a-Factor Function by Carboxyl-Terminal Proteolysis", Science, vol. 275, pp. 1796-1800, (Mar. 21, 1997).

James C. Otto, et al., "Cloning and Characterization of a Mammalian Prenyl Protein-specific Protease", The Journal of Biological Chemistry, vol. 274, No. 13, pp. 8379-8382, (Mar. 26, 1999).

Christine A. Hrycyna, et al., "The *Saccharomyces cerevisiae STE14* gene encodes a methyltransferase that mediates C-terminal methylation of a-factor and RAS proteins", The EMBO Journal, vol. 10, No. 7, pp. 1699-1709, (1991).

Qun Dai, et al., "Mammalian Prenylcysteine Carboxyl Methyltransferase Is in the Endoplasmic Reticulum", The Journal of Biological Chemistry, vol. 273, No. 24, pp. 15030-15034, (Jun. 12, 1998).

John A. Glomset, et al., "Role of Protein Modification Reactions in Programming Interactions between Ras-Related Gtpases and Cell Membranes", Annu. Rev. Cell Biol., vol. 10, pp. 181-205, (1994).

Julian Downward, "Targeting Ras Signalling Pathways in Cancer Therapy", Nature Reviews: Cancer, vol. 3, pp. 11-22, (Jan. 2003).

Berthe M. Willumsen, et al., "The p21 *ras* C-terminus is required for transformation and membrane association", Nature, vol. 310, pp. 583-586, (Aug. 16, 1984).

Miguel C. Seabra, "Membrane Association and Targeting of Prenylated Ras-like GTPases", Cell. Signal., vol. 10, No. 3, pp. 167-172, (1998).

Jackson B. Gibbs, et al., "Farnesyttransferase Inhibitors: Ras Research Yields a Potential Cancer Therapeutic", Cell, vol. 77, pp. 175-179, (Apr. 22, 1994).

Julien Mazieres, et al., "Perspectives on farnesyl transferase inhibitors in cancer therapy", Cancer Letters, vol. 206, pp. 159-167, (2004).

S. R. D. Johnston, et al., "Farnesyl transferase inhibitors—a novel therapy for breast cancer", Endocrine-Related Cancer, vol. 8, pp. 227-235, (2001).

Cheryl A. Rowell, et al., "Direct Demonstration of Geranylgeranylation and Farnesylation of Ki-Ras in Vivo", The Journal of Biological Chemisty, vol. 272, No. 22, pp. 14093-14097, (May 30, 1997).

Annika M. Wahlstrom, et al., "Inactivating *Icmf* ameliorates K-RAS-induced myeloproliferative disease", Blood, vol. 112, No. 4, pp. 1357-1365, (Aug. 15, 2008).

Annika M, Wahlstrom, et al., "*Rce1* deficiency accelerates the development of K-RAS-induced myeloproliferative disease", Blood, vol. 109, No. 2, pp. 763-768, (Jan. 15, 2007).

M. Wang, et al., "Inhibition of isoprenylcysteine carboxylmethyltransferase induces autophagic-dependent apoptosis and impairs tumor growth", Oncogene, vol. 29, pp. 4959-4970, (2010).

Jessica L. Anderson, et al., "The Isoprenoid Substrate Specificity of Isoprenylcysteine Carboxylmethyltransferase", The Journal of Biological Chemistry, vol. 280, No. 33, pp. 29454-29461, (Aug. 19, 2005).

Brian S. Henriksen, et al., "Synthesis of desthio prenylcysteine analogs: Sulfur is important for biological activity", Bioorganic & Medicinal Chemistry Letters, vol. 15, pp. 5080-5083, (2005).

Malcolm S. Buchanan, et al., "Aplysamine 6, an Alkaloidal Inhibitor of Isoprenylcysteine Carboxyl Methyltransferase from the Sponge *Pseudoceratina* sp.", J. Nat. Prod., vol. 71, pp. 1066-1067, (2008).

(56) References Cited

OTHER PUBLICATIONS

Christopher A. Lipinski, et al., "Experimental and computational approaches to estimate solubility and permeability in drug discovery and development settings", Advanced Drug Delivery Reviews, vol. 23, pp. 3-25, (1997).

Daniel F. Veber, et al., "Molecular Properties That Influence the Oral Bioavailability of Drug Candidates", J. Med. Chem., vol. 45, pp. 2615-2623, (2002).

Edward H. Kerns, et al., "Chapter 7—Solubility", Drug-like Properties: Concepts, Structure Design and Methods, pp. 56-85, (2008).

Edward H. Kerns, et al., "Chapter 14—Plasma Protein Binding", Drug-like Properties: Concepts, Structure Design and Methods, pp. 187-196, (2008).

Young-Min Na, et al., "Synthesis and antifungal activity of new 1-halogenobenzyl-3-imidazolylmethylindole derivatives", European Journal of Medicinal Chemistry, vol. 38, pp. 75-87, (2003).

Warren J. Brehm, et al., "The Preparation of Mannich Bases Related to Gramine", J. Org. Chem., vol. 15, pp. 685-687, (1950).

Eliza N. Fung, et al., "Semi-automatic high-throughput determination of plasma protein binding using a 96-well plate filtrate assembly and fast liquid chromatography-tandem mass spectrometry", Journal of Chromatography B, vol. 795, pp. 187-194, (2003).

Mei Wang, et al., "A high-performance liquid chromatography method for the quantification of cysmethynil, an inhibitor of isoprenylcysteine carboxylmethyl transferase, in mouse plasma", Journal of Chromatography B, vol. 877, pp. 553-557, (2009).

Sudipta Roy, et al,, "Synthesis N-alkyl substituted bioactive indolocarbazoles related to Gö6976", Tetrahedron, vol. 62, pp. 7838-7845, (2006).

Aldo Andreani, et al., "N-Benzyl-2-chloroindole-3-carboxylic acids as potential anti-inflammatory agents. Synthesis and screening for the effects on human neutrophil functions and on COX1/COX2 activity", European Journal of Medicinal Chemistry, vol. 39, pp. 785-791, (2004).

Sophie-Isabelle Bascop, et al., "Synthesis of 2-aminopropyle-3-indole-acetic(propionic) acid derivatives", Arkivoc, pp. 46-61, (2003).

Jin-Sung Kim, et al., "Synthesis of desformylflustrabromine and its evaluation as an α4β2 and α7 nACh receptor modulator", Bioorganic & Medicinal Chemistry Letters, vol. 17, pp. 4855-4860, (2007).

M. S. C. Pedras, et al., "Brassinin oxidase, a fungal detoxifying enzyme to overcome a plant defense—purification, characterization and inhibition", FEBS Journal, vol. 275, pp. 3691-3705, (2008).

Norimichi Nakahata, et al., "Structure—activity relationship of gramine derivatives in $Ca^{2+}$ release from sarcoplasmic reticulum", European Journal of Pharmacology, vol. 382, pp. 129-132, (1999).

A. Sofia P. Cardoso, et al., "Studies in sigmatropic rearrangements of N-prenylindole derivatives—a formal enantiomerically pure synthesis of tryprostatin B", Org. Biomol. Chem., vol. 4, pp. 3966-3972, (2006).

CAplus Accession No. 1975:111898 of L. D. Basanagoudar, et al., "Synthesis of indole-3-propionic acids and 3-(3-aminopropyl) indoles", Journal of the Karnatak University, vol. 17, Abstract only, (1972).

CAplus Accession No. 1975:578700 of A. N. Kost, et al., "Indolylpropionic acid nitriles in the Ritter reaction", Vestnik Moskovskogo Universiteta, Seriya 2: Khimiya, vol. 16, Abstract only, (1975).

Cecilia Menciu, et al., "New N-(Pyridin-4-yl)-(indol-3-yl)acetamides and Propanamides as Antiallergic Agents", J. Med. Chem., vol. 42, pp. 638-648, (1999).

Delphine Carbonnelle, et al., "Synthetic N-pyridinyl(methyl)-indol-3-ylpropanamides as new potential immunosuppressive agents", European Journal of Medicinal Chemistry, vol. 42, pp. 686-693, (2007).

Wanguo Wei, et al., "New small molecule inhibitors of hepatitis C virus", Bioorganic & Medicinal Chemistry Letters, vol. 19, pp. 6926-6930, (2009).

Jo Lene Leow. "Design and Synthesis of Cysmethynil Analogues as Inhibitors of Isoprenylcysteine Carboxyl Methyltransferase (ICMT)", National University of Singapore—Department of Pharmacy, 220 pgs., Jul. 31, 2009.

* cited by examiner

Table 1: Series 1: Variation at $R_1$

| Code | $R_1$ | $R_2$ | $R_3$ | $IC_{50}$ for Icmt inhibition [1] µM | $IC_{50}$ for cell viability [2] (µM) | ClogP[3] |
|---|---|---|---|---|---|---|
| Cys | 3'-$CH_3$-$C_6H_5$ | -n-$C_8H_{17}$ | -$CH_2CONH_2$ | 1.5 | 21.8 | 7.00 |
| J23 | 2'-$CH_3$-$C_6H_5$ | -n-$C_8H_{17}$ | -$CH_2CONH_2$ | 1.0 | 20.1 | 6.25 |
| J24 | 4'-$CH_3$-$C_6H_5$ | -n-$C_8H_{17}$ | -$CH_2CONH_2$ | 1.4 | > 25 | 7.00 |
| J9 | 3'-$OCH_3$-$C_6H_5$ | -n-$C_8H_{17}$ | -$CH_2CONH_2$ | 1.9 | 22.9 | 6.42 |
| J8 | 3'-$OC_2H_5$-$C_6H_5$ | -n-$C_8H_{17}$ | -$CH_2CONH_2$ | 1.3 | 19.1 | 6.95 |
| J14 | $C_6H_5$ | -n-$C_8H_{17}$ | -$CH_2CONH_2$ | 1.8 | 25.3 | 6.5 |
| J15 | H | -n-$C_8H_{17}$ | -$CH_2CONH_2$ | 6.5 | >25 | 4.61 |

[1] Method is described in 6.1. Mean ±SD (n ≥ 3). If no SD is given, n = 2.
[2] Human breast cancer cells (MDA-MB231) were used, Method is described in Example 7
[3] Determined from Chem Draw Ultra 10.0

Figure 1

Table 2: Series 2: Variation at $R_2$

| Code | $R_1$ | $R_2$ | $R_3$ | IC$_{50}$ for Icmt inhibition [1] μM | IC$_{50}$ for cell viability [2] (μM) | ClogP[3] |
|---|---|---|---|---|---|---|
| Cys | 3'-CH$_3$-C$_6$H$_5$ | -n-C$_8$H$_{17}$ | -CH$_2$CONH$_2$ | 1.5 | 21.8 | 7.0 |
| J16 | 3'-CH$_3$-C$_6$H$_5$ | H | -CH$_2$CONH$_2$ | 33 | >100 | 2.83 |
| J10 | 3'-CH$_3$-C$_6$H$_5$ |  | -CH$_2$CONH$_2$ | 2.5 | 17.2 | 6.39 |
| J21 | 3'-CH$_3$-C$_6$H$_5$ | Isoprenyl | -CH$_2$CONH$_2$ | 7.7 | 28.5 | 5.00 |
| J22 | 3'-CH$_3$-C$_6$H$_5$ | geranyl | -CH$_2$CONH$_2$ | 1.1 | 10.6 | 7.03 |
| J11 | 3'-CH$_3$-C$_6$H$_5$ |  | CH$_2$CON(C$_2$H$_5$)$_2$ | 22.9 | >50 | 7.52 |

[1] Method is described in 6.1. Mean ± SD (n ≥ 3). If no SD is given, n = 2.
[2] Human breast cancer cells (MDA-MB 231) were used, Method is described in Example 7.
[3] Determined from Chem Draw Ultra 10.0

Figure 2

Table 3: Series 3: Variations at $R_3$ (tertiary amides)

| Code | $R_1$ | $R_2$ | $R_3$ | IC$_{50}$ for lcmt inhibition [1] μM | IC$_{50}$ for cell viability [2] (μM) | ClogP[3] |
|---|---|---|---|---|---|---|
| Cys | 3'-CH$_3$-C$_6$H$_5$ | -n-C$_8$H$_{17}$ | -CH$_2$CONH$_2$ | 1.5 | 21.8 | 7.0 |
| J5 | 3'-CH$_3$-C$_6$H$_5$ | -n-C$_8$H$_{17}$ | -CH$_2$CON(CH$_3$)$_2$ | 1.5 | 31.1 | 7.51 |
| J1 | 3'-CH$_3$-C$_6$H$_5$ | -n-C$_8$H$_{17}$ | -CH$_2$CON(C$_2$H$_5$)$_2$ | 1.4 | 27 | 8.57 |
| J7 | 3'-OCH$_3$C$_6$H$_5$ | -n-C$_8$H$_{17}$ | -CH$_2$CON(C$_2$H$_5$)$_2$ | 0.8 | 51.8 | 7.99 |
| J6 | 3'-OC$_2$H$_5$C$_6$H$_5$ | -n-C$_8$H$_{17}$ | -CH$_2$CON(C$_2$H$_5$)$_2$ | 1.0 | 26.8 | 8.52 |
| J4 | 3'-CH$_3$-C$_6$H$_5$ | -n-C$_8$H$_{17}$ | —CH$_2$C(=O)—N(pyrrolidine) | 1.2 | 15.6 | 9.71 |
| J2 | 3'-CH$_3$-C$_6$H$_5$ | -n-C$_8$H$_{17}$ | —CH$_2$C(=O)—N(piperidine) | 1.8 | 28.9 | 10.27 |
| J11 | 3'-CH$_3$-C$_6$H$_5$ | —CH$_2$-C$_6$H$_4$-CF$_3$ | -CH$_2$CON(C$_2$H$_5$)$_2$ | 22.9 | >50 | 7.52 |

[1] Method is described in 6.1. Mean ±SD (n ≥ 3). If no SD is given, n = 2.
[2] Human breast cancer cells (MDA-MB 231) were used, Method is described in Example 7
[3] Determined from Chem Draw Ultra 10.0

Figure 3

Table 4: Series 4: Variations at $R_3$ (other than tertiary amides)

| Code | $R_1$ | $R_2$ | $R_3$ | $IC_{50}$ for Icmt inhibition [1] μM | $IC_{50}$ for cell viability [2] (μM) | ClogP[3] |
|------|-------|-------|-------|------|------|------|
| Cys | 3'-CH$_3$-C$_6$H$_5$ | -n-C$_8$H$_{17}$ | -CH$_2$CONH$_2$ | 1.5 | 21.8 | 7.0 |
| J3 | 3'-CH$_3$-C$_6$H$_5$ | -n-C$_8$H$_{17}$ | -H | > 100 | > 50 | 8.69 |
| J20 | 3'-CH$_3$-C$_6$H$_5$ | -n-C$_8$H$_{17}$ | -CH$_2$CH2CONH$_2$ | 1.2 | 20.4 | 7.77 |
| J12 | 3'-CH$_3$-C$_6$H$_5$ | -n-C$_8$H$_{17}$ | -CH$_2$COOCH$_3$ | 76 | >100 | 8.37 |
| J13 | 3'-CH$_3$C$_6$H$_5$ | -n-C$_8$H$_{17}$ | -CH$_2$COOC$_2$H$_5$ | >100 | >100 | 8.90 |
| J19G | 3'-CH$_3$C$_6$H$_5$ | -n-C$_8$H$_{17}$ | -CH$_2$NHCOCH$_3$ | 1.8 | 30.4 | 7.50 |
| J28G | 3'-CH$_3$C$_6$H$_5$ | -n-C$_8$H$_{17}$ | -CH$_2$NH$_2$SO$_2$CH$_3$ | 1.2 | 17.1 | 7.36 |

[1] Method is described in 6.1. Mean ±SD (n ≥ 3). If no SD is given, n = 2.
[2] Human breast cancer cells (MDA-MB 231) were used. Method is described in Example 7
[3] Determined from Chem Draw Ultra 10.0

Figure 4

Table 5: Series 5: Variations at $R_3$ (amines)

| Code | $R_1$ | $R_2$ | $R_3$ | $IC_{50}$ for Icmt inhibition [1] (μM) | $IC_{50}$ for cell viability [2] (μM) | ClogP[3] |
|---|---|---|---|---|---|---|
| Cys | 3'-$CH_3$-$C_6H_5$ | -n-$C_8H_{17}$ | -$CH_2CONH_2$ | 1.5 | 21.8 | 7.0 |
| J18 | 3'-$CH_3$-$C_6H_5$ | -n-$C_8H_{17}$ | -$CH_2NH_2$ | 0.7 | 2.9 | 7.64 |
| J25G | 3'-$CH_3$-$C_6H_5$ | -n-$C_8H_{17}$ | -$CH_2N(CH_3)_2$ | 1.3 | 6.86 | 8.52 |
| J17G | 3'-$CH_3$-$C_6H_5$ | -n-$C_8H_{17}$ | -$CH_2N(C_2H_5)_2$ | 0.7 | 3.6 | 9.58 |
| J27G | 3'-$CH_3C_6H_5$ | -n-$C_8H_{17}$ | -$CH_2N(C_3H_7)_2$ | 0.8 | 13 | 10.64 |
| J26G | 3'-$CH_3C_6H_5$ | -n-$C_8H_{17}$ | 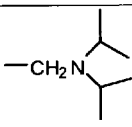 | 1.7 | 20.1 | 10.20 |
| J29G | 3'-$CH_3$-$C_6H_5$ | -n-$C_8H_{17}$ | 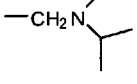 | 0.9 | 5.3 | 9.36 |
| J31G | 3'-$CH_3$-$C_6H_5$ | -n-$C_8H_{17}$ | 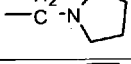 | 0.5 | 5.1 | 9.16 |
| J32G | 3'-$CH_3$-$C_6H_5$ | -n-$C_8H_{17}$ | 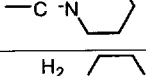 | 0.7 | 4.9 | 9.72 |
| J30G | 3'-$CH_3$-$C_6H_5$ | -n-$C_8H_{17}$ | 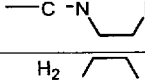 | 0.9 | 6.1 | 8.88 |
| J34G | 3'-$CH_3C_6H_5$ | -n-$C_8H_{17}$ | 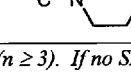 | 2.7 | 25 | 8.44 |

[1] Method is described in 6.1. Mean ± SD (n ≥ 3). If no SD is given, n = 2.
[2] Human breast cancer cells (MDA-MB 231) were used, Method is described in Example 7
[3] Determined from Chem Draw Ultra 10.0. As compounds are tertiary amines, a more useful gauge of lipophilicity would be log D (pH 7.4). This value would be lower than ClogP because the amino side chain will be protonated at pH 7.4.

Figure 5

Table 6: Series 6: Variations at $R_1$ and $R_2$, with $R_3$ = amino

| Code | $R_1$ | $R_2$ | $R_3$ | IC$_{50}$ for Icmt inhibition [1] ($\mu$M) | IC$_{50}$ for cell viability [2] ($\mu$M) | ClogP[3] |
|---|---|---|---|---|---|---|
| Cys | 3'-CH$_3$-C$_6$H$_5$ | -n-C$_8$H$_{17}$ | -CH$_2$CONH$_2$ | 1.5 | 21.8 | 7.0 |
| J17G | 3'-CH$_3$-C$_6$H$_5$ | -n-C$_8$H$_{17}$ | -CH$_2$N(C$_2$H$_5$)$_2$ | 0.7 | 3.6 | 9.58 |
| J36G | 2'-CH$_3$C$_6$H$_5$ | -n-C$_8$H$_{17}$ | -CH$_2$N(C$_2$H$_5$)$_2$ | 0.6 | 5.5 | 9.28 |
| J37G | 4'-CH$_3$C$_6$H$_5$ | -n-C$_8$H$_{17}$ | -CH$_2$N(C$_2$H$_5$)$_2$ | 0.6 | 3.4 | 9.58 |
| J40G | F | -n-C$_8$H$_{17}$ | -CH$_2$N(C$_2$H$_5$)$_2$ | 4.1 | 7.2 | 7.38 |
| J38G | 3'-CH$_3$-C$_6$H$_5$ | isoprenyl | -CH$_2$N(C$_2$H$_5$)$_2$ | 2.4 | 3.8 | 7.58 |
| J39G | 3'-CH$_3$-C$_6$H$_5$ | isoprenyl | 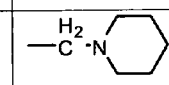 | 2.1 | 3.9 | 7.71 |
| J35G | H | isoprenyl | -CH$_2$N(C$_2$H$_5$)$_2$ | 67 | 74 | 5.19 |
| J41G | F | isoprenyl | -CH$_2$N(C$_2$H$_5$)$_2$ | 35 | 32 | 5.38 |

[1] Method is described in 6.1. Mean ± SD (n ≥ 3). If no SD is given, n = 2.
[2] Human breast cancer cells (MDA-MB 231) were used, Method is described in Example 7
[3] Determined from Chem Draw Ultra 10.0

Figure 6

SMALL MOLECULE INHIBITORS OF ISOPRENYLCYSTEINE CARBOXYL METHYLTRANSFERASE WITH POTENTIAL ANTICANCER ACTIVITY

CROSS-REFERENCE TO RELATED APPLICATIONS

This patent application is a U.S. National Phase application under 35 U.S.C. §371 of International Application No. PCT/SG2010/000286, filed 30 Jul. 2010, entitled SMALL MOLECULE INHIBITORS OF ISOPRENYLCYSTEINE CARBOXYL METHYLTRANSFERASE WITH POTENTIAL ANTICANCER ACTIVITY, which claims the benefit of priority of Singapore application number 200905128-5, filed 30 Jul. 2009, and Singapore application number 200907728-0, filed on 20 Nov. 2009, the content of both applications being hereby incorporated by reference in its entirety for all purposes.

FIELD OF THE INVENTION

The present invention relates to compounds having anti-cancer activity, in particularly to inhibitors of isoprenylcysteine carboxyl methyltransferase (Icmt), and methods of its use. The invention also provides a method of killing a cell using the compounds, to methods of diseases treatment and to pharmaceutical compositions of the compounds.

BACKGROUND OF THE INVENTION

Proteins with a CaaX motif regulate a number of pathways important in oncogenesis. These proteins undergo a series of post-translational modifications that are important for their localization, stability and function. The modifications are initiated by the addition of an isoprenoid moiety (farnesyl or geranylgeranyl) to the cysteine of the CaaX motif by protein farnesyltransferase (FTase) or protein geranylgeranyltransferase-1 (GGTase-1) respectively. This is followed by the endoproteolytic release of the terminal tripeptide (AAX) by RAS converting enzyme (RCE1) and carboxylmethylation of the C-terminal prenylcysteine by isoprenylcysteine carboxyl methyltransferase (Icmt).

The most widely studied example of CaaX proteins is the RAS family of regulatory proteins. RAS is a very important molecular switch for a variety of signaling pathways that control diverse processes like cytoskeletal integrity, proliferation, cell adhesion, apoptosis and cell migration. Activating mutations in RAS genes are implicated in the pathogenesis of a large number of solid tumors and hematologic malignancies. Many cancers contain alterations upstream of RAS in signaling cascades and the resultant hyperactivation of RAS is thought to contribute to tumorigenesis.

The possibility of blocking RAS-induced oncogenic transformation by inhibiting the enzymes involved in the post-translational processing of the CaaX motif has been explored for its therapeutic potential. The protein prenyltransferases in particular FTase have been targets of major drug discovery programs. FTase inhibitors showed significant activity in mouse models but clinical trials in cancer patients had been disappointing, possibly due to the geranylgeranylation of substrates by GGTase1 when FTase is inhibited. Hence, attention has been shifted to the post-prenylation enzymes RCE1 and Icmt as potential therapeutic targets. In particular, there is keen interest in developing Icmt inhibitors in view of studies that showed that genetic and pharmacological intervention with Icmt activity led to significant impairment of oncogenesis in several tumor cell models.

To date, three classes of Icmt inhibitors have been investigated. The first class comprises of S-adenosylhomocysteine (AdoHcy) and compounds that increase intracellular AdoHcy. AdoHcy is formed when a methyltransferase catalyzes the transfer of the methyl group from S-adenosylmethonine (AdoMet) to the substrate. AdoHcy binds to and competitively inhibits methyltransferase activity. However, AdoHcy is not a selective inhibitor of Icmt and affects the activity of other cellular methyltransferases. The second class of Icmt inhibitors is structural analogues of the substrate prenylcysteine. Examples are N-acetyl-S-farnesyl-L-cysteine (AFC) and N-acetyl-S-geranylgeranyl-L-cysteine (AGGC). These compounds are competitive inhibitors of Icmt but as structural mimics of the carboxy-terminal prenylcysteine of processed CaaX proteins, they would impact a large number of processes controlled by CaaX proteins.

Cysmethynil (2-[5-(3-methylphenyl)-1-octyl-1H-indolo-3-yl]acetamide) is a competitive inhibitor of the isopenylated cysteine substrate and a non-competitive inhibitor of the methyl donor AdoMet. Cysmethynil caused the mislocation of RAS and impaired epidermal growth factor signaling in cancer cells. It blocked anchorage-independent growth in a colon cancer cell line which was reversed by overexpression of Icmt. A recent report showed that induction of autophagy by cysmethynil is a major contributor to the cell death that accompanies pharmacological inhibition of Icmt.

Some natural products from marine sponges (spermatinamine, aplysamine 6) and plants (prenylated β hydroxychalcones, a flavanone S-glabrol) have been identified as Icmt inhibitors but they were either weakly potent inhibitors or lack drug-like features. Cysmethynil remains the most promising compound to date. However, cysmethynil has no dissociable functionalities and its high lipophilicity and poor aqueous solubility may potentially restrict its clinical application. Although modifications made at the N-substituent of the indole ring and the phenyl substituents of cysmethynil have been studied, the clinical relevance of these analogs is unknown.

Therefore, there remains a need to identify effective inhibitors of Icmt that can have potential therapeutic effects for treating cancer and diseases or disorders associated with Icmt activity.

It is a further object of the invention to provide a compound that can be a potent inhibitor of Icmt.

Another object of the invention is to provide a pharmaceutical composition that can have an anti-proliferative effect on cancer cells.

SUMMARY OF THE INVENTION

In one aspect, the invention provides a compound of formula I or a pharmaceutically acceptable salt thereof

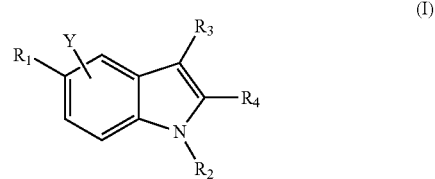

wherein
R₁ and Y are independently selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N═N, —N═O and $NX_1X_2$, wherein one or more of the hydrogen atoms of the indole ring can be replaced by Y;

R₂ is selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl and heteroalicyclyl;

R₃ is $(CH_2)_nNX_1X_2$, n being an integer from 1 to 4;

R₄ is hydrogen or $C_1$-$C_4$ alkyl;

X₁ and X₂ are independently selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, and heteroalicyclyl; or X₁ or X₂ may, together with the nitrogen atom bearing them, form a 3-8 membered ring, wherein the 3-8 membered ring is preferably a saturated ring, and wherein the 3-8 membered ring can be fused to at least one 3-8 membered ring, wherein the ring can optionally comprise 0, 1, 2, 3 or 4 further heteroatoms selected from the group consisting of oxygen, nitrogen, sulphur and phosphorus; and wherein the ring can be substituted by at least one substituent selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N═N, —N═O and $NX_1X_2$;

with the proviso that the following compounds are excluded:
3-(1-piperidinylmethyl)-1H-Indole-1-hexanamine;
1-(4-methyl-3-penten-1-yl)-N-(phenylmethyl)-1H-Indole-3-methanamine;
1-(3-buten-1-yl)-N-(phenylmethyl)-1H-Indole-3-methanamine;
5-ethenyl-N,N-dimethyl-1-h(phenylmethyl)-1H-Indole-3-methanamine, homopolymer (9CI);
N,1-dimethyl-N-(3-phenyl-2-propen-1-yl)-1H-Indole-3-methanamine;
N,1-dimethyl-N-(3-phenyl-2-propenyl)-1H-Indole-3-methanamine, (E)-(9CI);
3-[[4-(2,6-dimethylphenyl)-1-piperidinyl]methyl]-1-(phenylmethyl)-1H-Indole;
5-phenyl-3-(1-piperidinylmethyl)-1H-Indole;
1-methyl-3-(1-piperidinylmethyl)-5-[3-(1-piperidinyl)-1-propyn-1-yl]-1H-Indole;
1-(phenylmethyl)-3-(1-piperidinylmethyl)-1H-Indole, hydrochloride (1:1);
1-(phenylmethyl)-3-(1-piperidinylmethyl)-1H-Indole;
N,N-dimethyl-N-nonyl-1-(phenylmethyl)-1H-Indole-3-methanaminium;
N,N-dimethyl-N-octyl-1-(phenylmethyl)-1H-Indole-3-methanaminium;
N,N-dimethyl-N-[[1-(phenylmethyl)-1H-indol-3-yl]methyl]-1-heptanaminium;
N-(phenylmethyl)-1-(2-propen-1-yl)-N-(4-pyridinylmethyl)-1H-Indole-3-methanamine;
5-methyl-3-(1-piperidinylmethyl)-1-(2-propen-1-yl)-1H-Indole; and
N-ethyl-N-((5-fluoro-1-(3-methylbut-2-enyl)-1H-indol-3-yl)methyl)ethanamine.

In a second aspect, the invention provides a method of preparing a compound of formula I. The method includes adding a phosphine compound to a solution containing the compound of formula II

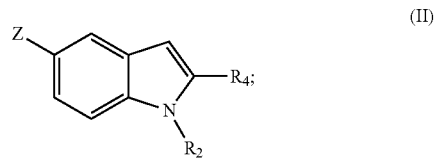

(II)

wherein Z is a leaving group, under conditions to form a compound of formula III

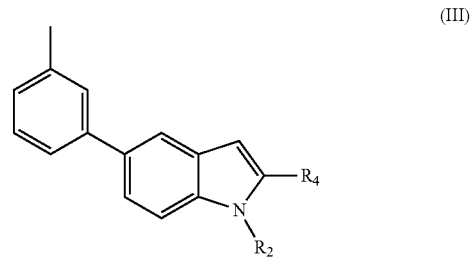

(III)

The method further includes adding an amine and an aldehyde to the solution obtained in the first step to form a compound of formula I.

In a third aspect, the invention provides a method of killing the cell. The method includes administering to the cell a compound of formula I as described above.

In a fourth aspect, the invention provides a pharmaceutical composition. The pharmaceutical composition includes the compound of formula I as described above.

In a fifth aspect, the invention provides a method of treating a mammal with a disease or disorder associated with Icmt activity. The method includes administering a compound of formula I or a pharmaceutical composition as described above.

In a sixth aspect, the invention provides a compound of Formula VII

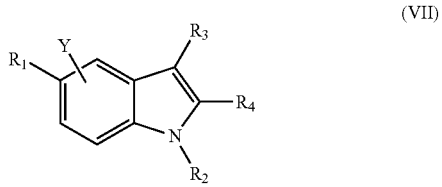

(VII)

or a pharmaceutically acceptable salt thereof,
wherein
R₁ and Y are independently selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N═N, —N═O and $NX_1X_2$, wherein one or more of the hydrogen atoms of the indole ring can be replaced by Y;

$R_2$ is a terpenoid;
$R_3$ is $(CH_2)_nCONX_1X_2$, n being an integer from 1 to 4; $R_4$ is hydrogen or $C_1$-$C_4$ alkyl;
$X_1$ and $X_2$ are independently selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, and heteroalicyclyl; or
$X_1$ or $X_2$ may, together with the nitrogen atom bearing them, form a 3-8 membered ring, wherein the 3-8 membered ring can be fused to at least one 3-8 membered ring, wherein the ring can optionally comprise 0, 1, 2, 3 or 4 further heteroatoms selected from the group consisting of oxygen, nitrogen, sulphur and phosphorus; and wherein the ring can be substituted by at least one substituent selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, perhaloalkyl, sulfonyl, sulfonamide, thio, —CN, —COOH, —SH, —N=N, —N=O and $NX_1X_2$.

In a seventh aspect, the invention provides a compound of Formula VIII

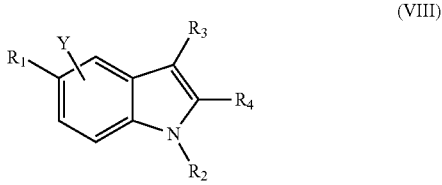

(VIII)

or a pharmaceutically acceptable salt thereof,
wherein
$R_1$ and Y are independently selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N=N, —N=O and $NX_1X_2$, wherein one or more of the hydrogen atoms of the indole ring can be replaced by Y;
$R_2$ is selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl and heteroalicyclyl;
$R_3$ is $(CH_2)_nCONX_1X_2$, n being an integer from 1 to 4; $R_4$ is hydrogen or $C_1$-$C_4$ alkyl;
wherein
$X_1$ and $X_2$ together with the nitrogen atom bearing them, form a 3-8 membered ring, wherein the 3-8 membered ring can be fused to at least one 3-8 membered ring, wherein the ring can optionally comprise 0, 1, 2, 3 or 4 further heteroatoms selected from the group consisting of oxygen, nitrogen, sulphur and phosphorus; and wherein the ring can be substituted by at least one substituent selected from the group consisting of hydrogen, hydroxyl, $C_{1-20}$allyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, perhaloalkyl, sulfonyl, sulfonamide, thio, —CN, —COOH, —SH, —N=N, —N=O and $NX_1X_2$.

In an eighth aspect, the invention provides a compound of Formula IX

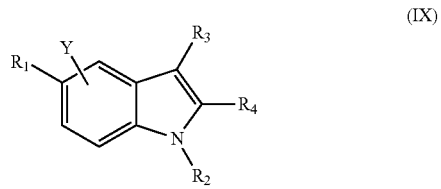

(IX)

or a pharmaceutically acceptable salt thereof,
wherein
$R_1$ and Y are independently selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N=N, —N=O and $NX_1X_2$, wherein one or more of the hydrogen atoms of the indole ring can be replaced by Y;
$R_2$ is selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl and heteroalicyclyl; and
$R_3$ is —$(CH_2)_2CONH_2$ or $CH_2NH_2SO_2CH_3$; $R_4$ is hydrogen or $C_1$-$C_4$ alkyl.

In a ninth aspect, the invention provides a compound of Formula X

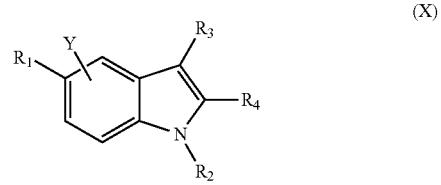

(X)

or a pharmaceutically acceptable salt thereof,
wherein
$R_1$ and Y are independently selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N=N, —N=O and $NX_1X_2$, wherein one or more of the hydrogen atoms of the indole ring can be replaced by Y;
$R_2$ is selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl and heteroalicyclyl; and
$R_3$ is $(CH_2)_nCONX_1X_2$, n being an integer from 1 to 4; $R_4$ is hydrogen or $C_1$-$C_4$ alkyl; wherein
$X_1$ is hydrogen and $X_2$ is one selected from the group consisting of $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, and heteroalicyclyl.

BRIEF DESCRIPTION OF THE DRAWINGS

The invention will be better understood with reference to the detailed description when considered in conjunction with the non-limiting examples and the accompanying drawings.

FIG. 1 shows Table 1 listing the compounds of Series 1 and their IC$_{50}$ values for Icmt inhibition and cell viability, in which the R$_1$ substituent is modified.

FIG. 2 shows Table 2 listing the compounds of Series 2 and their IC$_{50}$ values for Icmt inhibition and cell viability, in which the R$_2$ substituent is modified.

FIG. 3 shows Table 3 listing the compounds of Series 3 and their IC$_{50}$ values for Icmt inhibition and cell viability, in which the R$_3$ substituent is replaced by a tertiary amide side chain.

FIG. 4 shows Table 4 listing the compounds of Series 4 and their IC$_{50}$ values for Icmt inhibition and cell viability, in which the R$_3$ substituent is replaced by a substituent other than tertiary amides.

FIG. 5 shows Table 5 listing the compounds of Series 5 and their IC$_{50}$ values for Icmt inhibition and cell viability, in which the R$_1$ substituent is replaced by an amine side chain.

FIG. 6 shows Table 6 listing the compounds of Series 6 and their IC$_{50}$ values for Icmt inhibition and cell viability, in which the R$_3$ substituent is replaced with an amine side chain along with a modification of the R$_2$ substituent.

DETAILED DESCRIPTION OF THE INVENTION

Figure 7:
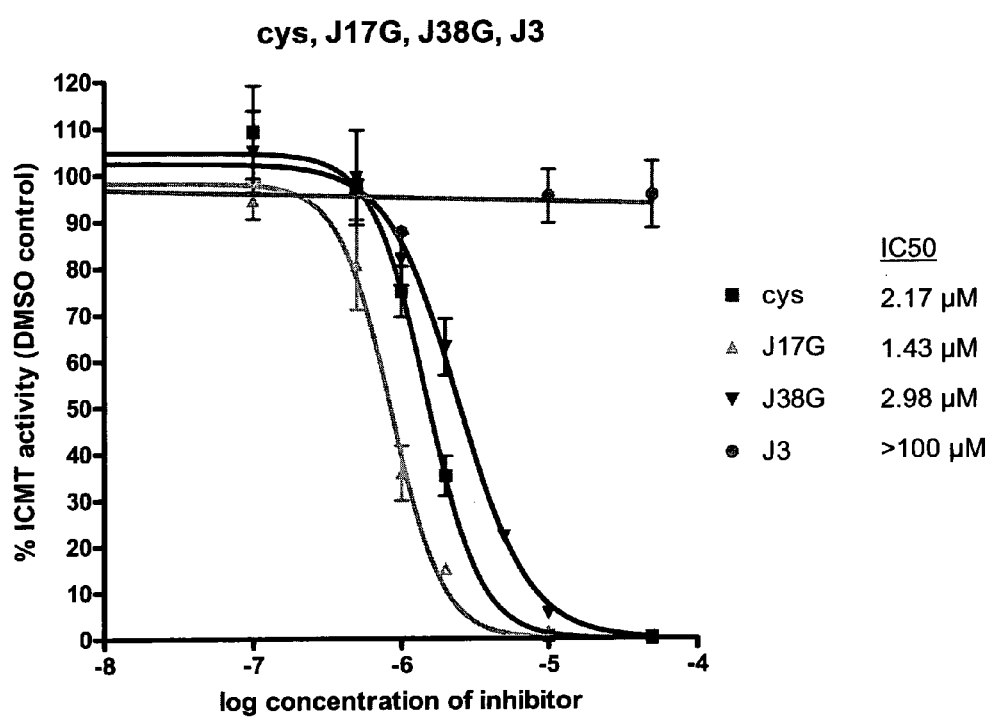
FIG. 7 depicts the Icmt inhibition activity of cysmethynil (cys), compound J17G (taken from Table 5); compound J38G (taken from Table 6); and compound J3 (taken from Table 4).
Figure 8:
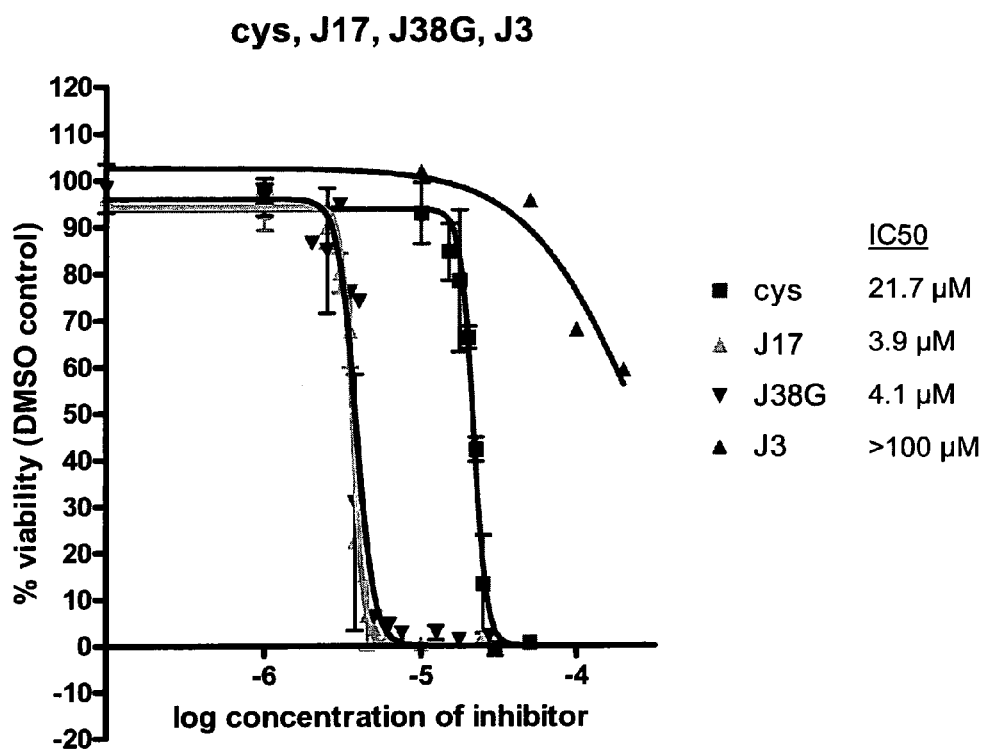
FIG. 8 depicts the anti-proliferative activity of cysmethynil (cys), compound J17G (taken from Table 5); compound J38G (taken from Table 6); and compound J3 (taken from Table 4).

The present invention is based on the finding that the compounds of the present invention described herein can retain or improve on biological profiles as compared to cysmethynil, while maintaining a more favourable drug-like profile, in terms of lower lipophilicities for example. In general, the compounds described herein have enhanced Icmt inhibition activity and more potent anti-proliferative activities in cancer cells for example. Such anti-proliferative effect can be seen in breast cancer cells for example, as shown in Example 7, FIGS. 1 and 2. Accordingly, the present invention provides a compound of Formula I or a pharmaceutically acceptable salt thereof:

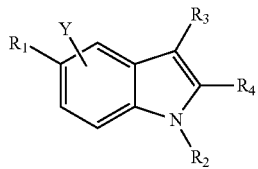
(I)

In the compound of Formula I, R$_1$ and Y are independently selected from the group consisting of hydrogen, hydroxyl, C$_{1-20}$alkyl, C$_{2-20}$alkenyl, C$_{2-20}$alkynyl, C$_{1-20}$acyl, C$_{3-8}$cycloalkyl, C$_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N=N, —N=O and NX$_1$X$_2$, wherein X$_1$ and X$_2$ are defined in the R$_3$ substituent described herein. In this formula, one or more of the hydrogen atoms of the indole ring can be replaced by Y. In some embodiments, R$_1$ can be halogen which may be one of fluorine, chlorine, iodine or bromine. In other embodiments, R$_1$ can be (CH$_3$)$_m$-aryl and m is an integer of 0, 1, 2, 3 or 4. In this context, the term "aryl" refers to an aromatic ring wherein each of the atoms forming the ring is a carbon atom. Aryl rings may be formed by five, six, seven, eight, nine, or more than nine carbon atoms. In some embodiments, aryl groups may be optionally substituted. Examples of aryl groups include, but are not limited to phenyl and naphthyl. The methyl (CH$_3$) substituent may be attached to any one of the main chain atoms of the aryl ring. As an illustrative example, when R$_1$ is a —CH$_3$—C$_6$H$_5$, the —CH$_3$ substituent can be attached to any of the carbon atoms of the phenyl ring. In some embodiments, R$_1$ may be 2'-CH$_3$—C$_6$H$_5$, 3'-CH$_3$—C$_6$H$_5$ or 4'-CH$_3$—C$_6$H$_5$.

In the compound of the present invention, R$_2$ can typically be an aliphatic chain having a main chain length of about 1 to about 10, to about 8, to about 5 or to about 3 carbon atoms. In this context, the term "aliphatic", alone or in combination, refers to a straight chain or branched chain hydrocarbon comprising at least one carbon atom, which may be saturated or mono- or poly-unsaturated and include heteroatoms. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to about 5, to about 8, to about 10 or to about 15 carbon atoms.

In some embodiments, R$_2$ can include, but are not limited to hydrogen, C$_{1-20}$alkyl, C$_{1-15}$alkyl, C$_{1-10}$alkyl, C$_{1-8}$alkyl, C$_{1-6}$alkyl, C$_{2-20}$alkenyl, C$_{2-10}$alkenyl, C$_{2-8}$alkenyl, C$_{2-20}$alkynyl, C$_{2-10}$alkynyl, C$_{2-8}$alkynyl, C$_{1-20}$acyl, C$_{1-10}$acyl, C$_{1-8}$acyl, C$_{1-6}$acyl, C$_{3-8}$cycloalkyl, C$_{3-8}$cycloalkenyl, aryl, heteroaryl or heteroalicyclyl. In other embodiments, R$_2$ can be C$_{1-8}$alkyl or C$_{2-8}$alkenyl. As an illustrative example, R$_2$ can include, but are not limited to methyl, ethyl, n-propyl, propyl, isopropyl, butyl, n-butyl, isobutyl, sec-butyl, tert-butyl, tert-amyl, pentyl, hexyl, heptyl, octyl, vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl. In certain embodiments, R$_2$ can be octyl or isoprenyl.

In some embodiments, R$_3$ has the formula of (CH$_2$)$_n$NX$_1$X$_2$ n being an integer of 1, 2, 3 or 4. In this formula of (CH$_2$)$_n$NX$_1$X$_2$, X$_1$ and X$_2$ can be the same substituent or can be different substituents. In certain embodiments, X$_1$ and X$_2$ can be independently selected from the group consisting of hydrogen, C$_{1-20}$alkyl, C$_{1-15}$alkyl, C$_{1-10}$alkyl, C$_{1-6}$alkyl, C$_{2-20}$alkenyl, C$_{2-10}$alkenyl, C$_{2-8}$alkenyl, C$_{2-20}$alkynyl, C$_{2-10}$alkynyl, C$_{2-8}$alkynyl, C$_{1-20}$acyl, C$_{1-10}$acyl, C$_{1-8}$acyl, C$_{1-6}$acyl, C$_{3-8}$cycloalkyl, C$_{3-8}$cycloalkenyl, aryl, heteroaryl, and heteroalicyclyl. In other embodiments, X$_1$ or X$_2$ may, together with the nitrogen atom bearing them, form a 3-8 membered ring or a 5-6 membered ring. The 3-8 or 5-6 membered ring can be a saturated ring. The 3-8 or 5-6 membered ring can be fused to at least one other respective 3-8 or 5-6 membered ring. The ring can also comprise 0, 1, 2, 3 or 4 further heteroatoms selected from the group consisting of oxygen, nitrogen, sulphur and phosphorus. The ring can be substituted by at least one substituent selected from the group consisting of hydrogen, hydroxyl, C$_{1-20}$alkyl, C$_{2-20}$alkenyl, C$_{2-20}$alkynyl, C$_{1-20}$acyl, C$_{3-8}$cycloalkyl, C$_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N═N, —N═O and $NX_1X_2$. The $X_1$ and $X_2$ substituents are defined in the compound of formula I.

In some embodiments, $R_4$ can be a hydrogen or $C_1$-$C_4$ alkyl, for example methyl, ethyl, propyl, isopropyl, butyl, not to mention a few.

The term "ring" as described herein refers to any covalently closed structure. Rings may include, for example, heterocycles (e.g. heteroaryls and non-aromatic heterocycles), aromatics (e.g. aryls and heteroaryls), and non-aromatics (e.g. non-aromatic heterocycles). Rings may be optionally substituted or rings may be fused to at least one ring to form part of a ring system. The term "ring system" refers to two or more rings, wherein two or more of the rings are fused. The term "fused" refers to structures which two or more rings share one or more bonds.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). As an illustrative example, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

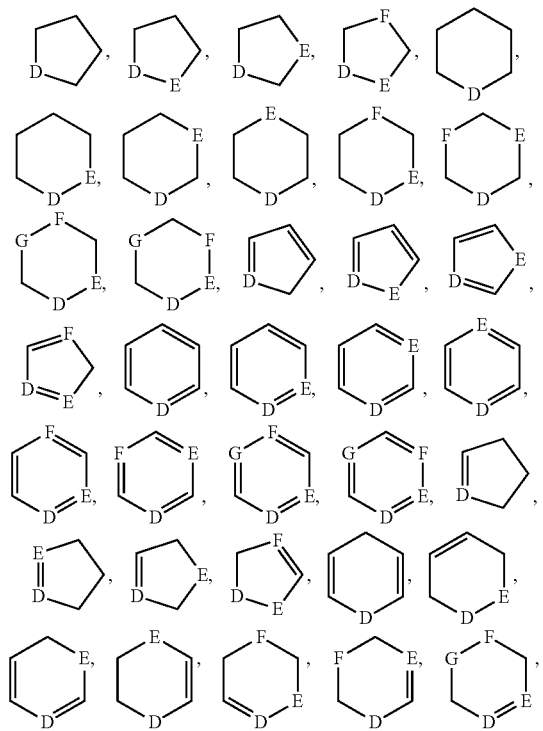

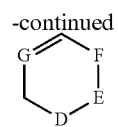

wherein D, E, F, and G independently represents a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed planar ring having a delocalized [pi]-electron system comprising 4n+2 [pi] electrons, where n is an integer. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon, atoms, and optionally carrying one or more substituents selected from an aryl, a heteroaryl, a. cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ aminoalkyl, alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoallyl, alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that is not aromatic.

The term "alkyl", alone or in combination, refers to a fully saturated aliphatic hydrocarbon. In certain embodiments, alkyls are optionally substituted. When substituted, the substituent group(s) is(are) one or more group(s) independently selected from cycloalkyl, aryl, heteroaryl, heteroalicyclyl, hydroxyl, protected hydroxyl, alkoxy, aryloxy, mercapto, alkylthio, arylthio, cyano, halogen, carbonyl, thiocarbonyl, O-carbamyl, O-thiocarbomyl, O-carboxy, isocyanato, thiocyanato, silyl, trihalomethanesulfonyl, and amino. In certain embodiments, an alkyl comprises 1 to 30 carbon atoms, for example 1 to 20 carbon atoms, 1 to 15 carbon atoms, 1 to 10 carbon atoms, or 1 to 5 carbon atoms, wherein a numerical range, such as "1 to 20" or "$C_1$-$C_{20}$", refers to each integer in the given range, e.g. "$C_1$-$C_{20}$ alkyl" means that an alkyl group comprising only 1 carbon atom, 2 carbon atoms, 3 carbon atoms, etc., up to and including 20 carbon atoms. Examples of alkyl groups include, but are not limited to, methyl, ethyl, n-propyl, propyl, isopropyl, butyl, n-butyl, isobutyl, sec-butyl, tert-butyl, tert-amyl, pentyl, hexyl, heptyl, octyl and the like.

The term "alkoxy", alone or in combination, refers to an aliphatic hydrocarbon having an alkyl-O— moiety. In certain embodiments, alkoxy groups are optionally substituted. When substituted, the substituent(s) may be selected from the same group disclosed above with regard to alkyl group substitution. Examples of alkoxy groups include, but are not limited to, methoxy, ethoxy, propoxy, butoxy and the like.

The term "alkenyl" or "alkene" as used herein refers to an alkyl group that contains in the straight or branched hydrocarbon chain one or more double bonds. In certain embodiments, an alkenyl comprises 2 to 30 carbon atoms, for example 2 to 20 carbon atoms, 2 to 15 carbon atoms, 2 to 10 carbon atoms, or 2 to 5 carbon atoms, wherein a numerical range, such as "2 to 20" or "$C_2$-$C_{20}$", refers to each integer in the given range, e.g. "$C_2$-$C_{20}$ alkenyl" means that an alkenyl group comprising 2 carbon atoms, 3 carbon atoms, etc., up to and including 20 carbon atoms. An alkenyl or alkene group of this invention may be substituted or unsubstituted. When substituted, the substituent(s) may be selected from the same group disclosed above with regard to alkyl group substitution. Examples of such groups include, but are not limited to, ethenyl, propenyl, butenyl, 1,4-butadienyl, pentenyl, hexenyl, 4-methylhex-1-enyl, 4-ethyl-2-methylhex-1-enyl and the like.

The term "alkynyl" or "alkyne" as used herein refers to an alkyl group that contains in the straight or branched hydrocarbon chain one or more triple bonds. In certain embodiments, an alkynyl comprises 2 to 30 carbon atoms, for example 2 to 20 carbon atoms, 2 to 15 carbon atoms, 2 to 10 carbon atoms, or 2 to 5 carbon atoms, wherein a numerical range, such as "2 to 20" or "$C_2$-$C_{20}$", refers to each integer in the given range, e.g. "$C_2$-$C_{20}$ alkynyl" means that an alkynyl group comprising 2 carbon atoms, 3 carbon atoms, etc., up to and including 20 carbon atoms. An alkynyl group of this invention may be substituted or unsubstituted. When substituted, the substituent(s) may be selected from the same group disclosed above with regard to alkyl group substitution. Examples of alkyne groups include, but are not limited to, ethynyl, propynyl, butynyl, and the like.

The term "acyl" as used herein is a group —RC(=O), an acyl group of this invention may be substituted or unsubstituted. In certain embodiments, an acyl comprises 1 to 30 carbon atoms, for example 1 to 20 carbon atoms, 1 to 15 carbon atoms, 1 to 10 carbon atoms, or 1 to 5 carbon atoms, wherein a numerical range, such as "1 to 20" or "$C_1$-$C_{20}$", refers to each integer in the given range, e.g. "$C_1$-$C_{20}$ acyl" means that an acyl group comprising 2 carbon atoms, 3 carbon atoms, etc., up to and including 20 carbon atoms. When substituted, the substituent(s) may be selected from the same group disclosed above with regard to alkyl group substitution. Examples of acyl groups include, but are not limited to formyl, acetyl, propanoyl, 2-methylpropanoyl, butanoyl and the like.

As used herein, "cycloalkyl" refers to a completely saturated hydrocarbon ring. Cycloalkyl groups of this invention may range from $C_3$ to $C_8$. A cycloalkyl group of this invention may be substituted or unsubstituted. When substituted, the substituent(s) may be selected from the same group disclosed above with regard to alkyl group substitution. Examples of cycloalkyl groups include, but are not limited to cyclopropyl, cyclobutyl, cyclopentyl, cyclohexyl and the like.

The term "cycloalkenyl" as used herein refers to a cycloalkyl group that contains one or more double bonds in the ring although, if there is more than one, they cannot form a fully delocalized pi-electron system in the ring (otherwise the group would be "aryl" as defined herein). Cycloalkyl groups of this invention may range from $C_3$ to $C_8$. A cycloalkenyl group of this invention may be substituted or unsubstituted. When substituted, the substituent(s) may be selected from the same group disclosed above with regard to alkyl group substitution. Examples of cycloalkenyl groups include, but are not limited to cyclohexenyl, cyclohepta-1,3-dienyl, cyclopropenyl, cyclobutenyl, cyclopentenyl, cyclohexenyl, cycloheptenyl and the like.

As used herein, the term "heteroalicyclyl" refers to a ring or one or more fused rings having in the ring system one or more heteroatoms. The rings may also contain one or more double bonds provided that they do not form a fully delocalized pi-electron system in the rings. Heteroalicyclyl groups of this invention may be unsubstituted or substituted. When substituted, the substituent(s) may be one or more groups independently selected from the group consisting of halogen, hydroxyl, protected hydroxyl, cyano, nitro, alkyl, alkoxy, acyl, acyloxy, carboxy, amino and carboxamide.

The term "optionally substituted" refers to a group in which none, one, or more than one of the hydrogen atoms has been replaced with one or more group(s) are independently selected from: alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups.

In some embodiments, $R_3$ can be $CH_2NH_2$, $CH_2N(CH_3)_2$, $CH_2N(C_2H_5)_2$, $CH_2N(C_3H_7)_2$,

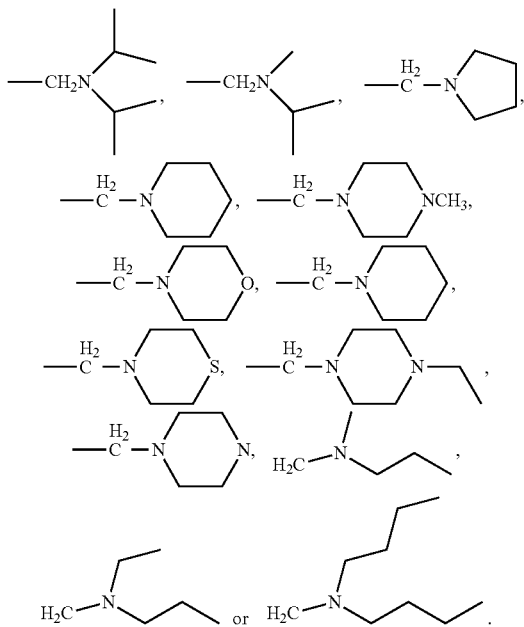

The inventors have shown that modifications at the $R_3$ substituent or concurrently at both the $R_3$ and $R_2$ substituents as depicted in Formula I for example, resulted in a surprising effect on the biological activities of the compounds described herein. As an illustrative example (see for example FIGS. 5 to 8), a conversion from an amide side chain to a basic amine side chain at the $R_3$ position of Formula I can results in compounds that are up to about three times as potent as cysmethynil as Icmt inhibitors and/or at least about eight times more potent as anti-proliferative agents. In another illustrative example, when the $R_3$ substituent is replaced with an amine side chain followed by a concurrent replacement of the $R_2$ substituent with a shorter and less lipophilic side chain such as isoprenyl for example, up to a 10-fold increase in anti-proliferative activity is seen although the Icmt inhibitory activity is retained (Series 6, Table 6).

In certain embodiments, the compound of the invention can be a compound of formula Ia

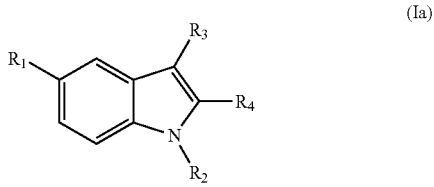

(Ia)

or a pharmaceutically acceptable salt thereof. In this compound, $R_1$ is a halogen or $(CH_3)_m$-aryl, m being an integer between 0 to 4. $R_2$ is $C_{1-10}$ alkyl or $C_{2-10}$ alkenyl; $R_3$ is $(CH_2)_nNX_1X_2$, n being an integer from 1 to 4; $R_4$ is a hydrogen or $C_1$-$C_4$ alkyl; $X_1$ and $X_2$ are independently $C_1$-$C_{10}$ alkyl; or $X_1$ or $X_2$ may, together with the nitrogen bearing them, form a 5-6 membered ring, wherein the 5-6 membered ring can be fused to at least one 5-6 membered ring, wherein the ring can optionally comprise 0, 1, 3 or 4 further heteroatoms selected from the group consisting of oxygen, nitrogen, sulphur, and phosphorus; and wherein the ring can be substituted by at least one substituent selected from the group consisting of halogen, hydroxyl, oxo, $C_1$-$C_6$ alkyl, $C_2$-$C_6$ alkenyl, $C_2$-$C_6$ alkynyl, $C_1$-$C_6$ acyl, $C_{3-8}$ cycloalkyl, and $C_{3-8}$ cycloalkenyl.

In some embodiments, compounds of the present invention may include any of the following:

1-octyl-5-m-tolyl-1H-indol-3-yl)methanamine (J18);
N,N-dimethyl(1-octyl-5-m-tolyl-1H-indol-3-yl)methanamine (J25G);
N-ethyl-N-((1-octyl-5-m-tolyl-1H-indol-3-yl)methyl)ethanamine (J17G);
N-((1-octyl-5-m-tolyl-1H-indol-3-yl)methyl)-N-propylpropan-1-amine) (J27G);
N-isopropyl-N-((1-octyl-5-m-tolyl-1H-indol-3-yl)methyl)propan-2-amine (J26G);
N-methyl-N-((1-octyl-5-m-tolyl-1H-indol-3-yl)methyl)propan-2-amine (J29G);
1-octyl-3-(pyrrolidin-1-ylmethyl)-5-m-tolyl-1H-indole (J31G);
1-octyl-3-(piperidin-1-ylmethyl)-5-m-tolyl-1H-indole (J32G);
3((4-methylpiperazin-1-yl)methyl)-1-octyl-5-m-tolyl-1H-indole (J30G);
3-(morpholinomethyl)-1-octyl-5-m-tolyl-1H-indole (J34G);
N-ethyl-N-((1-octyl-5-o-tolyl-1H-indol-3-yl)methyl)ethanamine (J36G);
N-ethyl-N-((1-octyl-5-p-tolyl-1H-indol-3-yl)methyl)ethanamine (J37G);
N-ethyl-N-((5-fluoro-1-octyl-1H-indol-3-yl)methyl)ethanamine (J40G);
N-ethyl-N-((1-(3-methylbut-2-enyl)-5-m-tolyl-1H-indol-3-yl)methyl)ethanamine (J38G);
1-(3-methylbut-2-enyl)-3-(piperidin-1-ylmethyl)-5-m-tolyl-1H-indole (J39G);
N-ethyl-N-((1-(3-methylbut-2-enyl)-1H-indol-3-yl)methyl)ethanamine (J35G);
1-(5-fluoro-1-octyl-1H-indol-3-yl)-N,N-dimethylmethanamine;
5-fluoro-1-octyl-3-(piperidin-1-ylmethyl)-1H-indole;
4-((5-fluoro-1-octyl-1H-indol-3-yl)methyl)thiomorpholine;
4-((5-fluoro-1-octyl-1H-indol-3-yl)methyl)morpholine;
5-fluoro-1-octyl-3-(pyrrolidin-1-ylmethyl)-1H-indole;
5-fluoro-3((4-methylpiperazin-1-yl)methyl)-1-octyl-1H-indole; and
4-((1-(3-methylbut-2-enyl)-5-m-tolyl-1H-indol-3-yl)methyl)morpholine.

In other embodiments, the compounds of the present invention can also include 2-(5-Fluoro-1-octyl-1H-indol-3-yl)acetamide) (1-8);
2-(5-Fluoro-1-(3-methylbut-2-enyl)-1H-indol-3-yl)acetamide (6-8);
1-(4-Methylpiperazin-1-yl)-2-(1-octyl-5-m-tolyl-1H-indol-3-yl)ethanone (3-6);
N-Methyl-2-(1-octyl-5-m-tolyl-1H-indol-3-yl)acetamide (3-7);
1-Octyl-5-m-tolyl-1H-indole-3-carboxamide (5-1);
3-(1-Octyl-5-m-tolyl-1H-indol-3-yl)propanamide (5-2);
1-(3-Methylbut-2-enyl)-5-m-tolyl-1H-indole (6-3);
4-((1-(3-methylbut-2-enyl)-5-m-tolyl-1H-indol-3-yl)methyl)morpholine (6-6)
N-((5-fluoro-1-octyl-1H-indol-3-yl)methyl)-N-methylpropan-1-amine (6-9(7));
N-ethyl-N-((5-fluoro-1-octyl-1H-indol-3-yl)methyl)propan-1-amine (6-9 (8));
N-butyl-N-((5-fluoro-1-octyl-1H-indol-3-yl)methyl)butan-1-amine (6-9-(9));

(E)-1-(1-(3,7-dimethylocta-2,6-dienyl)-5-fluoro-1H-indol-3-yl)-N,N-dimethylmethanamine (6-13a);
(E)-N-((1-(3,7-dimethylocta-2,6-dienyl)-5-fluoro-1H-indol-3-yl)methyl)-N-ethylethanamine (6-13b);
(E)-1-(3,7-dimethylocta-2,6-dienyl)-5-fluoro-3-(piperidin-1-ylmethyl)-1H-indole (6-13c);
(E)-4-((1-(3,7-dimethylocta-2,6-dienyl)-5-fluoro-1H-indol-3-yl)methyl)thiomorpholine (6-13d);
(E)-4-((1-(3,7-dimethylocta-2,6-dienyl)-5-fluoro-1H-indol-3-yl)methyl)morpholine (6-13e);
(E)-1-(3,7-dimethylocta-2,6-dienyl)-5-fluoro-3-(pyrrolidin-1-ylmethyl)-1H-indole (6-13f);
(E)-1-(3,7-dimethylocta-2,6-dienyl)-5-fluoro-3-((4-methylpiperazin-1-yl)methyl)-1H-indole (6-13g);
(E)-N-((1-(3,7-dimethylocta-2,6-dienyl)-5-fluoro-1H-indol-3-yl)methyl)-N-methylpropan-1-amine (6-13h);
N-ethyl-N-((5-fluoro-1-octyl-1H-indol-3-yl)methyl)propan-1-amine (6-13j);
(E)-N-butyl-N-((1-(3,7-dimethylocta-2,6-dienyl)-5-fluoro-1H-indol-3-yl)methyl)butan-1-amine (6-13j);
(E)-1-(3,7-dimethylocta-2,6-dienyl)-3 ethylpiperazin-1-yl)methyl)-5-fluoro-1H-indole (6-13k);
N,N-dimethyl-1-(1-(3-methylbut-2-enyl)-5-m-tolyl-1H-indol-3-yl)methanamine (6-14);
4-((1-(3-methylbut-2-enyl)-5-m-tolyl-1H-indol-3-yl)methyl)thiomorpholine (6-15);
1-(3-methylbut-2-enyl)-3-(pyrrolidin-1-ylmethyl)-5-m-tolyl-1H-indole (6-16);
1-(3-methylbut-2-enyl)-3-((4-methylpiperazin-1-yl)methyl)-5-m-tolyl-1H-indole (6-17);
N-methyl-N-((1-(3-methylbut-2-enyl)-5-m-tolyl-1H-indol-3-yl)methyl)propan-1-amine (6-18);
N-ethyl-N-((1-(3-methylbut-2-enyl)-5-m-tolyl-1H-indol-3-yl)methyl)propan-1-amine (6-19);
N-butyl-N-((1-(3-methylbut-2-enyl)-5-m-tolyl-1H-indol-3-yl)methyl)butan-1-amine (6-20); and
N-((1-(3-methylbut-2-enyl)-5-m-tolyl-1H-indol-3-yl)methyl)-N-propylpropan-1-amine (6-21).

The present invention also encompass the corresponding physiologically or toxicologically acceptable salts, in particular the pharmaceutically acceptable salts. Thus, compounds of the present invention which may contain one or more basic, that is protonatable, groups may be in the form of their acid addition salts with physiologically acceptable inorganic or organic salts and used according to the invention, for examples salts with hydrochloric acid, hydrobromic acid, phosphoric acid, sulfuric acid, nitric acid, methanesulfonic acid, p-toluenesulfonic acid, naphthalenedisulfonic acid, oxalic acid, acetic acid, tartaric acid, lactic acid, salicyclic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc.

Salts can be obtained from the compounds of the present invention by conventional processes known to the person skilled in the art, for example, by combining with an organic or inorganic acid or base in a solvent or dispersant, or else by anion exchange or cation exchange from other salts. The present invention further encompass all solvates of the compounds of the present invention, for example hydrates or adducts with alcohols, and derivatives of the compounds disclosed herein such as, for example, esters and prodrugs and active metabolites.

The compounds of the present invention or pharmaceutically acceptable salts thereof, can be synthesized using techniques commonly known in the art and readily available starting materials. The synthesis procedure can for example be carried out as described in Na, Y, M et al, *Eur. J. Med. Chem.* 2003, 38, 75-87. The synthesis route for the compounds described herein is described further in the Examples described herein. Compounds according to the invention for example, the compound of the general formula I can be obtained as shown in the synthesis scheme in Example 5, Scheme 6. In an illustrative embodiment, the compound(s) of formula I can be prepared by adding a phosphine compound to a solution containing the compound of formula II

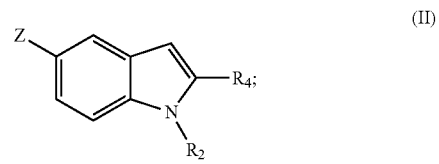

under conditions to form a compound of formula III

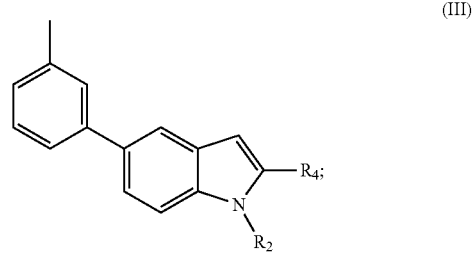

and adding an amine and a carbonyl compound to the solution in step i) to form a compound of formula I. The $R_2$ and $R_4$ substituents in formulaes II and III is defined in the compound of formula I described herein. In certain embodiments, the phosphine compound can be $Pd(PH_3)_4$. The leaving group Y can be a halogen atom for example, one of chlorine, iodine or bromine. In this context, when adding the phosphine compound to obtain the compound of formula III, a boronic acid such as a meta-substituted phenylboronic acid for example, can be added to the solution containing the compound of formula II, to obtain the compound of formula III.

In other embodiments, to obtain a compound of formula I for example, a sulphonyl compound can be added to a solution containing the compound of formula IV

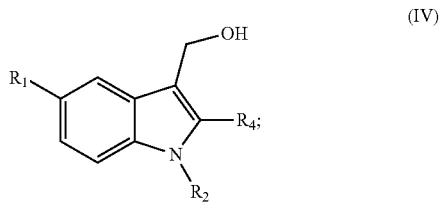

under conditions to form a sulphonate ester compound. An amine is then added to the solution containing the sulphonate ester compound, under conditions to form a compound of formula I. In this context, the $R_1$, $R_2$ and $R_4$ substituents in formula IV are defined in the compound of formula I described herein.

As an illustrative example, the compound of formula I as described in the present invention can be obtained using the following scheme:

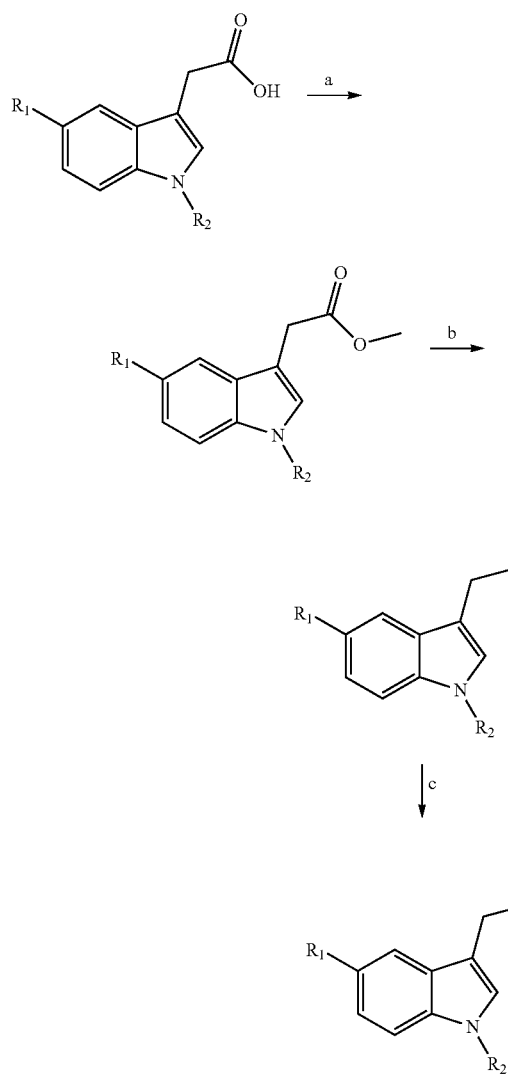

a MeOH, H₂SO₄, reflux: To form ester
b LiAlH₄, THF: Reduction of ester to alcohol
c (i) TEA, Methanesulphonylchloride (ii) Amine, reflux if necessary (replacement of methane sulphonyl ester with amine)

In some embodiments, to obtain a compound of formula I, in which $R_3$ is $(CH_2)_n NX_1X_2$, n being an integer from 2 to 4, a methylating agent such as diazomethane for example, is added into a solution containing the compound of formula V

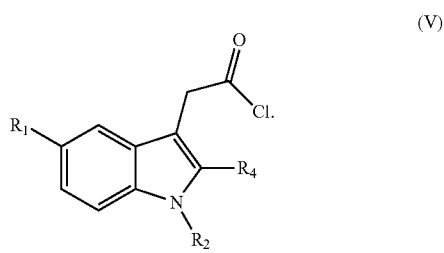

The methylating agent is added into the solution containing the compound of formula V, in order to add a carbon atom to the acid chloride side chain, to form a compound of formula VI

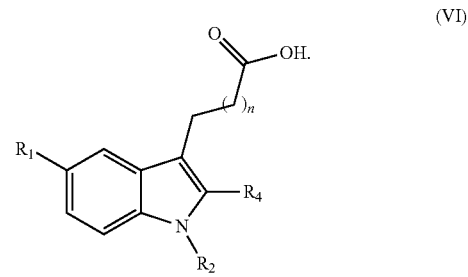

In this context, the step of adding the methylating agent can be repeated 1, 2, 3 or 4 times, in order to add a respective 1, 2, 3, or 4 extra carbon atom(s) to the acid chloride side chain. Once the acid compound of formula VI is obtained, the acid compound of formula VI can be converted to an ester which is followed by a reduction to an alcohol compound by adding lithium aluminium hydride. A sulphonyl compound can be added to the solution containing the alcohol compound of formula VI to form a sulphonyl ester compound. To form the compound of formula I, the sulphonyl ester group can be substituted by an amine, by adding an amine to the solution containing the sulphonyl ester compound.

As an illustrative example, the compound of formula I can be obtained using the following scheme:

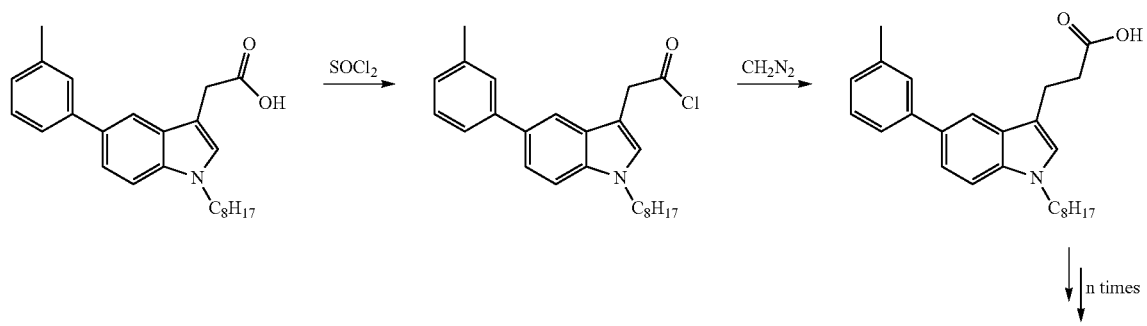

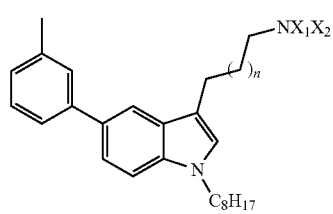 ← 2° amine 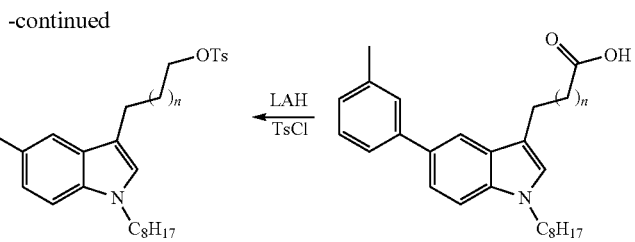

The present invention also provides a compound of formula VII,

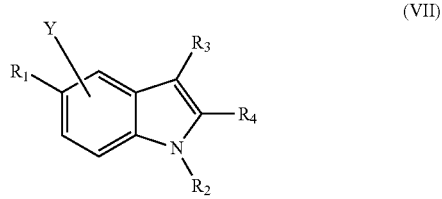

(VII)

in which $R_1$ and Y are respectively defined above. In this compound of formula VIII, $R_2$ can be a terpenoid. The term "terpenoid" is understood to cover terpenes and oxygen containing derivatives thereof having at least one $C_5H_8$ hydrocarbyl unit which may have one or more points of unsaturation and/or be part of a cyclic unit within the compound. Terpenoids can include, but are not limited to hemiterpenoids, monoterpenoids, sesquiterpenoids, diterpenoids, sesterterpenoids, triterpenoids, tetraterpenoids, and polyterpenoids. As an illustrative example, the substituent $R_2$ in the compound of general formula VII can be geranyl. In this context, when $R_2$ is a terpenoid, $R_3$ is $(CH_2)_n CONX_1X_2$, in which n can be an integer from 1 to 4, and $X_1$ and $X_2$ are respectively defined above.

The present invention also provides a compound of formula VIII,

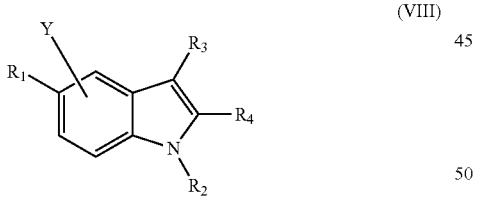

(VIII)

in which $R_1$, Y and $R_2$ are respectively defined above. In this compound of formula VIII, $R_3$ can be $(CH_2)_n CONX_1X_2$, n being an integer from 1 to 4. $X_1$ and $X_2$ together with the nitrogen atom bearing them, form a 3-8 membered ring, wherein the 3-8 membered ring can be fused to at least one 3-8 membered ring, wherein the ring can optionally comprise 0, 1, 2, 3 or 4 further heteroatoms selected from the group consisting of oxygen, nitrogen, sulphur and phosphorus; and wherein the ring can be substituted by at least one substituent selected from the group consisting of hydrogen, hydroxyl, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, perhaloalkyl, sulfonyl, sulfonamide, thio, —CN, —COOH, —SH, —N=N, —N=O and $NX_1X_2$. As an illustrative example for this compound of formula VIII, $R_3$ can be one of

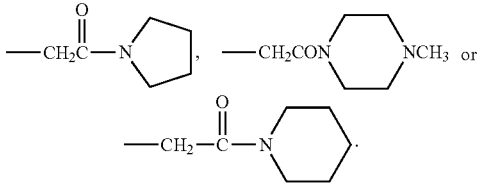

The present invention also provides a compound of formula IX,

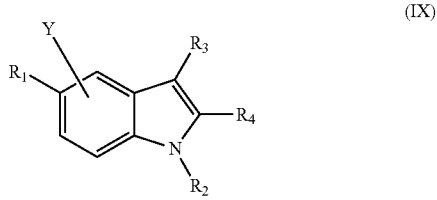

(IX)

in which $R_1$, Y and $R_2$ are respectively defined above. In this compound of formula IX, the $R_3$ substituent can be —$(CH_2)_2CONH_2$ or $CH_2NH_2SO_2CH_3$.

The present invention also provides a compound of formula X

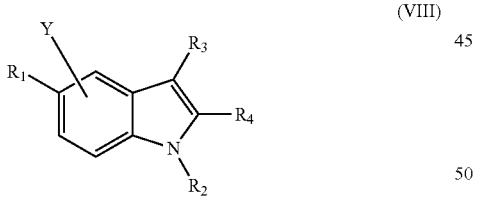

(X)

In this compound, $R_1$ and Y are independently selected from the group consisting of hydrogen, hydroxyl, $C_{1-20}$allyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, heteroalicyclyl, halogen, carbonyl, thiocarbonyl, O-carbamyl, O-thiocarbonyl, O-carboxy, isocyanato, thiocyanato, silyl, sulfonamide, thio, —CN, —COOH, —SH, —N=N, —N=O and $NX_1X_2$, wherein one or more of the hydrogen atoms of the indole ring can be replaced by Y; $R_2$ is selected from the group consisting of hydrogen, $C_{1-20}$alkyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl and heteroalicyclyl; and $R_3$ is $(CH_2)_n CONX_1X_2$, n being an integer from 1 to 4; wherein $X_1$ is hydrogen and $X_2$ is one selected from the group consisting of $C_{1-20}$allyl, $C_{2-20}$alkenyl, $C_{2-20}$alkynyl, $C_{1-20}$acyl, $C_{3-8}$cycloalkyl, $C_{3-8}$cycloalkenyl, aryl, heteroaryl, and heteroalicyclyl.

The present invention also relates to a method of killing a cell such as a tumor cell, e.g. a cancerous cell or a precancerous cell. The method includes administering a compound of the present invention as described herein. Any cell may be used in the present method of the invention. In some embodiments, the cell used according to the invention may be comprised in a mammal. In other embodiments, the cell as used in the invention may be cultured. The cultured cell may also be obtained from a mammal. Examples of mammals include, but are not limited to, a rat, a cow, a goat, a sheep, a pig, a dog, a mouflon, a guinea pig, a hamster, a chimpanzee, a rhesus monkey and a human. In some embodiments, the cell used in the invention may be a tumor cell. In other embodiments, the tumor may derive from a cancer. Any tumor or cancer may be used in the invention including for example, a benign tumor and a metastatic malignant tumor. Examples of tumors include, but are not limited to, haematological malignancies and solid tumours. Solid tumours include for instance a sarcoma, arising from connective or supporting tissues, a carcinoma, arising from the body's glandular cells and epithelial cells or a lymphoma, a cancer of lymphatic tissue, such as the lymph nodes, spleen, and thymus. Examples of a solid tumour include, but are not limited to, breast cancer, lung cancer, a brain tumour, a neuroblastoma, colon cancer, rectal cancer, bladder cancer, a liver tumour, a pancreatic tumour, ovarian cancer, prostate cancer, melanoma, cancer of the head or neck and leukaemia.

The compounds of the present invention can be formulated into compositions, for example pharmaceutical compositions, suitable for administration. Where applicable, a compound of the present invention may be used in its ionic transition state or any pharmaceutically acceptable salt thereof. A compound as defined above, or a pharmaceutically acceptable salt thereof, can be used per se, or in a pharmaceutical composition where it may be mixed with other active ingredients, as in combination therapy, and/or a suitable carrier or diluent.

Examples of other active ingredients that may be included in a pharmaceutical composition include, but are not limited to, a nucleic acid alkylator, a nucleoside analogue, an anthracycline, an antibiotic, an aromatase inhibitor, a folate antagonist, an estrogen receptor modulator, an inorganic aresenate, a microtubule inhibitor, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

Alkylators that may be included in the pharmaceutical composition of the present invention include but are not limited to busulfan (Myleran®, Busilvex®), chlorambucil (Leukeran®), ifosfamide (Mitoxana®, with or without MESNA), cyclophosphamide (Cytoxan®, Neosar®), glufosfamide, melphalan/L-PAM (Alkeran®), dacarbazine (DTIC-Dome®), and temozolamide (Temodar®). As an illustrative example, the compound 2-bis[(2-chloroethyl)amino]tetrahydro-2H-1,3,2-oxazaphosphorine, 2-oxide, also commonly known as cyclophosphamide, is an alkylator used in the treatment of stages III and IV malignant lymphomas, multiple myeloma, leukemia, mycosis fungoides, neuroblastoma, ovarian adenocarcinoma, retinoblastoma, and carcinoma of the breast.

Nucleoside analogues that may be included in the pharmaceutical composition of the present invention include, but are not limited to, cytarabine (Cytosar®) and gemcitabine (Gemzar®), two fluorinated deoxycytidine analogues, fludarabine (Fludara®), a purine analog, 6-mercaptopurine (Puri-Nethol®) and its prodrug azathioprine (Imuran®).

Anthracyclines that may be included in the pharmaceutical composition of the present invention include, but are not limited to, doxorubicin (Adriamycin®, Doxil®, Rubex®), mitoxantrone (Novantrone®), idarubicin (Idamycin®), valrubicin (Valstar®), and epirubicin (Ellence®). As one example, the compound (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, more commonly known as doxorubicin, is a cytotoxic anthracycline antibiotic isolated from cultures of Streptomyces peucetius var. caesius. Doxorubicin has been used successfully to produce regression in disseminated neoplastic conditions such as acute lymphoblastic leukemia, acute myeloblastic leukemia, Wilm's tumour, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

Antibiotics that may be included in the pharmaceutical composition of the present invention include but are not limited to dactinomycin, actinomycin D (Cosmegen®), daunorubicin/daunomycin (Cerubidine®, DanuoXome®), bleomycin (Blenoxane®), epirubicin (Pharmorubicin®) and mitoxantrone (Novantrone®). Aromatase inhibitors useful in the practice of the present invention include but are not limited to anastrozole (Arimidex®) and letroazole (Femara®). Bisphosphonate inhibitors that may be included in the pharmaceutical composition of the present invention include but are not limited to zoledronate (Zometa®).

Cyclooxygenase inhibitors that may be included in the pharmaceutical composition of the present invention include but are not limited to acetylsalicylic acid (Aspiring), celecoxib (Celebrex®) and rofecoxib (Vioxx®, Ceoxx®, Ceeoxx®). Estrogen receptor modulators that may be included in the composition of the present invention include but are not limited to tamoxifen (Nolvadex®) and fulvestrant (Faslodex®). Folate antagonists that may be included in the composition of the present invention include but are not limited to methotrexate (Trexall®, Rheumatrex®) and trimetrexate (Neutrexin®). As an illustrative example, the compound (S)-2-(4-(((2,4-diaminopteridin-6-yl)methyl)methylamino)benzamido)pentanedioic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides.

Inorganic arsenates that may be included in the pharmaceutical composition of the present invention include but are not limited to arsenic trioxide (Trisenox®). Microtubule inhibitors (as used herein, a "microtubule inhibitor" is any agent that interferes with the assembly or disassembly of microtubules) that may be included in the composition of the present invention include but are not limited to vincristine (Oncovin®), vinblastine (Velban®), paclitaxel (Taxol®, Paxene®), vinorelbine (Navelbine®), docetaxel (Taxotere®), epothilone B or D or a derivative of either, and discodermolide or its derivatives.

Nitrosoureas that may be included in the pharmaceutical composition of the present invention include but are not limited to procarbazine (Matulane®), lomustine (CeeNU®), carmustine (BCNU®, BiCNU®, Gliadel Wafer®), and estramustine (Emcyt®). Nucleoside analogs that may be included in the pharmaceutical composition of the present invention include but are not limited to 6-mercaptopurine (Purinethol®), 5-fluorouracil (Adrucil®), 6-thioguanine (Thioguanine®), hydroxyurea (Hydrea®), cytarabine (Cytosar-U®, DepoCyt®), floxuridine (FUDR®), fludarabine (Fludara®), pentostatin (Nipent®), cladribine (Leustatin®, 2-CdA®), gemcitabine (Gemzar®), and capecitabine (Xeloda®). As an illustrative example, the compound 5-fluoro-2,4(1H,3H)-pyrimidinedione, also commonly known as 5-fluorouracil, is an antimetabolite nucleoside analogue effective in the palliative management of carcinoma of the colon, rectum, breast, stomach, and pancreas in patients who are considered incurable by surgical or other means. Another example of a nucleoside analogue is Gemcitabine. Gemcitabine is 2'-deoxy-2',2'-difluoro-cytidine. It is commercially available as the monohydrochloride salt, and as the beta-isomer. It is also known chemically as 1-(4-amino-2-oxo-1-H-pyrimidin-1-yl)-2-desoxy-2,2-difluororibose.

An illustrative example of an osteoclast inhibitor that may be included in the pharmaceutical composition of the present invention is pamidronate (Aredia®). Platinum compounds that may be included in the pharmaceutical composition of the present invention include, but are not limited to, cisplatin (Platinol®) and carboplatin (Paraplatin®). Retinoids that may be included in the pharmaceutical composition of the present invention include but are not limited to tretinoin, ATRA (Vesanoid®), alitretinoin (Panretin®), and bexarotene (Targretin®). Topoisomerase 1 inhibitors that may be included in the pharmaceutical composition of the present invention include, but are not limited to, topotecan (Hycamtin®) and irinotecan (Camptostar®, Camptothecan-11®). Topoisomerase 2 inhibitors that may be included in the pharmaceutical composition of the present invention include, but are not limited to, etoposide (Etopophos®, Vepesid®) and teniposide (Vumon®).

Examples of a tyrosine kinase inhibitors that may be included in the pharmaceutical composition of the present invention include, but are not limited to, dasatinib (Sprycel®), erlotinib (Tarceva®), gefitinib (Iressa®), imatinib (Gleevec®), lapatinib (Tykerb®), sorafenib (Nexavar®) and vandetanib (Zactima®). Examples of a (recombinant) growth factor that may be included in the pharmaceutical composition of the present invention include, but are not limited to, interleukin-11, interferon-α-2b and interleukin-2. An illustrative example of a thymidylate synthase inhinitor that may be included in the pharmaceutical composition of the present invention is Raltitrexed®. Examples of a monoclonal antibody that may be included in the pharmaceutical composition of the present invention include, but are not limited to, rituximab (MabThera®) or cetuximab (Erbitux®).

The invention also provides a pharmaceutical composition comprising a compound of the present invention, for example, a compound of formula I. The pharmaceutical composition may be administered by, for example, the oral, topical, dermal, ocular, intravenous, intraarticular, rectal, vaginal, inhalation, intranasal, sublingual or buccal route. Exemplary routes of administration of a respective compound or pharmaceutical composition include oral, transdermal, and parenteral delivery. Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumour, such as in a depot or sustained release formulation. Furthermore, a respective compound or pharmaceutical composition may be used in a targeted drug delivery system, for example, in a liposome coated with a tumour-specific antibody. Such liposomes may for example be targeted to and taken up selectively by a tumour.

The present invention also relates to a method of treating a mammal having a disease or disorder associated with Icmt activity. The method includes administering to the mammal a compound of the present invention, for example, formula I or a pharmaceutical composition as defined above. In certain embodiments, the compound or the pharmaceutical composition described herein can be used for treating cancer or a disease or disorder associated with Icmt activity. A respective use may for example be the manufacture of a medicament for this purpose. Accordingly, the method of the invention includes the use of a compound as defined above, including the use in the manufacture of a medicament.

In order that the invention may be readily understood and put into practical effect, particular embodiments will now be described by way of the following non-limiting examples.

EXAMPLES

The following experimental examples are provided to further illustrate the present invention and are not intended to be limiting to the scope of the invention.

Example 1

Synthesis of Compounds of Series 1, Table 1

Scheme 1: Preparation of Primary amides (Cysmethynil, J9, J10, J14-J16, J20-J24)

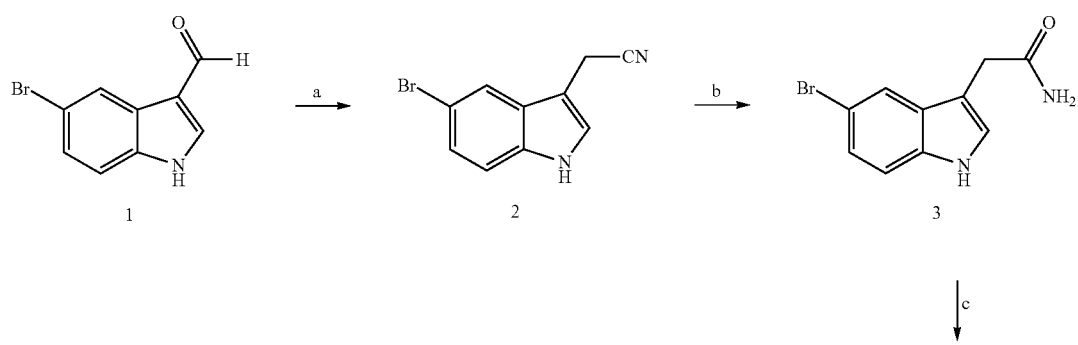

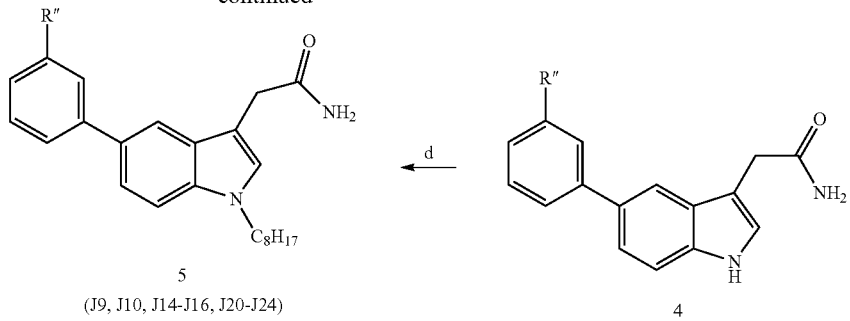

5
(J9, J10, J14-J16, J20-J24)

4

R = n-Octyl, Isopreny, Gerenyl
a (i) NaBH4, NH2CHO-MeOH, rt (0.5 h) (ii) KCN, 100° C. (3 h)
b KOH, t-BuOH, reflux (3 h)
c meta-substituted phenylboronic acid, Pd(PPh3)4, NaHCO3, EtOH/toluene, reflux (1-6 h)
d R—X (X = halogen), NaH, DMF, rt (1.5 h) 53-58° C. (3-6 h)

Preparation of 2-(5-bromo-1H-indol-3-yl)acetonitrile (2). To a solution of 5-bromo-1H-indole-3-carbaldehyde (1) (1 g, 4.5 mmol) in NH$_2$CHO-MeOH (1:1, v/v, 200 ml) was added NaBH$_4$ (0.5 g, 13.5 mmol) and the mixture was stirred for 0.5 h. To the reaction mixture was added KCN (3 g, 45 mmol) and the whole was refluxed on oil bath at 100° C. for 2.5 h with stirring. After cooling to room temperature, brine was added and the whole was extracted with CHCl$_3$. The extract was washed with brine dried over Na$_2$SO$_4$, and evaporated under reduced pressure to give the nitrile 2. Recrystallization from EtOH/water gave needle-like white crystals (0.861 g, 81%).

Preparation of 2-(5-bromo-1H-indol-3-yl)acetamide (3. Nitrile 2 (0.826 g, 3.5 mmol), was refluxed in t-BuOH (10 ml) containing finely powdered 85% KOH (1.85 g, 28 mmol) for 3 h. The reaction mixture was cooled to room temperature, diluted with water, and acidified with 1 N HCl. The resulting suspension was filtered at the vacuum and filter cake was washed with water then dried in vacuo. The product was isolated as an off-white/light brown solid (0.789 g, 89%).

General Procedure for Preparation of 5-phenyl-1H-indoles (4). To a suspension of bromoindole (3) (2 mmol) in anhydrous toluene (40 ml) in an ice bath was added Pd(PPh$_3$)$_4$ (0.12 g, 5.7 mol %). The suspension was stirred for 0.5 h. To the resulting bright yellow suspension was added in one portion a solution of meta-substituted phenylboronic acid (3 mmol, 1, 5 equiv) in absolute EtOH (10 ml) followed immediately by a saturated aqueous solution of NaHCO$_3$ (25 ml). After refluxing for 1-6 h, the biphasic mixture was cooled to room temperature and then poured into a solution of saturated aqueous NaCl. The organic phase was separated and the aqueous phase was extracted with EtOAc. Organic extracts were combined and dried (Na$_2$SO$_4$). The drying agent was removed by filtration and the filtrate was concentrated under reduced pressure to give the crude product 4.

General Procedure for Preparation of 1-octyl-5-phenyl-1H-indoles (5). To a stirred suspension of NaH (60% dispersion in mineral oil, 0.12 g, 3 mmol) in anhydrous dimethylformamide (DMF; 5 ml) in ice bath was added a solution of crude phenyl indole 4 (2 mmol) in anhydrous DMF (10 ml) drop wise over a period of 10 min. After stirring at room temperature for 1.5 h, following which 1-bromooctane (1.0 ml, 6 mmol) was added drop wise over 5 min. After being heated on an oil bath at 53-58° C. for 3-6 h, the reaction mixture was cooled to room temperature and poured into ice water. The suspension was stirred 10 min and extracted with Et$_2$O. The organic extracts were combined, washed with brine, and dried (Na$_2$SO$_4$). The drying agent was removed by filtration and the filtrate was concentrated under reduced pressure to give the crude product 5.

Cysmethynil (2-(1-octyl-5-m-tolyl-1H-indol-3-yl) acetamide) MS-APCI: [M+1]$^+$ 377.5 (377.3); $\delta_H$ (CD3OD, 300 MHz): 0.92 (t, 3 H, J 15 Hz, CH3), 1.29-1.35 (m, 10H, CH2), 1.88 (t, 2 H, J 15 Hz, CH2), 2.42 (s, 3 H, CH3), 3.70 (s, 2 H, CH2), 4.20 (t, 2 H, J 15 Hz, CH2), 7.12 (d, 1 H, J 9 Hz, ArH), 7.21-7.32 (m, 2 H, ArH), 7.37-7.48 (m, 4 H, ArH), 7.80 (s, 1H, ArH) $\delta_C$ (CD3OD, 75 MHz): 13.6, 20.8, 22.8, 27.2, 29.5, 29.6, 30.6, 32.1, 32.6, 46.3, 108.6, 110.0, 117.3, 121.5, 124.5, 127.1, 127.6, 128.2, 128.7, 131.1, 133.1, 136.6, 138.4, 143.0, 177.0

J8 2-(5-(3-ethoxyphenyl)-1-octyl-1H-indol-3-yl) acetamide MS-APCI: [M+1]$^+$ 407.4 (407.5) $\delta_H$ (DMSO-d6, 300 MHz): 0.90 (t, 3 H, J 12 Hz, CH3), 1.05-1.15 (m, 6 H, CH3), 1.27-1.31 (m, 10 H, CH2), 1.84 (t, 2 H, J 9 Hz, CH2), 3.40-3.48 (m, 4 H, CH2), 3.87 (s, 3 H, CH3), 3.88 (s, 2 H, CH2), 4.19 (t, 2 H, J 15 Hz, CH2), 6.87 (d, 1 H, J 6 Hz, ArH), 7.14-7.44 (m, 6 H, ArH), 7.83 (s, 1 H, ArH) $\delta_C$ (DMSO-d6, 75 MHz): 15.0, 15.8, 23.1, 27.4, 29.7, 29.8, 31.0, 32.2, 33.3, 46.5, 64.0, 110.1, 111.0, 113.0, 114.0, 118.4, 120.0, 121.4, 128.9, 129.2, 130.8, 131.8, 136.6, 144.4, 160.0, 173.8

J9 2-(5-(3-methoxyphenyl)-1-octyl-1H-indol-3-yl) acetamide) MS-APCI: [M+1]$^+$393.5 (393.4); $\delta_H$ (CD3OD, 300 MHz): 0.91 (t, 3 H, J 12 Hz, CH3), 1.29-1.34 (m, 10 H, CH2), 1.88 (t, 2 H, J 12 Hz, CH2), 3.71 (s, 2 H, CH2), 3.87 (s, 3 H, CH3), 4.20 (t, 2 H, J 12 Hz, CH2), 6.87 (d, 1 H, J 6 Hz, ArH), 7.17-7.44 (m, 6 H, ArH), 7.82 (s, 1 H, ArH) $\delta_C$ (DMSO-d6; 75 MHz): 14.9, 15.7, 23.0, 27.3, 29.6, 29.7, 30.9, 32.2, 33.3, 46.5, 56.1; 109.9, 111.0, 112.6, 113.4, 118.3, 120.1, 121.4, 129.0, 129.1, 130.9, 131.8, 136.6, 144.4, 160.7, 174.2

J14 2-(1-octyl-5-phenyl-1H-indol-3-yl)acetamide MS-APCI: [M+1]$^+$ 363.6 (363.2); $\delta_H$ (CDCl3, 300 MHz): 0.85 (t, 3 H, J 15 Hz, CH3), 1.26-1.31 (m, 10 H, CH2), 1.84 (t, 2 H, J 12 Hz, CH2), 3.77 (s, 2 H, CH2), 4.10 (t, 2 H, J 15 Hz, CH2), 7.07 (d, 1 H, J 6 Hz, ArH), 7.30 (t, 1 H, J 12 Hz, ArH), 7.40-7.52 (m, 3 H, ArH), 7.63 (d, 1 H, J 6 Hz, ArH), 7.77 (s, 1 H, ArH). $\delta_C$ (CDCl3, 75 MHz): 14.1, 22.6, 27.0, 29.1, 29.1, 30.3, 31.7, 32.9, 46.5, 108.0, 110.0, 117.3, 121.9, 124.9, 126.5, 127.3, 127.3, 128.7, 128.7, 133.2, 136.0, 142.1, 174.3

J15 2-(1-octyl-1H-indol-3-yl)acetamide MS-APCI: [M+1]$^+$ 287.5 (287.4); $\delta_H$ (CDCl3, 300 MHz): 0.85 (t, 3 H, J 12 Hz, CH3), 1.25-1.31 (m, 10 H, CH2), 1.81 (t, 2 H, J 15 Hz, CH2), 3.73 (s, 2 H, CH2), 4.07 (t, 2 H, J 15 Hz, CH2), 7.06 (s, 1 H, ArH), 7.12 (t, 1 H, J 15 Hz, ArH), 7.22 (t, 1 H, J 12 Hz, ArH), 7.34 (d, 1 H, J 9 Hz, ArH), 7.57 (d, 1 H, J 6 Hz, ArH) $\delta_C$ (CDCl3, 75 MHz): 14.0, 22.6, 27.0, 29.1, 29.1, 30.2, 31.7, 32.9, 46.4, 107.6, 109.7, 118.9, 119.5, 122.0, 127.2, 127.4, 136.5, 174.3

J23 (2-(1-octyl-5-o-tolyl-1H-indol-3-yl)acetamide) MS-APCI: [M+1]$^+$ 377.3 (377.3); $\delta_H$ (CDCl3, 300 MHz): 0.85 (t, 3 H, J 15 Hz, CH3), 1.27-1.34 (m, 10 H, CH2), 1.85 (t, 2 H, J 15 Hz, CH2), 2.30 (s, 3 H, CH3), 3.72 (s, 2 H, CH2), 4.09 (t, 2 H, J 15 Hz, CH2), 7.12 (d, 1 H, J 9 Hz, ArH), 7.21-7.32 (m, 5 H, ArH), 7.37-7.48 (m, 3 H, ArH), 7.80 (s, 1 H, ArH) $\delta_C$ (CDCl3, 75 MHz): 14.1, 20.6, 22.6, 27.0, 29.1, 29.1, 30.3, 31.7, 32.9, 46.5, 107.7, 109.1, 119.2, 123.8, 125.7, 126.8, 127.3, 127.6, 130.3, 130.3, 133.5, 135.5, 135.6, 142.6, 174.3

J24 (2-(1-octyl-5-p-tolyl-1H-indol-3-yl)acetamide) MS-APCI: [M+1]$^+$ 377.3 (377.3); $\delta_H$ (CDCl3, 300 MHz): 0.85 (t, 3 H, J 15 Hz, CH3), 1.26-1.33 (m, 10 H, CH2), 1.83 (t, 2 H, J 12 Hz, CH2), 2.40 (s, 3 H, CH3), 3.76 (s, 2 H, CH2), 4.09 (t, 2 H, J 12 Hz, CH2), 7.07, (s, 1 H, ArH), 7.24 (d, 2 H, J 6 Hz, ArH), 7.38 (d, 1 H, J 6 Hz, ArH), 7.48-7.55 (m, 3 H, ArH), 7.75 (s, 1 H, ArH) $\delta_C$ (CDCl3, 75 MHz): 14.0, 21.0, 22.6, 27.0, 29.1, 29.1, 30.2, 31.7, 32.9, 46.5, 107.9, 109.9, 117.0, 121.8, 127.2, 127.2, 127.8, 129.4, 129.4, 133.2, 135.9, 136.2, 139.2, 174.3

Example 2

Synthesis of Compounds of Series 2, Table 2

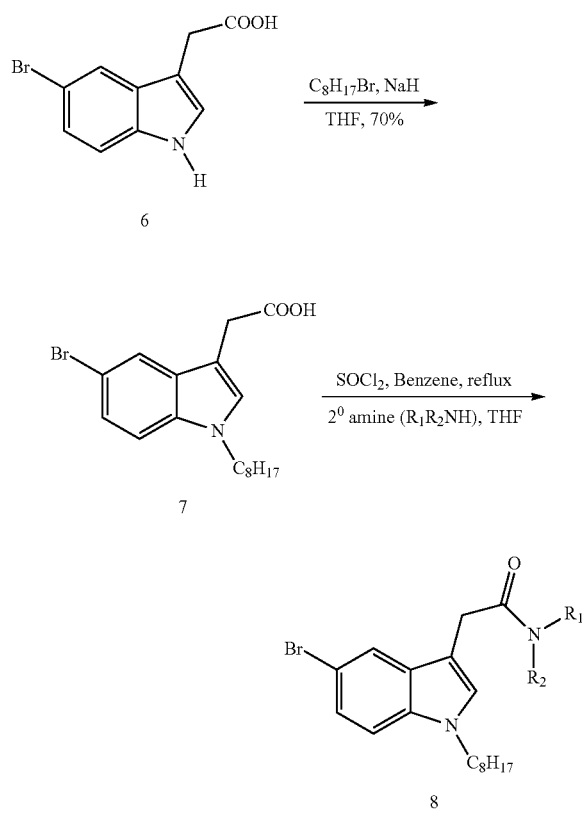

Scheme 2: Preparation of 3° amides (J1, J2, J4-6, J7, J11)

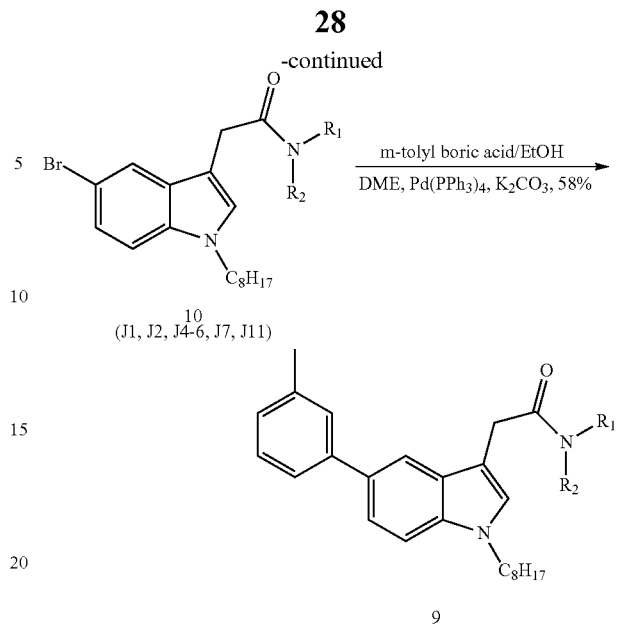

J10, J16, J21 and J22 were prepared following the experimental procedure Example 1, Scheme 2-(5-bromo-1-octyl-1H-indol-3-yl)acetic acid (7): To a stirred suspension of NaH (5.54 g, 138 mmol, 60% dispersion in mineral oil) in THF (100 mL THF) at 0° C. was added a solution of indole-3-acetic acid (6.65 g, 27.7 mmol) in THF (50 mL). After stirring the mixture for 30 min at 0° C., a solution of 1-Bromo Octane (14.3 mL, 83.1 mmol) in THF (50 mL) was added drop wise. The mixture was allowed to slowly reach room temp and continued to stir for 4 h. The reaction mixture was then cooled to 0° C. and excess hydride was carefully destroyed by slow addition of MeOH with vigorous stirring followed by cold water until a clear yellow solution resulted. Ether (100 mL) was added. The aqueous phase was separated, acidified with 6 N HCl, and extracted with sufficient dichloromethane 3 times. The combined dichloromethane extracts were dried (Na2SO4) and concentrated, purified by crystallisation in chloroform subsequently column chromatography using ethylacetate.

General Procedure for the Preparation of 3° Amides (8): A mixture of 2-(5-bromo-1-octyl-1H-indol-3-yl)acetic acid (6) (1 mmol) and SOCl2 (2 ml) in dry Benzene (5 ml) was refluxed for 4 hours then distilled out the excess of thionyl chloride and Benzene and dried in vacuum evaporated to dryness to give the corresponding acid chloride, which was dissolved in dry THF (4 ml). The THF solution was added dropwise to appropriate 2° amine in dry THF solution at 0-5° C. The reaction mixture was stirred at the same temperature for 1 hr; THF was removed under vacuum extracted with dichloromethane dried over Na2SO4 and evaporated to give the corresponding amide in nearly 80% in all cases.

General Procedure for the Preparation of Compound (9): To a solution of compound (7) (1 mmol, 1 eq.) in 4 ml DME was added Pd(PPh3)4 (0.05 eq) and the mixture was stirred under argon for 15 min. A solution of m-toly boric acid (1 mmol, 1 eq) in 1.5 ml EtOH (in case of J7 m-methoxy boric acid and) was added, the mixture was stirred for another 15 min, and then 2 M aqueous Na2CO3 (4 mL) was added. The resulting mixture was refluxed for 5 h under argon and cooled, and the organic solvent was removed under reduced pressure. The resulting suspension was extracted with CH2Cl2 and dried over Na2SO4, and the solvent was evaporated. The residue was chromatographed on silica gel eluted with Ethylacetate and n-hexane to yield the required compound nearly 60%.

J10 (2-(5-m-tolyl-1-(3-(trifluoromethyl)benzyl)-1H-indol-3-yl)acetamide) MS-APCI: [M+1]$^+$ 423.4 (423.3) $\delta_H$ (CDCl3, 300 MHz): 2.43 (s, 3 H, CH3), 3.79 (s, 2 H, CH2), 5.38 (s, 2 H, CH2), 7.13 (d, 2 H, J 9 Hz, ArH), 7.30 (t, 2 H, J 18 Hz, ArH), 7.41-7.50 (m, 5 H, ArH), 7.54 (d, 2 H, J 6 Hz, ArH) 7.79 (s, 1 H, ArH). $\delta_C$ (CDCl3, 75 MHz): 28.7, 37.8, 51.5, 100.3, 106.3, 110.5, 111.2, 112.0, 112.2, 114.4, 114.8, 115.0, 114.5, 116.1, 116.5, 119.7, 121.5, 123.0

J11 (N,N-diethyl-2-(5-m-tolyl-1-(3-(trifluoromethyl)benzyl)-1H-indol-3-yl)acetamide) MS-APCI: [M+1]$^+$ 479.5 (479.5) $\delta_H$ (CDCl3, 300 MHz): 1.10 (t, 6 H, J 15 Hz, CH3), 2.43, (s, 3 H, CH3), 3.34-3.45 (m, 4 H, CH2), 3.85 (s, 2 H, CH2), 5.34 (s, 2 H, CH2), 7.11-7.14 (m, 2 H, ArH), 7.25-7.27 (m, 2 H, ArH), 7.30 (t, 1 H, J 15 Hz, ArH), 7.40-7.45 (m, 5 H, ArH), 7.51 (d, 1 H, J 9 Hz, ArH), 7.80 (s, 1 H, ArH) $\delta_C$ (CDCl3, 75 MHz): 12.9, 14.4, 21.6, 30.8, 40.2, 42.5, 49.6, 109.7, 110.0, 117.4, 122.1, 123.4, 124.5, 126.9, 127.1, 128.2, 128.2, 128.5, 128.5, 129.4, 130.1, 133.4, 135.9, 138.2, 138.5, 142.3, 170.5

J16 (2-(5-m-tolyl-1H-indol-3-yl)acetamide) MS-APCI: [M+1]$^+$ 264.3 (265.2) $\delta_H$ (CDCl3, 300 MHz): 2.44 (s, 3 H, CH3), 3.79 (s, 2 H, CH2), 7.14 (d, 1 H, J 6 Hz, ArH), 7.20 (s, 1 H, ArH), 7.31 (t, 1 H, J 15 Hz, ArH), 7.43-7.52 (m, 4 H, ArH), 7.78 (s, 1 H, ArH), 8.25 (s, 1 H, ArNH) $\delta_C$ (CDCl3, 75 MHz): 21.5, 32.9, 109.7, 111.6, 117.1, 122.6, 124.2, 124.5, 127.3, 127.4, 128.1, 128.6, 134.0, 135.8, 138.3, 142.0, 174.1

J21 (2-(1-(3-methylbut-2-enyl)-5-m-tolyl-1H-indol-3-yl)acetamide) MS-APCI: [M+1]$^+$ 333.4 (333.3) $\delta_H$ (CDCl3, 300 MHz): 1.79 (s, 3 H, CH3), 1.84 (s, 3 H, CH3), 2.43 (s, 3 H, CH3), 3.75 (s, 2 H, CH2), 4.68 (d, 2 H, J 6 Hz, CH2), 5.37 (t, 1 H, J 15 Hz, CH), 7.05-7.15 (m, 2 H, ArH), 7.30-7.51 (m, 5 H, ArH), 7.75 (s, 1 H, ArH) $\delta_C$ (CDCl3, 75 MHz): 18.0, 21.6, 25.7, 33.0, 44.2, 108.0, 110.0, 117.3, 119.5, 121.9, 124.5, 127.2, 127.4, 128.0, 128.1, 128.6, 133.4, 136.0, 136.9, 138.3, 142.1, 174.4

J22 ((E)-2-(1-(3,7-dimethylocta-2,6-dienyl)-5-m-tolyl-1H-indol-3-yl)acetamide) MS-APCI: [M+1]$^+$ 401.5 (401.5) $\delta_H$(CDCl3, 300 MHz): 1.59 (s, 3 H, CH3), 1.66 (s, 3 H, CH3), 1.80 (s, 3 H, CH3), 2.10 (t, 4 H, J 21 Hz, CH2), 2.43 (s, 3 H, CH3), 3.65 (s, 2 H, CH2), 4.70 (d, 2 H, J 6 Hz, CH2), 5.04 (t, 1 H, J 9 Hz, CH), 5.39 (t, 1 H, J 6 Hz, CH), 7.05-7.15 (m, 2 H, ArH), 7.30-7.51 (m, 5 H, ArH), 7.75 (s, 1 H, ArH) (Ft (CDCl3, 75 MHz): 16.4, 17.7, 21.5, 25.7, 26.2, 32.9, 39.4, 44.1, 107.9, 110.1, 117.2, 119.3, 121.9, 123.6, 124.4, 127.2, 127.4, 128.1, 128.6, 131.9, 133.4, 136.0, 138.3, 140.4, 140.7, 142.8, 174.5

Example 3

Synthesis of Compounds of Series 3, Table 3

J1, J2 and J4-7 were prepared following the experimental procedure mentioned in Example 2, Scheme 2.

J1 (N,N-diethyl-2-(1-octyl-5-m-tolyl-1H-indol-3-yl)acetamide) MS-APCI: [M+1]$^+$ 433.3 (433.6) $\delta_H$ (CDCl3, 300 MHz): 0.89 (t, 3 H, J 12 Hz, CH3), 1.13-1.15 (m, 6 H, CH3), 1.26-1.30 (m, 10 H, CH2), 1.85 (t, 2 H, J 12 Hz, CH2), 2.44 (s, 3 H, CH3), 3.33-3.44 (m, 4 H, CH2), 3.84 (s, 2 H, CH2), 4.11 (t, 2 H, J 15 Hz, CH2), 7.08-7.14 (m, 2 H, ArH), 7.26-7.48 (m, 4 H, ArH), 7.78 (s, 1 H, ArH) $\delta_C$ (CDCl3, 75 MHz): 14.1, 14.3, 20.8, 21.6, 22.6, 27.0, 29.3, 29.4, 30.8, 31.8, 32.8, 40.1, 42.7, 46.4, 108.4, 109.6, 117.2, 121.4, 124.5, 126.7, 127.0, 128.1, 128.2, 128.5, 132.7, 135.7, 138.1, 142.6, 170.9

J2 (2-(1-octyl-5-m-tolyl-1H-indol-3-yl)-1-(piperidin-1-yl)ethanone) MS-APCI: [M+1]$^+$ 445.7 (445.6) $\delta_H$ (CD3OD, 300 MHz): 0.90 (t, 3 H, J 12 Hz, CH3), 1.26-1.29 (m, 10 H, CH2), 1.47-1.57 (m, 6 H, CH2), 1.84 (t, 2 H, J 12 Hz, CH2), 2.42 (s, 3 H, CH3), 3.51-3.58 (m, 4 H, CH2), 3.90 (s, 2 H, CH2), 4.18 (t, 2 H, J 15 Hz, CH2), 7.09-7.12 (m, 2 H, ArH), 7.32 (t, 1 H, J 15 Hz, ArH), 7.40-7.48 (m, 4 H, ArH), 7.85 (s, 1 H, ArH) $\delta_C$(CD3OD, 75 MHz): 13.6, 20.8, 22.8, 24.5, 25.9, 26.4, 27.1, 29.5, 29.6, 30.7, 31.6, 32.1, 43.3, 43.4, 46.2, 108.4, 110.0, 117.4, 121.5, 124.5, 127.1, 127.4, 128.0, 128.6, 128.7, 133.1, 136.6, 138.4, 143.0, 171.6

J4 (2-(1-octyl-5-m-tolyl-1H-indol-3-yl)-1-(pyrrolidin-1-yl)ethanone) MS-APCI: [M+1]$^+$ 431.4 (431.6): $\delta_H$ (CD3OD, 300 MHz): 0.91 (t, 3 H, J 15 Hz, CH3), 1.27-1.31 (m, 10 H, CH2), 1.84-1.96 (m, 6 H, CH2), 2.42 (s, 3 H, CH3), 3.49 (t, 2 H, J 15 Hz, CH2), 3.60 (t, 2 H, J 15 Hz, CH2), 3.84 (s, 2 H, CH2), 4.19 (t, 2 H, J 12 Hz, CH2), 7.09-7.15 (m, 2 H, ArH), 7.32 (t, 1 H, J 12 Hz, ArH), 7.40-7.48 (m, 4 H, ArH), 7.83 (s, 1 H, ArH) $\delta_C$(CD3OD, 75 MHz): 13.6, 20.8, 22.8, 24.5, 26.2, 27.1, 29.5, 30.6, 32.1, 32.5, 46.4, 50.2, 52.0, 107.8, 110.0, 117.5, 121.5, 124.5, 127.1, 127.7, 128.0, 128.7, 128.9, 133.1, 136.6, 138.4, 143.1, 172.0

J5 (N,N-dimethyl-2-(1-octyl-5-m-tolyl-1H-indol-3-yl)acetamide) MS-APCI: [M+1]$^+$ 405.4 (405.5): $\delta_H$ (CD3OD, 300 MHz): 0.91 (t, 3 H, J 12 Hz, CH3), 1.27-1.31 (m, 10 H, CH2), 1.86 (t, 2 H, J 9 Hz, CH2), 2.42 (s, 3 H, CH3), 3.10 (s, 6 H, CH3), 3.90 (s, 2 H, CH2), 4.18 (t, 2 H, J 15 Hz, CH2), 7.09-7.13 (m, 2 H, ArH), 7.29 (t, 1 H, ArH), 7.40-7.48 (m, 4 H, ArH), 7.83 (s, 1 H, ArH) $\delta_C$(CD3OD, 75 MHz): 13.6, 20.8, 22.8, 27.1, 29.5, 29.6, 30.6, 32.1, 32.5, 35.2, 37.6, 46.3, 107.8, 110.0, 117.5, 121.5, 124.5, 127.1, 127.7, 128.0, 128.7, 128.9, 133.0, 136.6, 138.4, 143.1, 172.0

J6 (2-(5-(3-ethoxyphenyl)-1-octyl-1H-indol-3-yl)-N,N-diethylacetamide) MS-APCI: [M+1]$^+$ 463.4 (463.6): $\delta_H$ (CD3OD, 300 MHz): 0.91 (t, 3 H, J 15 Hz, CH3), 1.05-1.15 (m, 6 H, CH3), 1.27-1.31 (m, 10 H, CH2), 1.46 (t, 3 H, J 15 Hz, CH3), 1.85 (t, 2 H, J 9 Hz, CH2), 3.38-3.49 (m, 4 H, CH2), 3.89 (s, 2 H, CH2), 4.09-4.19 (m, 4 H, CH2), 6.86 (d, 1 H, J 9 Hz, ArH), 7.14-7.43 (m, 6 H, ArH), 7.83 (s, 1 H, ArH) $\delta_C$ (CD3OD, 75 MHz): 12.5, 13.5, 13.6, 14.4, 22.8, 27.1, 29.5, 29.6, 30.6, 31.4, 32.1, 40.8, 43.2, 46.3, 63.7, 108.6, 110.0, 112.4, 113.7, 117.5, 119.8, 121.5, 127.6, 128.7, 129.8, 132.8, 136.7, 144.6, 169.9, 172.8

J7 (N,N-diethyl-2-(5-(3-methoxyphenyl)-1-octyl-1H-indol-3-yl)acetamide) MS-APCI: [M+1]$^+$ 449.5 (449.6) $\delta_H$ (CD3OD, 300 MHz): 0.90 (t, 3 H, J 12 Hz, CH3), 1.05-1.15 (m, 6 H, CH3), 1.27-1.31 (m, 10 H, CH2), 1.84 (t, 2 H, J 9 Hz, CH2), 3.40-3.48 (m, 4 H, CH2), 3.87 (s, 3 H, CH3), 3.88 (s, 2 H, CH2), 4.19 (t, 2 H, J 15 Hz, CH2), 6.87 (d, 1 H, J 6 Hz, ArH), 7.14-7.44 (m, 6 H, ArH), 7.83 (s, 1 H, ArH) $\delta_C$ (CD3OD, 75 MHz): 12.4, 13.5, 13.6, 15.7, 22.8, 27.1, 29.5, 29.6, 30.6, 31.4, 32.1, 40.8, 43.2, 46.3, 54.9, 108.6, 110.0, 111.8, 113.0, 117.5, 119.9, 121.5, 127.5, 128.7, 129.8, 132.8, 136.7, 144.6, 160.7, 172.7

J11 (N,N-diethyl-2-(5-m-tolyl-1-(3-(trifluoromethyl)benzyl)-1H-indol-3-yl)acetamide) (mentioned earlier in Series 2) MS-APCI: [M+1]$^+$ 479.5 (479.5) $\delta_H$ (CDCl3, 300 MHz): 1.10 (t, 6 H, J 15 Hz, CH3), 2.43, (s, 3 H, CH3), 3.34-3.45 (m, 4 H, CH2), 3.85 (s, 2 H, CH2), 5.34 (s, 2 H, CH2), 7.11-7.14 (m, 2 H, ArH), 7.25-7.27 (m, 2 H, ArH), 7.30 (t, 1 H, J 15 Hz, ArH), 7.40-7.45 (m, 5 H, ArH), 7.51 (d, 1 H, J 9 Hz, ArH), 7.80 (s, 1 H, ArH) $\delta_C$ (CDCl3, 75 MHz): 12.9, 14.4, 21.6, 30.8, 40.2, 42.5, 49.6, 109.7, 110.0, 117.4, 122.1, 123.4, 124.5, 126.9, 127.1, 128.2, 128.2, 128.5, 128.5, 129.4, 130.1, 133.4, 135.9, 138.2, 138.5, 142.3, 170.5

Example 4

Synthesis of Compounds of Series 4, Table 4

J3 1-octyl-5-m-tolyl-1H-indole. J3 was prepared by the method described for compound 26 in Example 5, Scheme 6.

MS-APCI: [M+1]⁺ 320.3 (320.4) δ$_H$ (CD3OD, 300 MHz): 0.91 (t, 3 H, J 18 Hz, CH3), 1.20-1.30 (m, 12 H, CH2), 1.85 (t, 2 H, J 15 Hz, CH2), 2.41 (s, 3 H, CH3), 4.17 (t, 2 H, J 12 Hz, CH2), 6.48 (d, 1 H, J 3 Hz, ArH), 7.10 (d, 1 H, J 6 Hz, ArH), 7.20 (d, 1 H, J 3 Hz, ArH), 7.31 (t, 1 H, J 15 Hz, ArH), 7.40-7.45 (m, 4 H, ArH), 7.76 (s, 1 H, ArH) δ$_C$ (CD3OD, 300 MHz): 13.6, 20.8, 22.8, 27.1, 29.4, 29.5, 30.6, 32.1, 46.4, 101.3, 109.8, 119.2, 121.1, 124.4, 127.0, 128.0, 128.7, 128.9, 129.8, 133.0, 136.2, 138.4, 143.2

Scheme 3: Preparation of homologated Cysmethynil (J20)

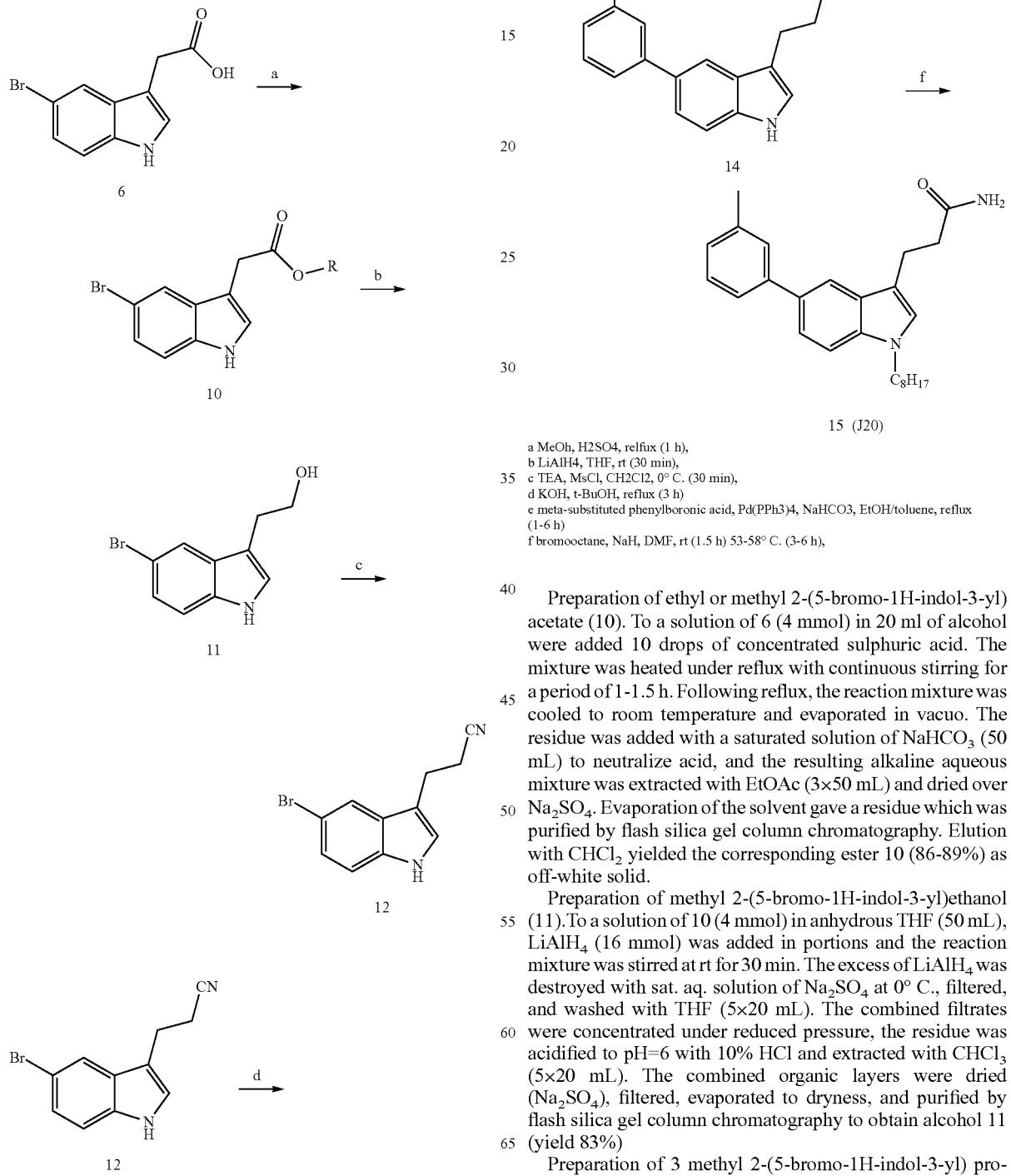

a MeOh, H2SO4, relfux (1 h),
b LiAlH4, THF, rt (30 min),
c TEA, MsCl, CH2Cl2, 0° C. (30 min),
d KOH, t-BuOH, reflux (3 h)
e meta-substituted phenylboronic acid, Pd(PPh3)4, NaHCO3, EtOH/toluene, reflux (1-6 h)
f bromooctane, NaH, DMF, rt (1.5 h) 53-58° C. (3-6 h), Preparation of ethyl or methyl 2-(5-bromo-1H-indol-3-yl) acetate (10). To a solution of 6 (4 mmol) in 20 ml of alcohol were added 10 drops of concentrated sulphuric acid. The mixture was heated under reflux with continuous stirring for a period of 1-1.5 h. Following reflux, the reaction mixture was cooled to room temperature and evaporated in vacuo. The residue was added with a saturated solution of NaHCO₃ (50 mL) to neutralize acid, and the resulting alkaline aqueous mixture was extracted with EtOAc (3×50 mL) and dried over Na₂SO₄. Evaporation of the solvent gave a residue which was purified by flash silica gel column chromatography. Elution with CHCl₂ yielded the corresponding ester 10 (86-89%) as off-white solid.

Preparation of methyl 2-(5-bromo-1H-indol-3-yl)ethanol (11).To a solution of 10 (4 mmol) in anhydrous THF (50 mL), LiAlH₄ (16 mmol) was added in portions and the reaction mixture was stirred at rt for 30 min. The excess of LiAlH₄ was destroyed with sat. aq. solution of Na₂SO₄ at 0° C., filtered, and washed with THF (5×20 mL). The combined filtrates were concentrated under reduced pressure, the residue was acidified to pH=6 with 10% HCl and extracted with CHCl₃ (5×20 mL). The combined organic layers were dried (Na₂SO₄), filtered, evaporated to dryness, and purified by flash silica gel column chromatography to obtain alcohol 11 (yield 83%)

Preparation of 3 methyl 2-(5-bromo-1H-indol-3-yl) propanenitrile (12). To a solution of alcohol 11 (0.76 g, 3.2 mmol), triethylamine (0.9 ml) in anhydrous $CH_2Cl_2$ (20 mL), mesyl chloride (0.55 mL) was added, and the reaction mixture was stirred at 0° C. for 30 min. under $N_2$. After dilution with glacial 5% NaOH solution (40 mL) the mixture was extracted with $CH_2Cl_2$ (3×40 mL). The combined organic layers were washed with water (10 mL), dried ($Na_2SO_4$), evaporated to dryness under reduced pressure, gives residue, The residue was dissolved in anhydrous DMSO (20 mL), KCN (0.21 g, 3.25 mmol) was added, and the reaction mixture was heated at 100° C. for 1 h. After dilution with ice-water (20 mL), the mixture was extracted with chloroform (4×30 mL), the combined organic layers were washed with water (2×10 mL), dried ($Na_2SO_4$), and evaporated to dryness under reduced pressure. And purified by flash silica gel column chromatography (100% $CHCl_3$) to obtain nitrile 12 (75%)

Preparation of methyl 2-(5-bromo-1H-indol-3-yl) propanamide (13). This compound prepared similar to 3. Yield: 82%

Preparation of 3-(5-m-tolyl-1H-indol-3-yl) propanamide (14): this compound was prepared by a similar method as 4.

Preparation of 3-(1-octyl-5-m-tolyl-1H-indol-3-yl) propanamide (15): this compound was prepared by a similar method as 5.

J20 (3-(1-octyl-5-m-tolyl-1H-indol-3-yl) propanamide) MS-APCI: $[M+1]^+$391.5 (391.3) $\delta_H$ (DMSO-d6, 300 MHz): 0.82 (t, 3 H, J 12 Hz, CH3), 1.22-1.30 (m, 10 H, CH2), 1.71 (t, 2 H, J 12 Hz, CH2), 2.39 (s, 3 H, CH3), 2.41 (t, 2 H, J 15 Hz, CH2), 2.92 (t, 2 H, J 15 Hz, CH2), 4.08, (t, 2 H, J 15 Hz, CH2), $\delta_C$ (CDCl3, 75 MHz): 14.1, 21.0, 21.6, 22.6, 27.0, 29.2, 29.2, 30.3, 31.8, 36.7, 46.3, 109.7, 113.6, 117.3, 121.4, 124.5, 126.1, 127.1, 128.0, 128.2, 128.6, 132.4, 135.9, 138.2, 142.6, 175.4

Scheme 4: Preparation of esters (J12 and J13)

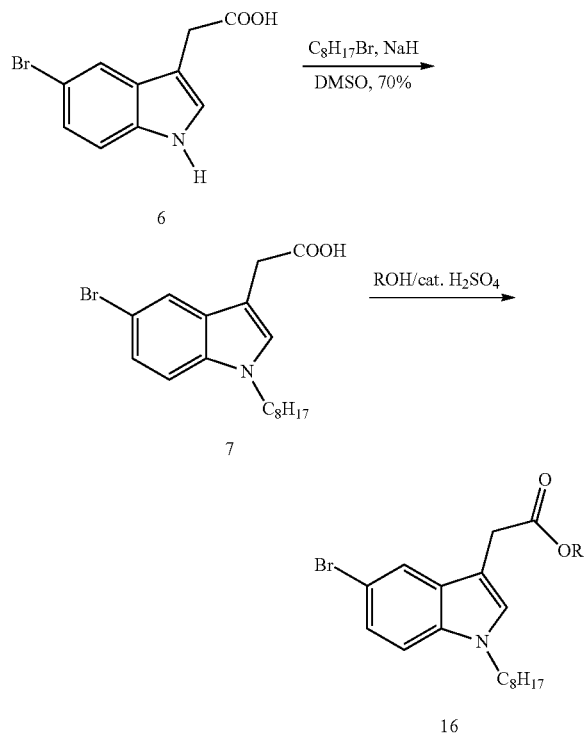

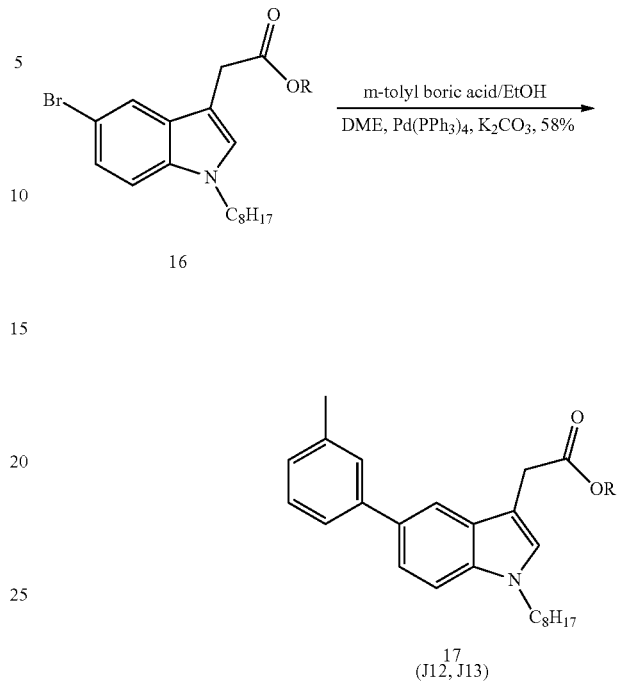

R = Me, Et

Preparation of ethyl or methyl 2-(5-bromo-1H-indol-3-yl) acetate (16): Synthetic procedure was similar to compound 10.

Preparation of Compound (17)

Compound 17 was prepared by a similar method as described for 26.

J12 (methyl 2-(1-octyl-5-m-tolyl-1H-indol-3-yl)acetate) MS-APCI: $[M+1]^+$392.5 (392.5) $\delta_H$ (CDCl3, 300 MHz): 0.85 (t, 3 H, J 12 Hz, CH3), 1.26-1.32 (m, 10 H, CH2), 1.82 (t, 2 H, J 6 Hz, CH2), 2.44 (s, 3 H, CH3), 3.70 (s, 2 H, CH2), 3.81 (s, 3 H, CH3), 4.06 (t, 2 H, J 15 Hz, CH2), 7.11 (d, 2 H, J 3 Hz, ArH), 7.32-7.37 (m, 2 H, ArH), 7.44 (d, 3 H, J 6 Hz, ArH), 7.78 (s, 1 H, ArH) $\delta_C$ (CDCl3, 75 MHz): 14.1, 21.6, 22.6, 27.0, 29.1, 29.2, 30.3, 31.1, 31.8, 46.5, 52.0, 107.0, 109.6, 117.5, 121.5, 124.5, 127.0, 127.3, 128.1, 128.2, 128.5, 132.8, 135.7, 138.1, 142.6, 172.6

J13 (ethyl 2-(1-octyl-5-m-tolyl-1H-indol-3-yl)acetate) MS-APCI: $[M+1]^+$406.5 (406.5) $\delta_H$ (CDCl3, 300 MHz): 0.85 (t, 3 H, J 12 Hz, CH3), 1.19-1.31 (m, 12 H, CH2), 1.82 (t, 2 H, J 6 Hz, CH2), 2.43 (s, 3 H, CH3), 3.79 (s, 2 H, CH2), 4.06 (t, 2 H, J 9 Hz, CH2), 4.13 (q, 2 H, J 21 Hz, CH2), 7.12 (d, 2 H, J 3 Hz, ArH), 7.32-7.36 (m, 2 H, ArH), 7.44 (d, 3 H, J 6 Hz, ArH), 7.79 (s, 1 H, ArH). $\delta_C$ (CDCl3, 75 MHz): 14.0, 14.2, 21.6, 22.6, 27.0, 29.1, 29.1, 30.3, 31.3, 31.7, 46.5, 60.7, 107.2, 109.6, 117.6, 121.4, 124.5, 127.0, 127.3, 128.2, 128.5, 128.7, 132.7, 135.7, 138.1, 142.6, 172.1

Scheme 5: Preparation of sulphonamides and reverse amides (J19G and J28G)

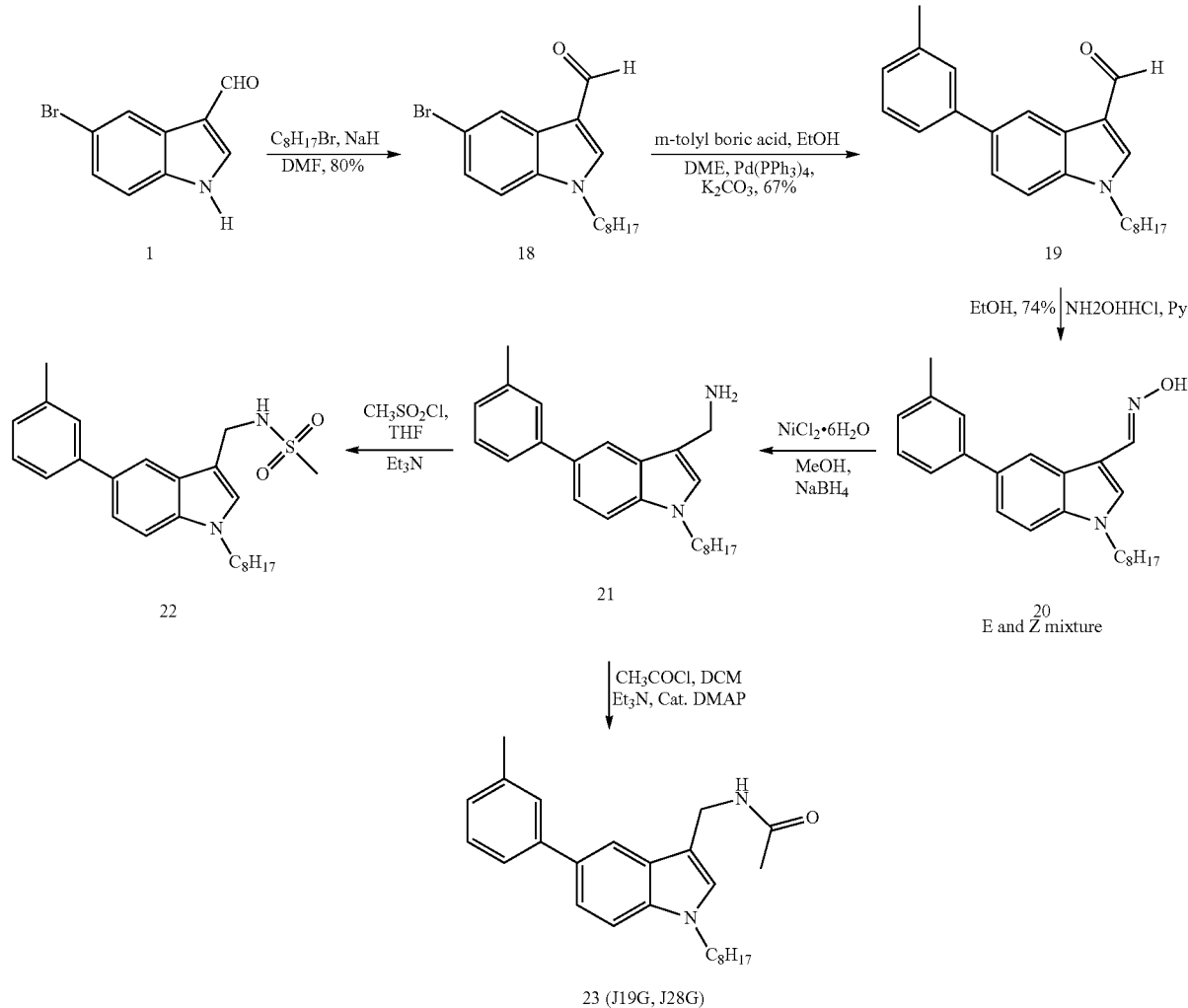

5-bromo-1-octyl-1H-indole-3-carbaldehyde (18): experimental procedure is similar to that of compound 25. Yields are quantitative.

1-octyl-5-m-tolyl-1H-indole-3-carbaldehyde (19): This compound was made by following the general procedure for Suzuki reaction. Similar to compound 26.

(E & Z)-1-octyl-5-m-tolyl-1H-indole-3-carbaldehyde oxime (20): 1-octyl-5-m-tolyl-1H-indole-3-carbaldehyde (1 eq., 1.03 mmol) was refluxed together with hydroxylamine hydrochloride (2.5 eq., 2.57 mmol) and pyridine (2.6 eq. 2.67 mmol) in ethanol (20 mL) until the formyl derivative disappeared from the reaction mixture (TLC), Reaction completed in 2 h. After being cooled to room temperature and diluting with water, the mixture was acidified with 10% HCl and extracted with diethyl ether. The combined organic extracts were washed successively with 10% HCl and water. After drying ($Na_2SO_4$), the organic extract was evaporated to a small volume under reduced pressure, triturated with petroleum ether and filtered to obtain the solid product (74%).

(1-octyl-5-m-tolyl-1H-indol-3-yl)methanamine (21/J18): To a solution of $NiCl_{2.6}H_2O$ (182 mg, 0.76 mmol) in methanol (12 ml) was added corresponding oxime 20 (280 mg 0.76 mmol) and $NaBH_4$ (174 mg, 4.16 mmol) was added in one portion with stirring. After 5 min the black precipitate was filtered off, filtrate concentrated in vacuum to approx. ⅓ of its original volume and poured into 20 ml of water containing 3 ml of ammonia solution. After extraction with ethyl acetate (three time), drying the extract with anhydrous. $Na_2SO_4$ and evaporation of the solvent, the crude amines 21 obtained as viscous, black oil. This crude product was used as it is further step without any purification.

N-((1-octyl-5-m-tolyl-1H-indol-3-yl)methyl)methanesulfonamide (22): Methanesulfonyl chloride (33 µl, 0.434 mmol) was added to a solution of (1-octyl-5-m-tolyl-1H-indol-3-yl)methanamine (152 mg, 0.434 mmol) and triethylamine (91 µl, 0.651 mmol) in THF (4 mL) at 0° C. The reaction mixture was allowed to stir at room temp for 60 min, the precipitate formed was filtered off, the filtrate was concentrated, and the residue was subjected to column chromatography (silica gel, $CH_2Cl_2$) to give sulphonamide 22 in 61% yield.

N-((1-octyl-5-m-tolyl-1H-indol-3-yl)methyl)acetamide (23): Acetyl chloride (44 µl, 0.434 mmol) was added to a solution of (1-octyl-5-m-tolyl-1H-indol-3-yl)methanamine (220 mg, 0.628 mmol) and triethylamine (131 µl, 0.651 mmol) in THF (4 mL) at 0° C. The reaction mixture was allowed to stir at room temp for 60 min, the precipitate formed was filtered off, the filtrate was concentrated, and the residue was subjected to column chromatography (silica gel, CH$_2$Cl$_2$) to give sulphonamide 23 in 65% yield.

J19G (N-((1-octyl-5-m-tolyl-1H-indol-3-yl)methyl)acetamide) MS-APCI: [M+1]$^+$ 391.1 (391.5); 7.71 (1H, s), 7.49-7.05 (6H, m), 7.01 (1H, s), 5.73 (1H, bs), 4.49 (2H, d, J4.8 Hz), 4.04 (2H, t, J 6.9 Hz), 2.43 (3H, s), 1.80 (2H, t, J 6.3 Hz), 1.95 (3H, s), 1.28-1.24 (10H, m), 0.86 (3H, t, J 7.2 Hz). δ$_C$ (CDCl3, 75 MHz) 169.9, 142.2, 138.2, 135.9, 133.0, 128.6, 128.1, 127.5, 127.1, 124.6, 124.4, 121.7, 117.3, 111.3, 109.8, 46.4, 35.1, 31.7, 30.3, 29.2, 29.1, 27.0, 23.1, 22.6, 21.5, 14.0.

J28G (N-((1-octyl-5-m-tolyl-1H-indol-3-yl)methyl)methanesulfonamide) MS-APCI: [M+1]$^+$ 427.3 (427.6); 7.19 (1H, s), 7.50-7.31 (7H, m), 7.15 (1H, s), 4.54 (2H, d, J 4.8 Hz), 4.10 (2H, t, J 7.2 Hz), 2.85 (3H, s), 2.44 (3H, s), 1.84 (2H, t, J 6.3 Hz), 1.31-1.25 (10H, m), 0.87 (3H, t, J 7.2 Hz). δ$_C$ (CDCl3, 75 MHz) 142.1, 138.2, 135.9, 133.3, 128.6, 128.1, 127.8, 127.26, 127.22, 124.4, 121.9, 117.1, 110.1, 109.9, 60.4, 46.5, 40.8, 38.8, 31.7, 30.2, 29.1, 26.9, 22.6, 21.5, 14.0.

Example 5

Synthesis of Compounds of Series 5, Table 5

Scheme 6: General experimental procedure for 3$^0$ amine (for compounds J25G-J27G, J29G-J32G, J34G-J41G)

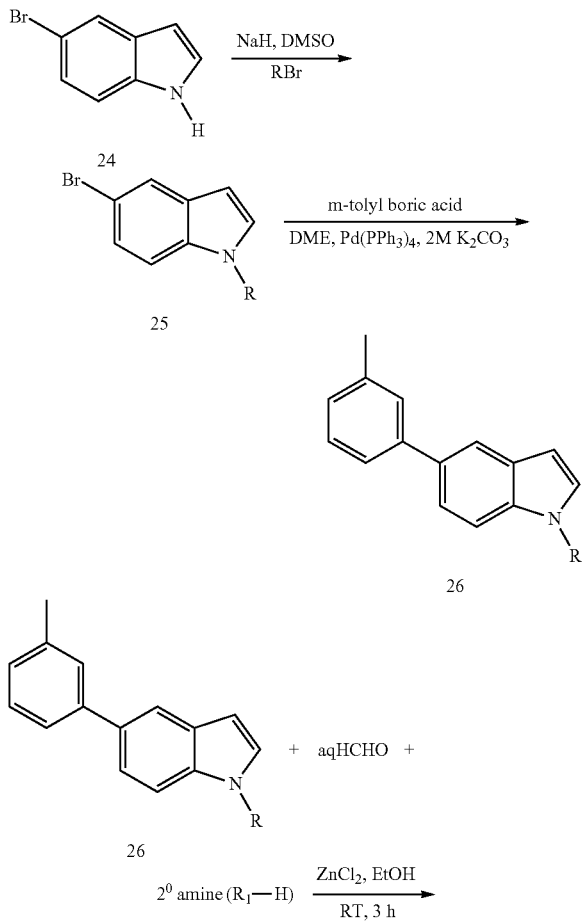

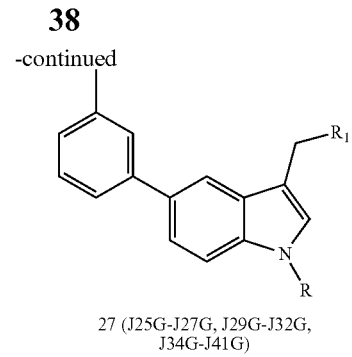

27 (J25G-J27G, J29G-J32G, J34G-J41G)

R = n-Octyl or isoprenyl

5-Bromo-1-alkyl-1H-indole (25): Sodium hydride (60% in dispersion, 1.2 eq.) was added to a solution of 5-bromoindole (1 eq) in anhydrous DMSO at room temperature (r.t.) with stirring. After 1 h stirring at the same temperature, 1-bromooctane (or Isoprenyl chloride) was added to the solution. The mixture was stirred at the same temperature for 3 h. After addition of water, the mixture was extracted with dichloromethane. The organic layer was washed with brine, dried over anhydrous Na$_2$SO$_4$ and evaporated under reduced pressure. The residue was chromatographed on a silica gel column using Ethyl acetate: n-hexane to give 25 in quantitative yield.

1-Alkyl-5-m-tolyl-1H-indole (26): To a solution of 5-bromo-1-alkyll-1H-indole (4 mmol, 1 eq.) in 15 ml DME was added Pd(PPh$_3$)$_4$ (0.2 mmol, 0.05 eq.) and the mixture was stirred under argon for 15 min. A solution of m-tolyl boric acid (4 mmol, 1 eq.) in 4 mml EtOH (in case of J36G and J37G o-tolyl boric acid and p-tolyl boric acid were added subsequently) was added, the mixture was stirred for another 15 min, and then 2M aqueous Na$_2$CO$_3$ (15 mL) was added. The resulting mixture was refluxed for 5 h under argon and cooled, and the organic solvent was removed under reduced pressure. The resulting suspension was extracted with CH$_2$Cl$_2$ and dried over Na$_2$SO$_4$, and the solvent was evaporated. The residue was chromatographed on silica gel eluted with Ethyl acetate and n-hexane to yield the 1-octyl-5-m-tolyl-1H-indole (~80%).

J18 (1-octyl-5-m-tolyl-1H-indol-3-yl)methanamine
The synthesis of J18 (also known as compound 21) was described in Scheme 5, under Series 4. MS-APCI: [M+1]$^+$ 348.3 (348.5) δ$_H$ (DMSO-d6, 300 MHz): 0.82 (t, 3 H, J=9 Hz, CH3), 1.22-1.30 (m, 10 H, CH2), 1.72 (t, 2 H, J=9 Hz, CH2), 2.39 (s, 3 H, CH3), 3.93 (s, 2 H, CH2), 4.12, (t, 2 H, J=12 Hz, CH2), 7.10-7.49 (m, 7H, ArH), 7.87 (s, 1H, ArH) δ$_H$ (DMSO-d6, 75 MHz): 14.0, 21.5, 22.6, 27.0, 29.1, 29.2, 30.3, 31.7, 46.4, 109.7, 117.2, 121.5, 124.4, 126.6, 127.1, 127.3, 128.1.

Preparation of Indole 3° Amines (27): In a round flask was charged with secondary amine (1 mmol, 1 eq), EtOH (3 mL), zinc chloride (1.5 mmol), formaldehyde (1 eq., 1 mmol, 36% aq.), and 1-octyl-5-m-tolyl-1H-indole (3). The mixture was stirred for a period of 10h (over night). After dilution with water, the mixture was basified with aq. 4M NaOH and extracted three times with ethyl acetate. Ethyl acetate was evaporated under reduced pressure. The residue was chromatographed quickly using Dichloromethane/Methanol or Ethyl acetate and n-hexane.

J17G (N-ethyl-N-((1-octyl-5-m-tolyl-1H-indol-3-yl)methyl)ethanamine) Yield 68% MS-APCI: [M]$^+$ 404.9 (404.6); δ$_H$ (CDCl3, 300 MHz) 7.88 (1H, s, ArH), 7.44-7.39 (3H, m, ArH), 7.30 (1H, s, ArH), 7.23 (1H, s, ArH), 7.09 (1H, d, J 6.9 Hz, ArH), 7.04 (1H, s), 4.06 (2H, t, J 7.2 Hz), 3.81 (2H, s), 2.56 (4H, q, J 6.9 Hz), 2.41 (3H, s), 1.81 (2H, t, J 6.9 Hz), 1.28-1.23 (10H, m), 1.08 (6H, t, J 7.2 Hz), 0.84 (3H, t, J 4.8 Hz). δ$_C$ (CDCl3, 75 MHz) 142.8, 138.0, 135.7, 132.4, 129.1, 128.5, 128.2, 127.7, 126.9, 124.5, 121.1, 118.1, 112.3, 109.4, 47.8, 46.6, 46.3, 31.7, 30.2, 29.2, 29.2, 27.0, 22.6, 21.6, 14.0, 12.1. Found (calcd. for C$_{28}$H$_{48}$N$_2$) C, 83.12 (83.11); H, 9.59 (9.96).

J25G (N,N-dimethyl(1-octyl-5-m-tolyl-1H-indol-3-yl)methanamine) Yield 61% MS-APCI: [M+1]$^+$ 377.3 (377.5); δ$_H$ (CDCl3, 300 MHz) 7.84 (1H, S), 7.46-7.42 (3H, m), 7.36 (1H,S), 7.32 (1H, d, J 4.5 Hz), 7.11 (1H, d, J 7.5 Hz), 7.07 (1H, s), 4.09 (2H, t, J 7.2 Hz), 3.66 (2H,s), 2.43 (3H,s), 2.29 (6H,s), 1.84 (2H, t, J 6.6 Hz), 1.31-1.25 (10H, m), 0.86 (3H,t, J 5.7 Hz). δ$_C$ (CDCl3, 75 MHz) 142.7, 138.0, 135.7, 132.6, 128.8, 128.4, 128.2, 127.9, 126.9, 125.5, 121.2, 117.8, 111.8, 109.4, 54.2, 46.3, 45.2, 31.7, 30.2, 29.1, 29.1, 26.9, 22.5, 21.5, 14.0

J26G (N-isopropyl-N-((1-octyl-5-m-tolyl-1H-indol-3-yl)methyl)propan-2-amine) Yield 62% MS-APCI: [M+1]$^+$ 433.0 (433.6) δ$_H$ (CDCl3, 300 MHz) 8.08 (1H, s), 7.46-7.30 (4H, m), 7.1 (2H, d, J 5.4 Hz), 7.01 (1H, s), 4.05 (2H, t, J 7.2 Hz), 3.85 (2H, s), 3.13 (2H, p, J 6.6 Hz), 2.41 (3H, s), 1.80 (2H, t, J 5.7 Hz), 1.28-1.24 (10H, m), 1.07 (12H, d, J 6.3 Hz), 0.86 (3H, t, J 6.9 Hz). δ$_C$ (CDCl3, 75 MHz) 142.9, 138.0, 136.1, 131.8, 128.5, 128.3, 128.1, 127.3, 126.7, 124.4, 120.9, 118.5, 115.7, 109.4, 47.3, 46.3, 40.4, 31.7, 30.2, 29.2, 29.2, 27.0, 22.6, 21.6, 20.6, 14.0.

J27G (N-((1-octyl-5-m-tolyl-1H-indol-3-yl)methyl)-N-propylpropan-1-amine) Yield 65% MS-APCI: [M]$^+$ 433.6 (433.6); δ$_H$ (CDCl3, 300 MHz) 7.90 (1H, s), 7.46-7.41 (3H, m), 7.33 (2H, d, J 8.4 Hz), 7.11 (1H, d, J 7.5 Hz), 7.02 (1H, s), 4.07 (2H, t, J 7.2 Hz), 3.79 (2H, s), 2.42 (3H, s), 2.42 (2H, t, J 4.2 Hz), 1.82 (2H, t, J 5.7 Hz), 1.54 (4H, q, J 7.5 Hz), 1.28-1.24 (10H, m), 0.87 (9H, t, J 7.2H). δ$_C$ (CDCl3, 75 MHz) 142.7, 138.0, 135.8, 132.2, 128.9, 128.4, 128.1, 127.6, 126.8, 124.4, 121.0, 118.2, 112.6, 109.3, 55.8, 49.2, 46.3, 31.7, 30.2, 29.1, 29.1, 27.0, 22.6, 21.5, 20.3, 14.0, 12.0.

J29G (N-methyl-N-((1-octyl-5-m-tolyl-1H-indol-3-yl)methyl)propan-2-amine) Yield 52% MS-APCI: [M+1]$^+$ 405.5 (405.6); δ$_H$ (CDCl3, 300 MHz) 7.87 (1H, s), 7.46-7.41 (3H, m), 7.32 (2H, d, J 8.4 Hz), 7.10 (1H, d, J 7.5 Hz), 7.07 (1H, s), 4.06 (2H, t, J 6.9 Hz), 3.76 (2H, s), 2.98 (1H, p, J 6.6 Hz), 2.42 (3H, s), 2.23 (3H, s), 1.81 (2H, t, J 6.3 Hz), 1.30-1.24 (10H, m), 1.11 (6H, d, J 6.6 HZ), 0.86 (3H, t, J 6.9 Hz). δ$_C$ (CDCl3, 75 MHz) 142.8, 138.0, 135.8, 132.5, 128.8, 128.5, 128.2, 127.8, 126.9, 124.5, 121.2, 117.9, 112.6, 109.5, 52.7, 48.3, 46.3, 36.8, 31.7, 30.3, 29.2, 29.2, 27.0, 22.6, 21.6, 18.0, 14.1.

J30G (3-((4-methylpiperazin-1-yl)methyl)-1-octyl-5-m-tolyl-1H-indole) Yield 87% MS-APCI: [M]$^+$ 432.6 (432.6); δ$_H$ (CDCl3, 300 MHz) 7.89 (1H, s), 7.46-7.41 (3H, m), 7.33-7.29 (2H, m), 7.05 (1H, s), 7.01 (1H, d, J 7.2 Hz), 4.04 (2H, t, J 6.9 Hz), 3.73 (2H, s), 2.54-2.47 (8H, m), 2.42 (3H, s), 2.25 (3H, s), 1.80 (2H, t, J 5.7 Hz), 1.28-1.24 (10 Hz, m), 0.86 (3H, t, J 5.4 Hz). δ$_C$ (CDCl3, 75 MHz) 142.7, 138.1, 135.8, 132.6, 129.0, 128.5, 128.2, 128.0, 126.9, 124.5, 121.3, 118.1, 111.2, 109.5, 55.2, 53.3, 53.0, 46.3, 46.0, 31.7, 30.2, 29.2, 27.0, 22.6, 21.6, 14.1.

J31G (1-octyl-3-(pyrrolidin-1-ylmethyl)-5-m-tolyl-1H-indole) Yield 71% MS-APCI: [M+1]$^+$ 403.5 (403.6); δ$_H$ (CDCl3, 300 MHz) 7.85 (1H, s), 7.46-7.41 (3H, m), 7.32 (2H, d, J 8.1 Hz), 7.10 (1H, s), 7.01 (1H, d, J 7.2 Hz), 4.04 (2H, t, J 7.2 Hz), 3.87 (2H, s), 2.61 (4H, bs), 2.42 (3H, s), 1.78 (6H, bs), 1.29-1.24 (10H, m), 0.86 (3H, t, J 6.3 Hz). δ$_C$ (CDCl3, 75 MHz) 142.9, 138.1, 135.6, 132.6, 128.7, 128.5, 128.2, 127.9, 127.0, 124.6, 121.2, 117.7, 112.0, 109.5, 54.0, 50.1, 46.4, 31.8, 30.3, 29.26, 29.22, 27.0, 23.5, 22.6, 21.6, 14.1.

J32G (1-octyl-3-(piperidin-1-ylmethyl)-5-m-tolyl-1H-indole) Yield 78% MS-APCI: [M+H]$^+$417.5 (417.6); δ$_H$ (CDCl3, 300 MHz) 7.87 (1H, s), 7.46-7.41 (3H, m), 7.34-7.32 (2H, m), 7.11 (1H, d, J 7.2 Hz), 7.07 (1H, s), 4.06 (2H, t, J 6.9 Hz), 3.72 (2H, s), 2.45 (3H, s), 2.46-2.43 (4H, m), 1.84 (2H, t, J 6.3 Hz), 1.58-1.55 (4H, m), 1.41-1.22 (12H, m), 0.86 (3H, t, J 6.9 Hz). δ$_C$ (CDCl3, 75 MHz) 142.8, 138.1, 135.6, 132.5, 129.2, 128.5, 128.28, 128.21, 126.9, 124.5, 121.8, 118.0, 111.2, 109.4, 60.3, 54.3, 53.8, 46.3, 31.7, 30.2, 29.1, 27.0, 26.0, 24.4, 22.6, 21.6, 14.1.

J34G (3-(morpholinomethyl)-1-octyl-5-m-tolyl-1H-indole) MS-APCI: [M]$^+$419.3 (419.6); δ$_H$ (CDCl3, 300 MHz) 7.90 (1H, s), 7.46 (3H, m), 7.33-7.28 (2H, m), 7.09 (1H, d, J 7.5 Hz), 7.01 (1H, s), 4.01 (2H, t, J 6.9 Hz), 3.69 (2H, s), 3.68 (4H, t, J 4.8 Hz), 2.48 (4H, t, J 4.8 Hz), 2.41 (3H, s), 1.78 (2H, t, J 6 Hz), 1.27-1.21 (10H,m), 0.86 (3H, t, J 6.9 Hz). δ$_C$ (CDCl3, 75 MHz) 142.8, 138.1, 135.9, 132.7, 129.0, 128.6, 128.3, 128.1, 127.1, 124.6, 121.4, 118.2, 110.9, 109.6, 67.2, 54.0, 53.7, 46.4, 31.8, 30.3, 29.2, 29.2, 27.0, 22.7, 21.7, 14.2.

Example 6

Synthesis of Compounds of Series 6, Table 6

J17G and J35-J41G were prepared similar to the experimental procedure mentioned in Example 5, Scheme 6.

J17G (N-ethyl-N-((1-octyl-5-m-tolyl-1H-indol-3-yl)methyl) ethanamine) Yield 68% MS-APCI: [M]$^+$ 404.9 (404.6); δ$_H$ (CDCl3, 300 MHz) 7.88 (1H, s, ArH), 7.44-7.39 (3H, m, ArH), 7.30 (1H, s, ArH), 7.23 (1H, s, ArH), 7.09 (1H, d, J 6.9 Hz, ArH), 7.04 (1H, s), 4.06 (2H, t, J 7.2 Hz), 3.81 (2H, s), 2.56 (4H, q, J 6.9 Hz), 2.41 (3H, s), 1.81 (2H, t, J 6.9 Hz), 1.28-1.23 (10H, m), 1.08 (6H, t, J 7.2 Hz), 0.84 (3H, t, J 4.8 Hz). δ$_C$ (CDCl3, 75 MHz) 142.8, 138.0, 135.7, 132.4, 129.1, 128.5, 128.2, 127.7, 126.9, 124.5, 121.1, 118.1, 112.3, 109.4, 47.8, 46.6, 46.3, 31.7, 30.2, 29.2, 29.2, 27.0, 22.6, 21.6, 14.0, 12.1. Found (calcd. for C$_{28}$H$_{48}$N$_2$) C, 83.12 (83.11); H, 9.59 (9.96).

J35G (N-ethyl-N-41-(3-methylbut-2-enyl)-1H-indol-3-yl)methyl)ethanamine) MS-APCI: [M+1]$^+$ 271.5 (271.4); δ$_H$ (CDCl3, 300 MHz) 7.69 (1H, d, J 7.5 Hz), 7.28 (1H, d, J 8.1 Hz), 7.18 (1H, t, J 6.9 Hz), 7.10 (1H, d, J 7.2 Hz), 7.04 (1H, s), 5.36 (1H, t, J 6.6 Hz), 4.64 (2 Hz d, J 6.6 Hz), 3.77 (2H, s), 2.56 (4H, q, J 6 Hz), 2.40 (3H, s), 1.74 (3H, s), 1.08 (6H, t, J 7.2 Hz). δ$_C$ (CDCl3, 75 MHz) 136.1, 135.9, 128.8, 126.8, 121.2, 120.1, 119.4, 118.8, 111.6, 109.3, 47.8, 46.5, 44.0, 40.9, 25.6, 18.0, 11.8.

J36G (N-ethyl-N-((1-octyl-5-o-tolyl-1H-indol-3-yl)methyl)ethanamine) Yield 72% MS-APCI: [M+H]$^+$405.7 (405.6); δ$_H$ (CDCl3, 300 MHz) 7.63 (1H, s, ArH), 7.33-7.22 95H, m, ArH), 7.16 (1H, d, J 8.4 Hz, ArH), 7.08 (1H, s), 4.09 (2H, t, J 7.2 Hz), 7.39 (2H, s), 2.56 (4H, q, J 7.2 Hz), 2.32 (3H, s), 1.85 (2H, t, J 6.9 Hz), 1.32-1.26 (10H, m), 1.08 (6H, t, J 7.2 Hz), 0.87 (3H, t, J 4.8 Hz). δ$_C$ (CDCl3, 75 MHz) 143.2, 135.7, 135.2, 132.6, 130.3, 130.1, 128.4, 127.7, 126.5, 125.5, 122.9, 119.9, 111.5, 108.7, 47.7, 46.5, 46.3, 31.7, 30.2, 29.1, 29.1, 27.0, 22.6, 20.7, 14.0, 11.9. Found (calcd. for C$_{28}$H$_{48}$N$_2$) C, 83.01 (83.11); H, 9.21 (9.96).

J37G (N-ethyl-N-((1-octyl-5-p-tolyl-1H-indol-3-yl)methyl) ethanamine) Yield 65% MS-APCI: [M+H]$^+$405.3 (405.6); δ$_H$ (CDCl3, 300 MHz) 7.87 (1H, s), 7.55 (2H, d, J 7.8 Hz), 7.42 (2H, d, J 8.1 Hz), 7.33 (1H, d, J 8.4 Hz), 7.24 (2H, d, J 7.8 Hz), 7.06 (1H, s), 4.08 (2H, t, J 6.9 Hz), 3.81 (2H, s), 2.54 (4H, q, J 6.9 Hz), 2.39 (3H, s), 1.83 (2H, t, J 6.6 Hz), 1.31-1.29 (10H,m), 1.10 (6H, t, J 7.2 Hz), 0.86 (3H,t,J 6.9 Hz). δ$_C$ (CDCl3, 75 MHz) 139.9, 135.7, 135.5 132.2, 129.3, 129.0, 127.8, 127.2, 121.0, 117.7, 111.8, 109.4, 47.7, 46.8, 46.3, 31.7, 30.2, 29.1, 29.1, 26.9, 22.5, 21.0, 14.0, 11.9.

J38G (N-ethyl-N-((1-(3-methylbut-2-enyl)-5-m-tolyl-1H-indol-3-yl)methyl)ethanamine) MS-APCI: [M+1]$^+$ 361.1 (361.5); $\delta_H$ (CDCl3, 300 MHz) 7.88 (1H, s), 7.46-7.41 (3H, m), 7.34-7.29 (2H, m), 7.11 (1H, d, J 7.2 Hz), 7.06 (1H, s), 5.38 (1H, t, J 6.9 Hz), 4.67 (2H, d, J 6.6 Hz), 3.80 (2H, s), 2.57 (4H, q, J 6.9 Hz), 2.43 (3H, s), 1.82 (3H, s), 1.76 (3H, s), 1.09 (6H, t, J 7.2 Hz). $\delta_C$ (CDCl3, 75 MHz) 142.7, 138.1, 136.1, 135.6, 132.6, 129.2, 128.5, 128.2, 127.7, 126.9, 124.5, 121.2, 119.9, 117.8, 111.6, 109.6, 47.7, 46.5, 44.1, 25.6, 21.6, 18.0, 11.7. C 82.92% (83.28) H 8.85 (8.95)

J39G (1-(3-methylbut-2-enyl)-3-(piperidin-1-ylmethyl)-5-m-tolyl-1H-indole) Yield 71% MS-APCI: [M+1]$^+$ 373.3 (373.5); $\delta_H$ (CDCl3, 300 MHz) 7.86 (1H,s), 7.46-7.42 (3H, m), 7.34 (2H,d, J 7.2 Hz), 7.12 (1H, d, J 10.2 Hz), 7.03 (1H, s), 5.39 (1H, t, J 5.1 Hz), 4.68 (2H,d,J 6.6 Hz), 3.73 (2H,s), 2.49 (4H,bs), 2.44 (3H,s), 1.83 (3H, s), 1.77 (3H,s), 1.42 (2H, m), 0.86 (4H, m). $\delta_C$ (CDCl3, 75 MHz) 142.8, 138.1, 136.1, 135.6, 132.6, 129.4, 128.5, 128.2, 127.8, 126.9, 124.5, 121.1, 120.0, 118.0, 111.4, 109.5, 54.3, 53.8, 44.1, 26.0, 25.6, 24.4, 21.6, 18.0.

J40G (N-ethyl-N-((5-fluoro-1-octyl-1H-indol-3-yl)methyl)ethanamine) MS-APCI: [M+1]$^+$ 330.0 (333.4); $\delta_H$ (CDCl3, 300 MHz) 7.35 (1H, dd, $J_1$ 10.5 Hz, $J_2$=0.9 Hz), 7.18 (1H, dd, $J_1$ 9 Hz, $J_2$=4.2 Hz), 7.05 (1H,s), 6.91 (1H, dt, $J_1$ 9 Hz, $J_2$ 2.4 Hz), 4.03 (2H, t, J 6.9 Hz), 3.70 (2H, s), 2.53 (4H, q, J 6.9 Hz), 1.79 (2H, t, J 6.9 Hz), 1.28-1.24 (10H, m), 1.07 (6H, t, J 7.2 Hz), 0.86 (3H, t, J 6.3 Hz). $\delta_C$ (CDCl3, 75 MHz) 159.0, 155.9, 132.8, 128.6, 111.9, 109.7, 109.3, 104.6, 47.9, 46.5, 46.4, 31.7, 30.1, 29.1, 29.1, 26.9, 22.5, 14.0, 11.8. C 75.68% (75.86) H 9.85% (10.00)

J41G (N-ethyl-N-((5-fluoro-1-(3-methylbut-2-enyl)-1H-indol-3-yl)methyl)ethanamine) MS-APCI: [M+1]$^+$ 289.0 (289.4); $\delta_H$ (CDCl3, 300 MHz) 7.34 (1H,dd, $J_1$ 9.6 Hz, $J_2$ 2.1 Hz), 7.17 (1H, d, J 3.6 Hz), 7.09 (1H, s), 6.91 (1H, dd, $J_1$ 8.7 Hz, $J_2$ 4.2 Hz), 5.34 (1H, t, J 6.6 Hz), 4.64 (2H, d, J 6.9 Hz), 3.84 (2H, s), 2.66 (4H,q, J 7.2 Hz), 1.81 (3H,s), 1.76 (3H,s), 1.16 (6H, t, J 6.9 Hz). $\delta_C$ (CDCl3, 75 MHz) 159.1, 156.0, 136.3, 132.8, 128.4, 119.7, 111.6, 111.5, 110.0, 109.8, 109.7, 109.4, 104.5, 104.2, 47.9, 46.4, 44.3, 25.6, 17.9, 11.7.

Example 7

Biological Evaluation

Measurement of ICMT activity. Icmt activity was determined by following incorporation of $^3$H from [$^3$H]AdoMet (Amersham Biosciences) into the small molecule substrate biotin-S-farnesyl L-cysteine (BFC). Inhibitors were first incubated at 37° C. for 20 min, with the Sf9 membranes containing ICMT. An assay mixture containing 4 μM BFC and 5 μM [$^3$H]AdoMet in 100 mM Hepes, pH 7.4 and 5 mM MgCl$_2$ was added to initiate the reaction. Reactions were carried out at 37° C. for 20 min, and terminated by addition of 10% Tween 20 and streptavidin beads (GE Healthcare, 10 uL of packed beads suspended in 500 μL of 20 mM NaH$_2$PO$_4$, pH 7.4, containing 150 mM NaCl). The mixtures were mixed by gentle agitation overnight at 4° C. The beads were harvested by centrifugation in a tabletop microcentrifuge at 10,000 rpm for 5 min and washed three times with 500 μL of 20 mM NaH$_2$PO$_4$, pH 7.4, containing 150 mM NaCl. The beads were then suspended in the same buffer, transferred to scintillation vials, and radioactivity determined.

Cell Culture and Proliferation Assays. The MDA-MB-231 human breast cells were maintained at 37° C. with 5% CO$_2$ in DMEM (Sigma) supplemented with 10% fetal bovine serum (FBS, Hyclone), 50 U/ml penicillin (Gibco), and 50 μg/ml streptomycin (Gibco). For proliferation assays, cells were seeded at 20% confluency in DMEM containing 5% FBS in 96-well plates for 24 h prior to treatment with specific agents (e.g. cysmethynil) or vehicle at various concentrations for 72 h. The relative number of the live cells was determined using the CellTiter® 96 AQueous One Solution Cell Proliferation Assay (Promega). Each condition was performed in triplicate, and data presented represent that obtained from at least two separate experiments.

Example 8

Synthesis of amine analogs of 1-(5-fluoro-1-octyl-1H-indol-3-yl)-N,N-diethylmethanamine (6-9)

Six analogs of 1-(5-fluoro-1-octyl-1H-indol-3-yl)-N,N-diethylmethanamine were synthesized by the reactions shown in Scheme 7. The structure of 1-(5-fluoro-1-octyl-1H-indol-3-yl)-N,N-diethylmethanamine (6-9) and its analogues are illustrated in Table 7 below.

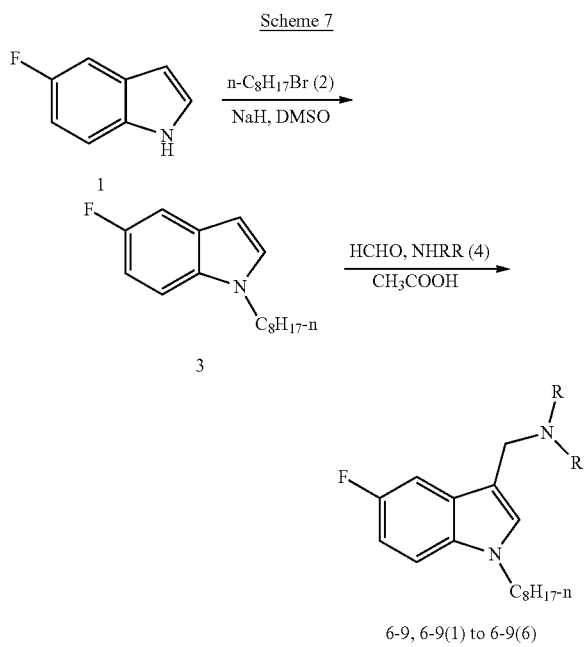

TABLE 7

Structures of 6-9 and its analogs 6-9(1) to 6-9(6)

| Entry | *—NRR |
|---|---|
| 6-9(1) | *—N(CH$_3$)$_2$ |
| 6-9 | *—N(Et)$_2$ |
| 6-9(2) | *—N(piperidine) |

TABLE 7-continued

Structures of 6-9 and its analogs 6-9(1) to 6-9(6)

| Entry | *—NRR |
|---|---|
| 6-9(3) | *—N(CH2CH2)2S (thiomorpholine) |
| 6-9(4) | *—N(CH2CH2)2O (morpholine) |
| 6-9(5) | *—N pyrrolidine |
| 6-9(6) | *—N(CH2CH2)2N—CH3 (N-methylpiperazine) |
| 6-9(7) | *—N(CH3)(CH2CH2CH3) |
| 6-9(8) | *—N(CH2CH3)(CH2CH2CH3) |
| 6-9(9) | *—N(CH2CH2CH2CH3)2 |

Experimental Section

Reagents were purchased from Sigma-Aldrich Chemical Company Inc or Alfa Aesar and used without further purification. $^1$H NMR (300 MHz) and $^{13}$C NMR (75 MHz) spectra were measured on a Bruker Spectrospin 300 Ultrashield magnetic resonance spectrometer using $CDCl_3$ as the solvent. Chemical shifts (δ) were reported in ppm and referenced to residual deuterated solvents. Coupling constants (J) were reported in Hz. Reactions were monitored by thin layer chromatography (TLC, Silica Gel 60 F254, Merck) with ultraviolet light as visualizing agent. Column chromatography was carried out with Silica Gel 60 (0.04-0.06 mm). Mass spectra were recorded in positive ion mode using electro spray ionization (ESI) or high-resolution LC-MS (IT TOF). Elemental analysis had carbon and hydrogen values that were within ±5% of theoretical values.

General Procedure for the Synthesis of 5-fluoro-1-octyl-1H-indole (3)

The procedure for the synthesis of compound 3 mentioned in Scheme 7 can be carried out as described in Na, Y. M.; Le Borgne, M.; Pagniez, F.; Le Baut, G.; Le Pape, P., *Eur. J. Med. Chem.* 2003, 38, 75-87. Semi-automatic high-throughput determination of plasma protein binding using a 96-well plate filtrate assembly and fast liquid chromatography—tandem mass spectrometry.

To the solution of 5-fluore-1H-indole (1, 5 mmol, 1 equiv.) in anhydrous dimethylsulfoxide (DMSO) was added NaH (60% in mineral oil dispersion, 6 mmol, 1.2 equiv.) at room temperature. The mixture was stirred for about 1 h at the same temperature, then 1-bromooctane (2, 6 mmol, 1.2 equiv.) was added and the mixture was stirred for 4 h. Water was added to stop the reaction. The mixture was extracted by dichloromethane and the organic layer was washed with brine, dried ($Na_2SO_4$), filtered, and evaporated. The residue was purified by column chromatography of silica gel to get yellow oil. Yield: 85.0%. $^1$H NMR (300 MHz, $CDCl_3$): δ0.85 (t, J=6.9 Hz, 3 H), 1.23-1.27 (m, 10 H), 1.79 (t, J=6.9 Hz, 2 H), 4.06 (t, J=6.9 Hz, 2 H), 6.41 (d, J=2.7 Hz, 1 H), 6.88-6.95 (m, 1H), 7.10 (d, J=2.7 Hz, 1 H), 7.09-7.25 (m, 2H). $^{13}$C NMR (75 MHz, $CDCl_3$) δ 14.0, 22.5, 26.9, 29.1 (2C), 30.2, 31.7, 46.6, 100.7, 105.4, 109.4, 109.8, 128.6, 129.2, 132.5, 157.6. IT TOF-HRMS calculated for ($C_{16}H_{22}FN+H^+$) 248.1814. found 248.1720.

General Procedure for the Synthesis of N-substituted (1-octyl-1H-indol-3-yl)methyl) amine (6-9, 6-9(1) to 6-9(9)

The procedure for the synthesis of N-substituted (1-octyl-1H-indol-3-yl)methyl) amine can be carried out as described in Brehm, W. J.; Lindwall, H. G. The preparation of Mannich bases related to gramine. *J. Org. Chem.* 1950, 15, 685-687.

To the mixture of appropriate secondary amine (4, 0.97 mmol, 1.2 equiv.), 36% aqueous formaldehyde (0.97 mmol, 1.2 equiv.) in acetic acid (5 mL) was added 5-fluoro-1-octyl-1H-indole (3, 200 mg, 1 equiv.) 0° C. The reaction mixture was stirred at room temperature overnight. After the reaction was completed, the reaction mixture was basified by 50% NaOH aqueous solution to pH=9 and extracted by dichloromethane (10 mL×3). The combined extracts were washed with brine (20 mL) and dried over $Na_2SO_4$. The organic layer was concentrated under reduced pressure. The crude product was purified by column chromatography of silica gel using or ethyl acetate/hexane or dichloromethane/methanol as eluent solvent.

1-(5-fluoro-1-octyl-1H-indol-3-yl)-N,N-dimethylmethanamine 6-9(1). Yellow oil. Yield: 71.1%. $^1$H NMR (300 MHz, $CDCl_3$): δ 0.86 (br, 3 H), 1.25-1.28 (m, 10 H), 1.81 (br, 2 H), 2.28 (s, 6 H), 3.58 (s, 2 H), 4.05 (t, J=6.9 Hz, 2 H), 6.90-6.96 (m, 1 H), 7.10 (s, 1H), 7.16-7.22 (m, 1 H), 7.30 (d, J=9.3 Hz, 1H). $^{13}$C NMR (75 MHz, $CDCl_3$) δ 14.0, 22.5, 29.1 (2C), 30.1, 31.5, 31.7, 45.0 (2C), 46.5, 54.2, 103.9, 109.8, 111.0, 128.5, 129.0, 132.8, 141.9, 161.0. IT TOF-HRMS calculated for ($C_{19}H_{30}FN_2+H^+$) 305.2393. found 305.2282. Elemental analysis: calc./found (C, H): 74.96; 9.60; 74.73; 9.31.

N-ethyl-N-((5-fluoro-1-octyl-1H-indol-3-yl)methyl)ethanamine 6-9 . Yellow oil. Yield: 46.1%. $^1$H NMR (300 MHz, $CDCl_3$): δ 0.86 (t, J=6.6 Hz, 3 H), 1.10 (t, J=6.9 Hz, 6 H), 1.28 (br, 10 H), 1.80 (br, 2 H), 2.57 (q, J=6.9 Hz, 4 H), 3.74 (s, 2 H), 4.04 (t, J=6.9 Hz, 2 H), 6.93 (t, J=9.0 Hz, 1 H), 7.11 (s, 1H), 7.17-7.22 (m, 1H), 7.34 (d, J=9.6 Hz, 1H). $^{13}$C NMR (75 MHz, $CDCl_3$) δ 11.7 (2C), 14.0, 22.5, 26.9, 29.1 (2C), 30.1, 31.7, 46.4 (2C), 47.8, 104.4, 109.4, 109.9, 111.2, 128.9, 132.8, 155.9, 159.0. IT TOF-HRMS calculated for ($C_{21}H_{34}FN_2+H^+$) 333.2706. found 333.2616. Elemental analysis: calc./found (C, H): 75.86; 10.00; 75.99; 9.83.

5-fluoro-1-octyl-3-(piperidin-1-ylmethyl)-1H-indole 6-9(2). Yellow oil. Yield: 75.8%. $^1$H NMR (300 MHz, $CDCl_3$): δ 0.86 (t, J=6.9 Hz, 3 H), 1.24-1.28 (m, 10 H), 1.42 (d, J=4.5 Hz, 2 H), 1.59 (t, J=5.4 Hz, 4 H), 1.80 (br, 2 H), 2.45 (br, 4 H), 3.65 (s, 2 H), 4.04 (t, J=7.2 Hz, 2 H), 6.93 (t, J=8.1 Hz, 1 H), 7.11 (s, 1H), 7.17-7.22 (m, 1H), 7.35 (d, J=1.5 Hz, 1H). $^{13}$C NMR (75 MHz, $CDCl_3$) δ 11.7 (2C), 14.0, 22.5, 24.2, 25.8 (2C), 26.9, 29.1 (2C), 30.1, 31.7, 46.5, 53.8, 54.1 (2C), 104.4, 109.7, 109.9, 110.5, 129.0, 132.7, 155.9, 159.1. IT TOF-HRMS calculated for ($C_{22}H_{34}FN_2+H^+$) 345.2706. found 345.2620. Elemental analysis: calc./found (C, H): 76.70; 9.65; 76.43; 9.42.

4-((5-fluoro-1-octyl-1H-indol-3-yl)methyl)thiomorpholine 6-9(3) Yellow oil. Yield: 91.4%. NMR (300 MHz, CDCl$_3$): δ 0.87 (t, J=6.6 Hz, 3 H), 1.25-1.29 (m, 10 H), 1.80 (br, 2 H), 2.69 (br, 4 H), 2.73 (br, 4 H), 3.66 (s, 2 H), 4.04 (t, J=6.9 Hz, 2 H), 6.94 (t, J=8.1 Hz, 1H), 7.05 (s, 1H), 7.18-7.26 (m, 1H), 7.35 (d, J=8.1 Hz, 1 H). $^{13}$C NMR (75 MHz, CDCl$_3$) δ 14.0, 22.5, 26.9, 28.0 (2C), 29.1 (2C), 30.1, 31.7, 46.5, 54.3, 54.7 (2C), 104.5, 109.8, 110.4, 128.5, 128.9, 132.7, 155.9, 159.0. ESI-LCMS calculated for (C$_{21}$H$_{32}$FN$_2$S+Na$^+$) 385.20. found 384.90. Elemental analysis: calc./found (C, H): 69.57; 8.62; 69.44; H 8.75.

4-((5-fluoro-1-octyl-1H-indol-3-yl)methyl)morpholine 6-9(4). Yellow oil. Yield: 88.5%. NMR (300 MHz, CDCl$_3$): δ 0.87 (t, J=6.9 Hz, 3 H), 1.24-1.28 (m, 10 H), 1.80 (t, J=6.3 Hz, 2 H), 2.48 (br, 4 H), 3.64 (s, 2 H), 3.69-3.72 (m, 4 H), 4.04 (t, J=7.2 Hz, 2 H), 6.94 (t, J=8.7 Hz, 1 H), 7.07 (s, 1 H), 7.18-7.22 (m, 1H), 7.37 (d, J=9.9 Hz, 1 H). $^{13}$C NMR (75 MHz, CDCl$_3$) δ 14.0, 22.5, 26.9, 29.1 (2C), 30.1, 31.7, 46.5, 53.4, 53.9 (2C), 67.0, 104.5, 109.8, 110.2, 128.5, 128.9, 132.9, 156.0, 159.1. ESI-LCMS calculated for (C$_{21}$H$_{32}$FN$_2$O+H$^+$) 347.25. found 347.10. Elemental analysis: calc./found (C, H): 72.80; 9.02; 73.05; 8.73.

5-fluoro-1-octyl-3-(pyrrolidin-1-ylmethyl)-1H-indole 6-9 (5). Yellow oil. Yield: 67.0%. $^1$H NMR (300 MHz, CDCl$_3$): δ 0.86 (t, J=6.6 Hz, 3 H), 1.24-1.28 (m, 10 H), 1.80 (br, 6 H), 2.62 (br, 4 H), 3.81 (s, 2 H), 4.04 (t, J=6.9 Hz, 2 H), 6.93 (t, J=8.7 Hz, 1 H), 7.17-7.22 (m, 2H), 7.30 (d, J=9.6 Hz, 1 H). $^{13}$C NMR (75 MHz, CDCl$_3$) δ 14.0, 22.5, 23.4 (2C), 26.9, 29.1 (2C), 30.1, 31.7, 46.5, 50.1, 53.8 (2C), 104.1, 109.8, 111.1, 128.3, 128.9, 132.7, 156.0, 159.1. ESI-LCMS calculated for (C$_{21}$H$_{32}$FN$_2$+H$^+$) 331.25. found 331.15. Elemental analysis: calc./found (C, H): 76.32; 9.45; 76.28; 9.23.

5-fluoro-3-((4-methylpiperazin-1-yl)methyl)-1-octyl-1H-indole 6-9(6). Yellow oil. Yield: 56.4%. $^1$H NMR (300 MHz, CDCl$_3$): δ 0.86 (t, J=6.6 Hz, 3 H), 1.24-1.28 (m, 10 H), 1.79 (br, 2 H), 2.27 (br, 4 H), 2.45 (br, 7 H), 3.64 (s, 2 H), 4.03 (t, J=6.9 Hz, 2 H), 6.92 (t, J=8.1 Hz, 1 H), 7.06 (s, 1 H), 7.16-7.20 (m, 1H), 7.36 (d, J=8.4 Hz, 1 H). $^{13}$C NMR (75 MHz, CDCl$_3$) δ 14.0, 22.5, 26.9, 29.1 (2C), 30.1, 31.6, 45.9, 46.4, 52.8 (2C), 53.3, 55.0 (2C), 104.5, 109.8, 110.7, 128.6, 128.8, 132.8, 155.9, 159.0. ESI-LCMS calculated for (C$_{22}$H$_{35}$FN$_3$+H$^+$) 360.28. found 360.20. Elemental analysis: calc./found (C, H): 73.50; 9.53; 73.66; H 9.42.

N-((5-fluoro-1-octyl-1H-indol-3-yl)methyl)-N-methyl-propan-1-amine (6-9(7). Yellow oil. Yield: 78.9%. NMR (300 MHz, CDCl$_3$): δ 0.85-0.94 (m, 6 H), 1.25-1.29 (m, 10 H), 1.51-1.64 (m, 2 H), 1.81 (t, J=6.6 Hz, 2 H), 2.21 (s, 3 H), 2.37 (t, J=7.5 Hz, 2 H), 3.62 (s, 2 H), 4.05 (t, J=7.2 Hz, 2 H), 6.90-6.97 (m, 1 H), 7.06 (s, 1H), 7.18-7.22 (m, 1H), 7.33, 7.36 (dd, J=3.2 Hz, 1 H). $^{13}$C NMR (75 MHz, CDCl$_3$) δ 11.9, 14.0, 20.7, 22.5, 26.9, 29.1, 30.2, 31.7, 42.1, 46.5, 52.6, 59.5, 104.2, 104.5, 109.4, 109.7, 111.7, 128.7, 132.9, 155.9, 159.1. Elemental analysis: calc./found (C, H): 75.86; 10.00; 76.14; 9.52.

N-ethyl-N-((5-fluoro-1-octyl-1H-indol-3-yl)methyl)pro-pan-1-amine (6-9 (8)). Yellow oil. Yield: 70.7%. NMR (300 MHz, CDCl$_3$)): δ 0.85-0.91 (m, 6 H), 1.07 (t, J=7.2 Hz, 3 H), 1.25-1.29 (m, 10 H), 1.48-1.61 (m, 2 H), 1.81 (t, J=6.9 Hz, 2 H), 2.42 (t, J=7.2 Hz, 2 H), 2.53 (q, J=7.2 Hz, 2 H), 3.71 (s, 2 H), 4.05 (t, J=7.2 Hz, 2 H), 6.98-6.96 (m, 1 H), 7.05 (s, 1H), 7.17-7.22 (m, 1H), 7.34, 7.37 (dd, J=2.4 Hz, 1 H). $^{13}$C NMR (75 MHz, CDCl$_3$) δ 11.8, 12.0, 14.0, 20.3, 22.6, 26.9, 29.1, 30.2, 31.7, 46.4, 47.1, 48.6, 55.2, 104.4, 104.7, 109.4, 109.7, 112.1, 128.7, 132.9, 155.9, 158.9. Elemental analysis: calc./found (C, H): 76.25; 10.18; 76.55; 10.08.

N-butyl-N-((5-fluoro-1-octyl-1H-indol-3-yl)methyl)bu-tan-1-amine [6-9-(9)]. Yellow oil. Yield: 74.8%. $^1$H NMR (300 MHz, CDCl$_3$): δ 0.86-0.91 (m, 9 H), 1.26-1.36 (m, 14 H), 1.41-1.61 (m, 4 H), 1.80 (t, J=6.9 Hz, 2 H), 2.43 (t, J=7.2 Hz, 4 H), 3.69 (s, 2 H), 4.05 (t, J=7.2 Hz, 2 H), 6.89-6.96 (m, 1 H), 7.04 (s, 1H), 7.17-7.21 (m, 1H), 7.34, 7.37 (dd, J=2.4 Hz, 1 H). $^{13}$C NMR (75 MHz, CDCl$_3$) δ 14.03, 14.06, 20.7, 22.6, 26.9, 29.1, 29.2, 29.3, 30.2, 31.7, 46.4, 49.3, 53.4, 104.4, 104.7, 109.3, 109.7, 112.3, 128.6, 132.9, 155.9, 158.9. Elemental analysis: calc./found (C, H): 77.27; 10.63; 78.09; 10.40.

Example 9

Evaluation of Antiproliferative Activity of 6-9, 6-9(1) to 6-9(6) in MDA-MB-231 Cells by the MTS Colorimetric Assay Cell Culture and Proliferation Assays. The MDA-MB-231 human breast cells were maintained at 37° C. with 5% CO$_2$ in DMEM (Sigma) supplemented with 10% fetal bovine serum (FBS, Hyclone), 50 U/ml penicillin (Gibco), and 50 μg/ml streptomycin (Gibco). For proliferation assays, cells were seeded at 20% confluency in DMEM containing 5% FBS in 96-well plates for 24 h prior to treatment with specific agents (e.g. cysmethynil) or vehicle at various concentrations for 72 h. The relative number of the live cells was determined using the CellTiter® 96 AQueous One Solution Cell Proliferation Assay (Promega). Each condition was performed in triplicate, and data presented to date were obtained from one determination. IC$_{50}$ values were obtained using GraphPad Prism 4.0 and are given in Table 8. The results showed that 6-9(2), 6-9 (5) were comparable in terms of IC$_{50}$ to 6-9.

TABLE 8

| IC$_{50}$ values of 6-9 and its analogs 6-9(1) to 6-9(6) | | |
|---|---|---|
| Entry | *—NRR | IC$_{50}$ (μM) |
| 6-9(1) | *—N(CH$_3$)$_2$ | 4.9 |
| 6-9 | *—N(piperidine-like, 6-mem) | 2.0 [a] |
| 6-9(2) | *—N piperidine | 2.3 |
| 6-9(3) | *—N thiomorpholine (S) | ND [b] |
| 6-9(4) | *—N morpholine (O) | 3.2 |
| 6-9(5) | *—N pyrrolidine | 2.2 |
| 6-9(6) | *—N piperazine (N-methyl) | ND [b] |

[a] Obtained with re-synthesized 6-9. A determination of an earlier sample of 6-9 gave IC50 of 2.7 μM. IC$_{50}$ values of cysmethynil were concurrently determined and found to be 13.1 μM and 31.5 μM (2 separate determinations).
[b] Not determined because initial screen at a fixed concentration of 10 μM showed approximately 45% inhibition which was low compared to the levels observed with the other compounds.

Example 10

Plasma Protein Binding of Cysmethynil, N-ethyl-N-((1-octyl-5-m-tolyl-1H-indol-3-yl)methyl)ethanamine (J17G) and N-ethyl-N-((1-(3-methylbut-2-enyl)-5-m-tolyl-1H-indol-3-yl)methyl)ethanamine (J38G)

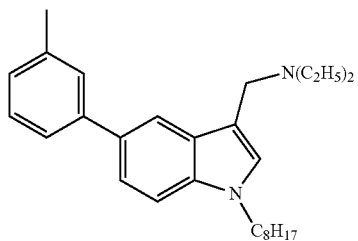

J17G

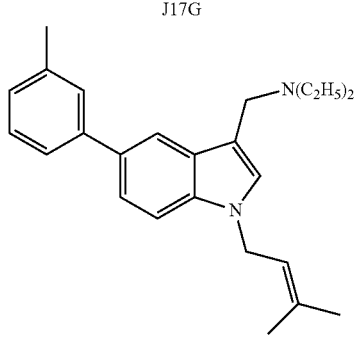

J38G

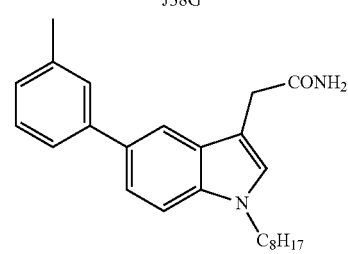

cysmethynil

Figure 9:
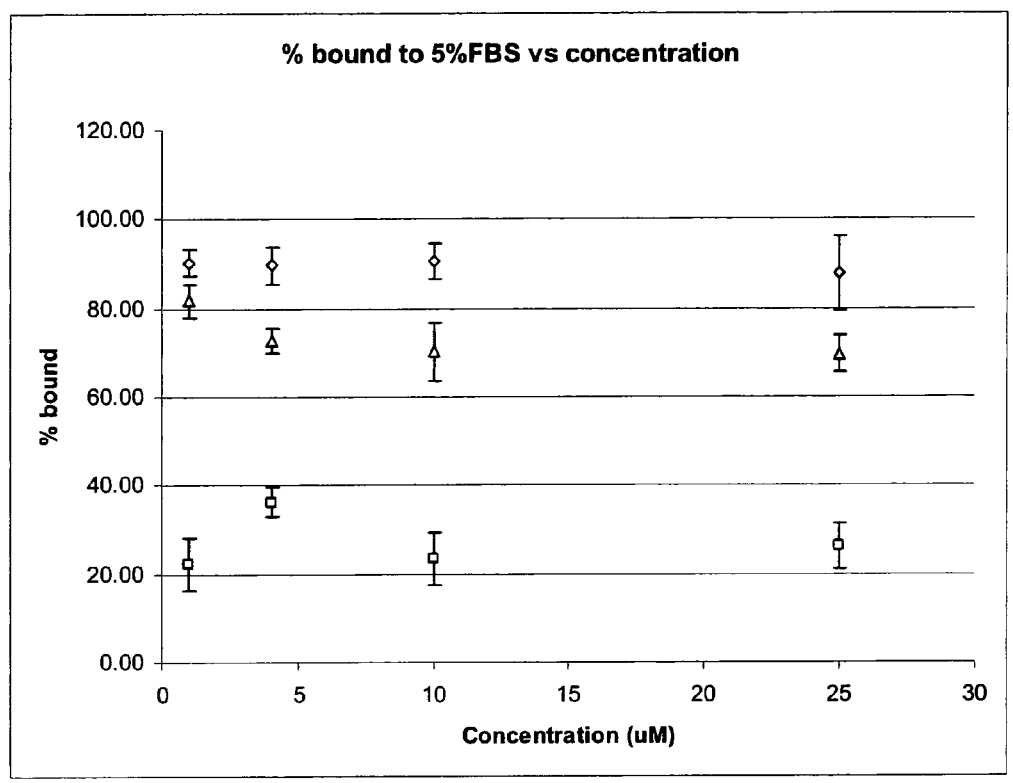
FIG. 9 shows the binding capacities (%) of cysmethynil (◇), compounds (J17G) 4-3 (∆) and (J38G) 6-4 (□) to fetal bovine serum (FBS) using 4 different concentrations (1, 4, 10 and 25 μM) of each respective compound.

The binding capacities of cysmethynil, N-ethyl-N-((1-octyl-5-m-tolyl-1H-indol-3-yl)methyl)ethanamine and N-ethyl-N-((1-(3-methylbut-2-enyl)-5-m-tolyl-1H-indol-3-yl)methyl)ethanamine to fetal bovine serum were determined by an ultracentrifugation method (see Fung E N, Chen Y H, Lau Y Y. Semi-automatic high-throughput determination of plasma protein binding using a 96-well plate filtrate assembly and fast liquid chromatography—tandem mass spectrometry. J Chromatogr B 795 (2003) 187-194) using 4 different concentrations (1, 4, and 25 μM) of each compound. Stock solutions were prepared in DMSO at 100× higher concentrations. A 5% w/v solution of fetal bovine serum in phosphate buffered saline was prepared. An aliquot (10 μL of the stock solution was added to 990 μL of the PBS solution containing 5% fetal bovine serum in a glass tube which was then incubated in a shaking water bath at 37° C. for 30 min. 500 μL of the solution was then transferred to a centrifugal filter device (Amicon Ultra 0.5 ml # UFC503096) and centrifuged at 14 000g, 15 min. After this time, the filter units were removed and placed (upside down) in a collecting tube containing 477 μL, of PBS. The latter was centrifuged at 2000g, 2 min to obtain the retentate. An aliquot of the retentate was added to an equal volume of acetonitrile containing the internal standard (3-1,1-octyl-5-m-tolyl-1H-indole) and analyzed by HPLC (Wang, M.; Khoo, Y. M.; Zhou, J.; Casey, P. J.; Lee, H. S. A HPLC method for the quantification of cysmethynil, an inhibitor of isoprenylcysteine carboxyl methyltransferase, in mouse plasma. J. Chromatography B. 2009, 877, 553-557). The percentage of bound cysmethynil, compounds 4-3 and 6-4 to fetal bovine serum (FBS) are illustrated in FIG. 9.

The results are also given in Table 9 below. It can be seen that compounds J17G and J38G have lower binding capacities than cysmethynil.

TABLE 9

| | Conc (uM) | % Bound | | | | |
|---|---|---|---|---|---|---|
| | | Run 1 | Run 2 | Run 3 | Average | SD |
| CYS | 1 | 89.27 | 93.89 | 87.99 | 90.38 | 3.10 |
| | 4 | 94.43 | 87.59 | 86.86 | 89.63 | 4.18 |
| | 10 | 86.45 | 90.57 | 94.62 | 90.55 | 4.08 |
| | 25 | 78.11 | 93.64 | 91.56 | 87.77 | 8.43 |
| | all conc | | | | 89.58 | |
| J38G | 1 | 25.31 | 15.55 | 26.34 | 22.40 | 5.95 |
| | 4 | 38.39 | 32.39 | 37.88 | 36.22 | 3.33 |
| | 10 | 30.27 | 21.66 | 18.52 | 23.48 | 6.08 |
| | 25 | 27.47 | 20.77 | 30.66 | 26.30 | 5.05 |
| | all conc | | | | 27.10 | |
| J17G | 1 | 82.96 | 77.61 | 84.85 | 81.81 | 3.75 |
| | 4 | 72.64 | 69.93 | 75.73 | 72.77 | 2.90 |
| | 10 | 68.32 | 64.74 | 77.38 | 70.15 | 6.52 |
| | 25 | 71.39 | 64.78 | 72.52 | 69.56 | 4.18 |
| | all conc | | | | 73.57 | |

Example 10

Chemical Synthesis of Target Compounds

TABLE 10

| | | | | IC$_{50}$ (μM) | |
|---|---|---|---|---|---|
| | $R_2$ | $R_3$ | $R_1$ | Icmt inhibition [1] | Antiproliferative activity [1] |
| 1-1 [2] | n-octyl | —CH$_2$CONH$_2$ | m-tolyl | 1.5 ± 0.2 | 21.8 ± 0.8 |
| 1-8 | n-octyl | —CH$_2$CONH$_2$ | 5-F | 7.0 ± 3.4 | 70 ± 20 |
| 3-6 | n-octyl | —CH$_2$CON(piperazine)NCH$_3$ | m-tolyl | 1.7 ± 0.4 | 19.7 ± 0.9 |
| 3-7 | n-octyl | —CH$_2$CONHCH$_3$ | m-tolyl | 2.1 ± 0.4 | 4.7 ± 0.3 |
| 5-1 | n-octyl | —CONH$_2$ | m-tolyl | 30 ± 29 | >100 |
| 5-2 or J20 | n-octyl | —CH$_2$CH$_2$CONH$_2$ | m-tolyl | 1.2 ± 0.3 | 20.7 ± 0.8 |
| 6-3 | isoprenyl | H | m-tolyl | >100 | >100 |

TABLE 10-continued

| | R$_2$ | R$_3$ | R$_1$ | IC$_{50}$ (μM) Icmt inhibition [1] | IC$_{50}$ (μM) Antiproliferative activity [1] |
|---|---|---|---|---|---|
| 6-6 | isoprenyl | —CH$_2$N(morpholine) | m-tolyl | 2.0 ± 0.8 | 34 ± 3 |
| 6-8 | isoprenyl | —CH$_2$CONH$_2$ | 5-F | 69 ± 56 | >100 |

[1] Mean of two separate determinations. Standard deviations (±SD) are provided for compounds that had more than two separate determinations.
[2] cysmethynil Synthesis of 1-8 and 6-8

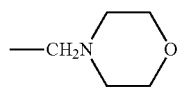

2-(5-Fluoro-1H-indol-3-yl)acetonitrile (A-1). To a solution of 5-fluoro-1H-indole-3-carbaldehyde (4.5 mmol, 1 equiv.) in formamide-methanol (NH$_2$CHO-MeOH; 1:1, v/v; 200 mL) was added sodium borohydride (NaBH$_4$; 13.5 mmol, 3 equiv.) and the mixture was stirred for 0.5 h. To the reaction mixture was added potassium cyanide (KCN; 45 mmol, 10 equiv.) and the whole was refluxed on oil bath at 100° C. for 2.5 h with stirring. After cooling to room temperature, brine was added and the mixture was extracted with chloroform (CHCl$_3$), washed with brine dried over anhydrous sodium sulphate (Na$_2$SO$_4$), and evaporated under reduced pressure to give the nitrile 1. Recrystallization from ethanol (EtOH)/water gave needle-like white crystals. Yield: 52%; $^1$H NMR (300 MHz, CDCl$_3$): δ3.66 (s, 2H), 6.90 (dt, J$_1$=9 Hz, J$_2$=2.1 Hz, 1 H), 7.08 (s, 1 H), 7.13-7.22 (m, 2 H), 8.4 (1H, NH); $^{13}$C NMR (75 MHz, CDCl$_3$) δ 14.2, 102.8, 104.2, 111.0, 112.4, 118.3, 124.8, 126.2, 132.8, 156.3.

2-(5-Fluoro-1H-indol-3-yl)acetamide (A-2). Nitrile A-1 (3.5 mmol, 1 equiv.), was refluxed in tertiary butanol (t-BuOH; 10 mL) containing finely powdered 85% potassium hydroxide (KOH; 28 mmol, 8 equiv.) for 3 h. The reaction mixture was cooled to room temperature, diluted with water, and acidified with 1 M hydrochloric acid (HCl). The resulting suspension was filtered under reduced pressure. The filter cake was washed with water then dried in vacuo. The product was isolated as an off-white/light brown solid. Yield: 61%; $^1$H NMR (300 MHz, CDCl$_3$): δ3.69 (s, 2H), 5.29 (s, 2 H), 6.98 (dt, J$_1$=9 Hz, J$_2$=2.4 Hz, 1 H), 7.21 (s, 1 H), 7.25-7.33 (m, 2 H), 8.34 (s, 1 H).

2-(5-Fluoro-1-(3-methylbut-2-enyl)-1H-indol-3-yl)acetamide (6-8). NaH (60% in mineral oil dispersion, 6 mmol, 1.2 equiv.) was added to a stirred solution of 245-Fluoro-1H-indol-3-yl)acetamide (5 mmol, 1 equiv.) in anhydrous dimethylsulfoxide (DMSO) at room temperature. After 1 h of stirring at the same temperature, 1-chloro-3-methylbut-2-ene was added and the mixture stirred for another 3 h. Distilled water was added to the reaction mixture which was then extracted with CH$_2$Cl$_2$. The organic layer was washed with brine, dried (anhydrous Na$_2$SO$_4$) and evaporated under reduced pressure. The residue was purified by column chromatography with EtOAc/hexane as eluting solvents. Yield: 67%; $^1$H NMR (300 MHz, CDCl$_3$): δ7.26-7.23 (m, 2 H), 7.19 (s, 1 H), 6.98 (t, J=9 Hz, 1 H), 5.72 (br s, 2 H), 5.36 (t, J=6 Hz, 1 H), 4.65 (d, J=6.6 Hz, 2 H), 3.65 (s, 2 H), 1.82 (s, 3 H), (1.79 s, 3 H); $^{13}$C NMR (75 MHz, CDCl$_3$) δ 174.16, 137.04, 133.04, 128.29, 119.27, 110.62, 110.45, 110.27, 107.54, 103.86, 103.55, 44.30, 32.85, 25.63, 18.00. MS (APCI): m/z 261.3 [M+H]$^+$.

2-(5-Fluoro-1-octyl-1H-indol-3-yl)acetamide) (1-8). The reaction between Amide A-2 and bromooctane can be carried out as described by Na, Y. M.; Le Borgne, M.; Pagniez, F.; Le Baut, G.; Le Pape, P. Synthesis and antifungal activity of new 1-halogenobenzyl-3-imidazolylmethylindole derivatives. Eur J Med Chem 2003, 38, 75-87. Yield: 70%; $^1$H NMR (300 MHz, CDCl$_3$): δ7.26-7.18 (m, 2 H), 7.09 (s, 1 H), 6.97 (dt, J$_1$=9 Hz, J$_2$=2.4 Hz, 1 H), 5.73 (br. s, 2 H), 4.06 (t, J=7.2 Hz, 2 H), 3.65 (s, 2 H), 1.83 (t, J=6.3 Hz, 2 H), 1.29-1.25 (m, 10 H), 0.86 (t, J=6.3 Hz, 3H); $^{13}$C NMR (75 MHz, CDCl$_3$) δ 174.10, 159.39, 156.27, 139.66, 133.03, 128.67, 127.68, 127.55, 110.66, 117.23, 103.88, 46.63, 32.81, 31.70, 30.17, 29.09 (2C), 26.94, 22.55, 14.02; MS (APCI): m/z 305.5 [M+H]$^+$ Synthesis of 3-6 and 3-7

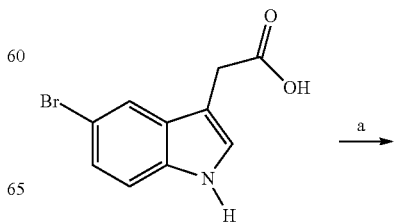

-continued

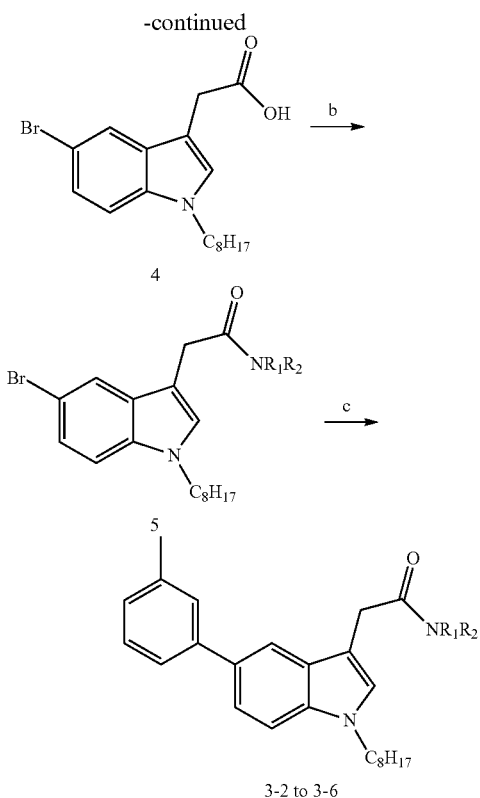

Reagents and conditions:
a C$_8$H$_{17}$Br, NaH, DMF, rt → 53-58° C.
b (i) SOCl$_2$, benzene, reflux, (ii) 2° amine/heterocyclic amine, THF;
c m-tolyl boronic acid Pd(PPh$_3$)$_4$, NaHCO$_3$, EtOH/toluene, reflux.

2-(5-Bromo-1-octyl-1H-indol-3-yl)acetic acid (4). The method of Roy, S.; Eastman, A.; Gribble, G. W. Synthesis of N-alkyl substituted bioactive indolocarbazoles related to G66976 *Tetrahedron* 2006, 62, 7838-45, was followed. To a stirred suspension of NaH (60% dispersion in mineral oil, 138 mmol, 5 equiv.) in tetrahydrofuran (THF; 100 mL) at 0° C. was added a solution of 2-(5-bromo-1H-indol-3-yl)acetic acid (27.7 mmol, 1 equiv.) in THF (50 mL). The mixture was stirred for 30 min at 0° C. after which a solution of 1-bromooctane (83.1 mmol, 3 equiv.) in THF (50 mL) was added dropwise. The mixture was allowed to slowly reach room temperature after which it was stirred for another 4 h. The reaction mixture was cooled to 0° C. and excess NaH was carefully destroyed by the slow addition of MeOH with vigorous stirring, followed by cold water until a clear yellow solution was obtained. Et$_2$O (100 mL) was added, the aqueous phase was separated, acidified with 6 M HCl, and extracted with sufficient CH$_2$Cl$_2$. The combined organic extracts were dried (anhydrous Na$_2$SO$_4$) and concentrated in vacuo. The crude product was purified by column chromatography with hexane/EtOAc. Yield: 64%; $^1$H NMR (300 MHz, CDCl$_3$): δ 7.71 (s, 1 H), 7.26 (d, J=2.1 Hz, 1 H), 7.16 (d, J=8.7 Hz, 1H), 7.07 (s, 1 H), 4.03 (t, J=7.2 Hz, 2 H), 3.73 (s, 2 H), 1.79 (t, J=9.9 Hz), 1.28-1.24 (m, 10 H), 0.86 (t, J=6.3 Hz). $^{13}$C NMR (75 MHz, CDCl$_3$): δ 177.3, 134.8, 129.2, 128.0, 124.5, 121.5, 112.5, 110.9, 105.6, 46.5, 31.7, 30.7, 30.1, 29.1, 29.0, 26.9, 22.5, 14.0.

General Procedure for the Synthesis of 2-(5-bromo-1-octyl-1H-indol-3-yl)-N-substituted acetamides (5). A mixture of 4 (1 mmol, 1 equiv.) and thionyl chloride (SOCl$_2$; 2 mL, 27 equiv.) were refluxed for 4 h in dry benzene (5 mL), after which excess SOCl$_2$ and benzene were removed by distillation in vacuo to give the corresponding acid chloride. The acid chloride was dissolved in dry THF (4 ml) and added dropwise to a stirred solution of the amine (methylamine or N-methylpiperazine) in dry THF at 0-5° C. The reaction mixture was stirred at the same temperature for 1 h after which THF was removed in vacuo and the residue extracted with CH$_2$Cl$_2$ and dried (anhydrous Na$_2$SO$_4$). Removal of the solvent under reduced pressure gave the desired amide which was purified by column chromatography with EtOAc/hexane as eluting solvents. Yields and spectroscopic data of the amides are given below:

2-(5-Bromo-1-octyl-1H-indol-3-yl)-1-(4-methylpiperazin-1-yl)ethanone. Yield: 58%; $^1$H NMR (300 MHz, CDCl$_3$): δ 0.85 (t, J=6.9 Hz, 3 H), 1.23-1.25 (m, 10 H), 1.76 (t, J=6.9 Hz, 2 H), 2.20 (t, J=6.3 Hz, 2 H), 2.23 (s, 3 H), 2.35 (t, J=4.8 Hz, 2 H), 3.46 (t, J=4.8 Hz, 2 H), 3.66 (t, J=4.5 Hz, 2 H), 3.74 (s, 2 H), 4.01 (t, J=7.2 Hz, 2 H), 7.0 (s, 1 H), 7.15 (d, J=8.7 Hz, 1 H), 7.25 (d, J=8.7 Hz, 1 H), 7.70 (s, 1 H); $^{13}$C NMR (75 MHz, CDCl$_3$): δ 14.0, 22.5, 26.8, 29.10, 29.12, 30.7, 31.7, 41.6, 45.9, 46.4, 54.5, 54.9, 107.2, 110.9, 112.3, 121.3, 124.4, 127.2, 129.1, 134.8, 169.6.

2-(5-Bromo-1-octyl-1H-indol-3-yl)-N methylacetamide

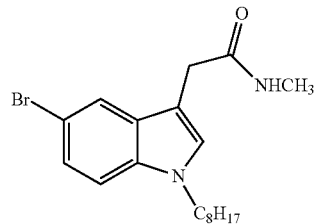

Yield: 73%; $^1$H NMR (300 MHz, CDCl$_3$): δ0.87 (t, J=6.9 Hz, 3 H), 1.26-1.29 (m, 10 H), 1.82 (t, J=6.9 Hz, 2 H), 2.74 (d, J=4.8 Hz, 3 H), 3.66 (s, 2 H), 4.07 (t, J=7.2 Hz, 2 H), 7.04 (s, 1 H), 7.20-7.34 ((m, 2 H), 7.67 (s, 1 H); $^{13}$C NMR (75 MHz, CDCl$_3$) δ 14.0, 22.5, 26.4, 26.9, 29.1, 29.1, 30.1, 31.6, 32.9, 46.5, 107.0, 111.1, 112.8, 121.4, 124.8, 128.4, 129.2, 135.0, 171.7.

1-(4-Methylpiperazin-1-yl)-2-(1-octyl-5-m-tolyl-1H-indol-3-yl)ethanone (3-6). To a solution of the acetamide (1 mmol, 1 equiv.) in 4 ml dimethoxyethane (DME) was added Pd(PPh$_3$)$_4$ (0.05 mmol, 0.05 equiv.) followed by stirring under argon for 15 min. A solution of m-tolylboronic acid (1 mmol, 1 equiv.) in 1.5 ml EtOH was added and stirring was continued for another 15 min. A solution of 2 M aqueous sodium carbonate (Na$_2$CO$_3$; 4 mL) was added and the mixture was refluxed for another 5 h under argon. On cooling, the organic solvent was removed under reduced pressure, the resulting suspension was extracted with CH$_2$Cl$_2$ and dried (anhydrous Na$_2$SO$_4$). The residue obtained on removal of the solvent was purified by column chromatography on silica gel with EtOAc/hexane as eluting solvents. Yield: 45%; $^1$H NMR (300 MHz, CDCl$_3$): δ 7.75 (s, 1 H) 7.46-7.29 (m, 5 H), 7.12 (d, J=6.9 Hz, 1 H), 7.02 (s, 1 H), 4.07 (t, J=6.9 Hz, 2 H), 3.85 (s, 2 H) 3.68 (t, J=6.9 Hz, 2 H), 3.48 (t, J=6.9 Hz, 2 H), 2.43 (s, 3 H), 2.36 (t, J=6.9 Hz, 2 H), 2.23 (s, 3 H), 2.20 (t, J=6.9 Hz, 2 H), 1.81 (t, J=6.9 Hz, 2 H), 1.29-1-25 (m, 10 H), 0.87 (t, J=6.9 Hz, 3 H); $^{13}$C NMR (75 MHz, CDCl$_3$) δ 172.54, 142.54, 138.15, 135.60, 133.07, 132.13, 131.69, 128.41, 127.33, 127.06, 126.24, 124.52, 121.39, 114.06, 109.74, 57.2, 53.3, 53.0, 46.3, 46.0, 31.7, 30.2, 29.2 (2C), 27.0, 22.6, 21.6, 14.1; MS (APCI): m/z 460.5 [M+H]$^+$.

N-Methyl-2-(1-octyl-5-m-tolyl-1H-indol-3-yl)acetamide (3-7). Reaction was carried out as described above. Yield:

68%; ¹H NMR (300 MHz, CDCl₃): δ 7.72 (s, 1 H), 7.49-7.30 (m, 5 H), 7.12 (d, J=6.6 Hz, 1 H), 7.01 (s, 1 H), 5.89 (bs, 1 H), 4.06 (t, J=6.6 Hz, 2 H), 2.68 (d, J=4.5 Hz, 3 H), 2.41 (s, 3 H), 1.82 (t, J=6.8 Hz, 2 H), 1.39-1.25 (m, 10 H), 0.86 (t, J=6.3 Hz, 3 H); ¹³C NMR (75 MHz, CDCl₃) δ 174.10, 159.39, 156.27, 139.66, 133.03, 128.67, 127.68, 127.55, 110.66, 110.47, 110.31, 107.52, 107.46, 103.88, 103.57; MS (APCI): m/z 391.8 [M+H]⁺; Found (calcd. for C₂₆H₃₄N₂O) C, 79.86% (79.96); H, 8.96% (8.77).

Synthesis of 5-1

H), 0.86 (t, J=6.6 Hz, 3 H); ¹³C NMR (75 MHz, CDCl₃): δ 184.8, 143.7, 141.6, 138.9, 135.4, 135.1, 129.1, 128.9, 127.1, 119.3, 119.2, 118.5, 116.8, 111.6, 47.4, 32.7, 31.6, 29.6, 29.0, 26.7, 22.5, 14.0.

1-Octyl-5-m-tolyl-1H-indole-3-carboxylic acid (11). The method of Andreani, A.; Granaiola, M.; Leoni, A.; Locatelli, A.; Morigi, R.; Rambaldi, M.; Roda, A.; Guardigli, M.; Traniello, S.; Spisani, S. N-Benzyl-2-chloroindole-3-carboxylic acids as potential anti-inflammatory agents. Synthesis and screening for effects on human neutrophil functions

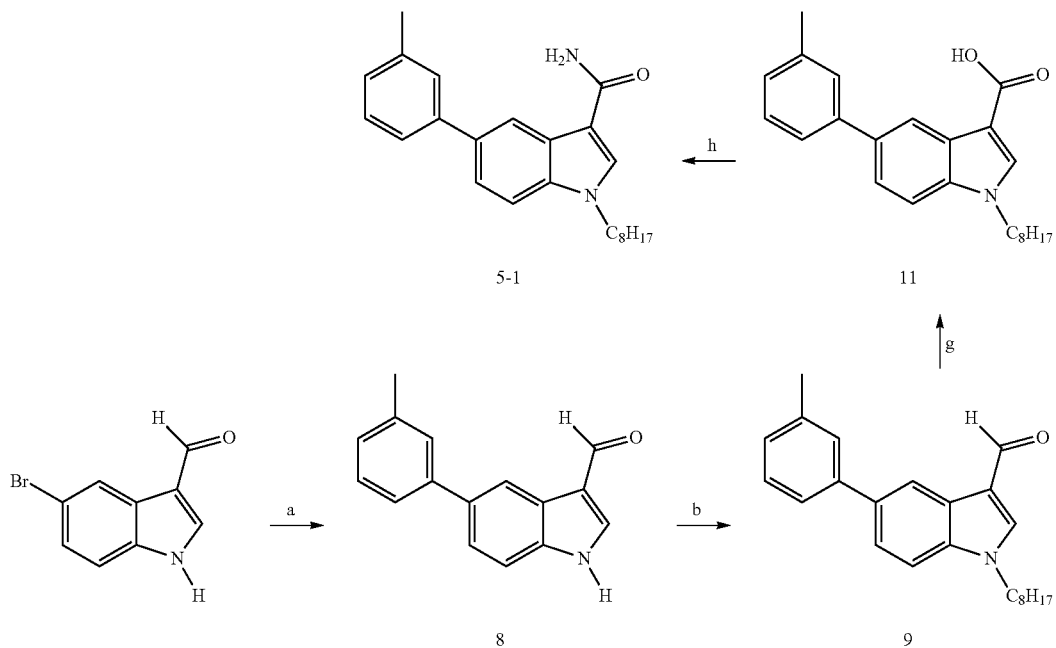

Reagents and condtions:
a m-tolylboronic acid, EtOH/DME, Pd(PPh₃)₄, K₂CO₃;
b C₈H₁₇Br, NaH, DMF;
c NH₂OH•HCl, Py, EtOH;
g KMnO₄, acetone;
h (i) SOCl₂, benzene, reflux, (ii) NH₃ (g), THF.

5-m-Tolyl-1H-indole-3-carbaldehyde (8). 5-Bromo-1H-indole-3-carbaldehye was reacted with m-tolylboronic acid as described for 3-6 and 3-7. Yield: 85%; ¹H NMR (300 MHz, CDCl₃): δ 9.91 (s, 1 H), 8.43 (s, 1 H), 7.66 (s, 1 H), 7.36 (d, J=7.5 Hz, 1 H), 7.20 (d, J=8.7, 1 H), 4.11 (t, J=7.2 Hz, 2 H), 1.85 (t, J=6.3 Hz, 2 H), 1.30-1.24 (m, 10 H), 0.86 (t, J=6 Hz, 3 H); ¹³C NMR (75 MHz, CDCl₃): δ 184.1, 138.7, 135.8, 126.8, 126.8, 124.7, 117.3, 116.4, 111.4, 47.4, 32.7, 31.6, 29.6, 29.0, 26.7, 22.5, 14.0.

1-Octyl-5-m-tolyl-1H-indole-3-carbaldehyde (9). NaH (60% in mineral oil dispersion, 6 mmol, 1.2 equiv.) was added to a stirred solution of aldehyde 8 (5 mmol, 1 equiv.) in anhydrous dimethylsulfoxide (DMSO) at room temperature. After 1 h of stirring at the same temperature, 1-bromooctane was added and the mixture stirred for another 3 h. Distilled water was added to the reaction mixture which was then extracted with CH₂Cl₂. The organic layer was washed with brine, dried (anhydrous Na₂SO₄) and evaporated under reduced pressure. The residue was purified by column chromatography with EtOAc/hexane as eluting solvents as described in Section 5.4.1. Yield: 62%; ¹H NMR (300 MHz, CDCl₃): δ 9.98 (s, 1 H), 8.53 (s, 1 H), 7.66 (s, 1 H), 7.57-7.46 (m, 3 H), 7.39-7.29 (m, 2 H), 7.13 (d, J=7.2H, 1 H), 4.1 (t, J=8.7 Hz, 2 H), 2.42 (s, 3 H), 1.86 (t, J=3 H), 1.29-1.24 (m, 10 H), 0.86 (t, J=6.6 Hz, 3 H); ¹³C NMR (75 MHz, CDCl₃): δ 170.3, 142.3, 141.9, 138.4, 138.2, 136.1, 136.0, 135.8, 128.5, 128.3, 127.4, 124.6, 120.3, 110.3, 106.3, 47.2, 31.7, 31.1, 29.8, 29.1, 22.6, 21.5, 21.5, 14.0.

and on COX1/COX2 activity. *Eur J Med. Chem.* 2004, 39, 785-91, was followed. Compound 9 (0.573 mmol, 1 equiv) was dissolved in 10 mL of acetone and treated with a solution of potassium permanaganate (KMnO₄, 1.5 mmol) in water (5 mL). The reaction mixture was stirred at room temperature for 5 h, treated with 10% H₂O₂ until the pink color of KMnO₄ was not observed and then filtered. The solvent was removed under reduced pressure and the resulting residue was filtered again (if necessary), acidified with 2M HCl and extracted with Et₂O. The organic solvent was removed in vacuo and the residue was purified by column chromatography with hexane/EtOAc as eluting solvents. Yield: 62%; ¹H NMR (300 MHz, CDCl₃): δ 8.84 (s, 1 H), 7.92 (s, 1 H), 7.54-7.48 (m, 2 H), 7.41-7.29 (m, 3 H), 7.14 (d, J=6.6 Hz, 1 H), 4.12 (t, J=6.6 Hz, 2 H), 2.44 (s, 3 H), 1.87 (t, J=6.6 Hz, 3 H), 1.37-1.25 (m, 10 H), 0.86 (t, J=6.6 Hz, 3 H); ¹³C NMR (75 MHz, CDCl₃): δ 170.3, 142.3, 141.9, 138.4, 138.2, 136.1, 136.0, 135.8, 128.5, 128.3, 127.4, 124.6, 120.3, 110.3, 106.3, 47.2, 31.7, 31.1, 29.8, 29.1, 22.6, 21.5, 21.5, 14.0.

1-Octyl-5-m-tolyl-1H-indole-3-carboxamide (5-1). A mixture of 11 (0.4 mmol, 1 equiv.) and SOCl₂ (1 mL, 13 equiv.) in dry benzene (5 mL) were refluxed for 4 h. Excess SOCl₂ and benzene were removed by distillation under reduced pressure and the residue containing the acid chloride was dried in vacuo. It was dissolved in dry THF (4 ml) and ammonia gas was bubbled into the stirred solution for 30 min. THF was removed under vacuum, the residue was extracted with $CH_2Cl_2$, dried (anhydrous $Na_2SO_4$) and the solvent removed under reduced pressure to give carboxamide 5-1. Yield: 74%; $^1H$ NMR (300 MHz, $CDCl_3$): δ 8.16 (s, 1 H), 7.74 (s, 1 H), 7.49-7.13 (m, 6 H), 5.99 (bs, 2 H), 4.09 (t, J=7.2 Hz), 2.42 (s, 3 H); 1.82 (t, J=6.8 Hz, 2 H), 1.28-1.24 (m, 10 H) 0.86 (t, J=6.3 Hz, 3 H); $^{13}C$ NMR (75 MHz, $CDCl_3$) δ 167.32, 141.92, 138.25, 136.07, 135.31, 132.61, 128.58, 128.29, 127.47, 126.18, 124.60, 122.37, 118.94, 110.43, 110.00, 47.02, 31.71, 29.92, 29.11, 29.08, 26.86, 22.57, 21.53, 14.0; MS (APCI): m/z 363.5 $[M+H]^+$.

Synthesis of 5-2 (J20)

tion mixture was brought to room temperature and stirred for 30 min. Excess $LiAlH_4$ was destroyed by careful addition of a saturated aqueous solution of $Na_2SO_4$ with the temperature maintained at about 0° C. The mixture was filtered and the filtrate washed with THF. The combined filtrates were concentrated under reduced pressure, the residue was acidified to pH 6 with 10% HCl and extracted with $CHCl_3$. The combined organic layer was dried (anhydrous $Na_2SO_4$), filtered, evaporated to dryness and purified using flash column chromatography by elution with EtOAc/hexane to give the alcohol 13. Yield: 83%; NMR (300 MHz, $CDCl_3$): δ 2.97 (t, J=18 Hz, 2 H), 3.86-3.93 (m, 2 H), 4.09 (t, J=21 Hz, 1 H), 7.09 (d, J=3 Hz, 1 H), 7.22 (d, J=9 Hz, 1 H), 7.75 (s, 1 H), 8.10 (s, 1 H); MS (APCI): m/z 241.2 $[M+H]^+$.

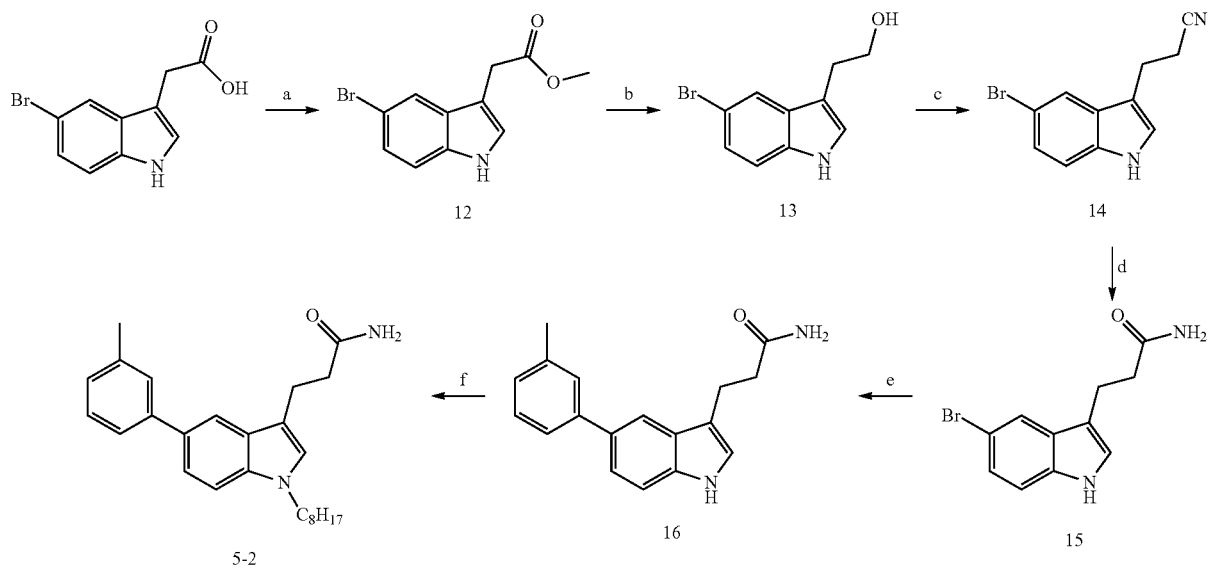

Reagents and conditions:
a MeOH, $H_2SO_4$, reflux (1 h),
b $LiAlH_4$, THF, rt (30 min),
c (i) TEA, MsCl, $CH_2Cl_2$, 0° C. (30 min), (ii) KCN, DMSO, 100° C.
d KOH, t-BuOH, reflux (3 h)
e m-tolylboronic acid, $Pd(PPh_3)_4$, $NaHCO_3$, EtOH/toluene, reflux (1-6 h)
f bromooctane, NaH, DMF, rt (1.5 h) 53-58° C. (3-6 h)

Methyl-2-(5-bromo-1H-indol-3-yl)acetate (12). To a solution of 2-(5-bromo-1H-indol-3-yl)acetic acid (4 mmol) in 20 mL of MeOH was added 10 drops of concentrated sulphuric acid. The mixture was heated under reflux with continuous stirring for a period of 1-1.5 h. Following reflux, the reaction mixture was cooled to room temperature and evaporated in vacuo. The residue was added with a saturated solution of $NaHCO_3$ (50 mL) to neutralize acid, and the resulting alkaline aqueous mixture was extracted with EtOAc and dried over $Na_2SO_4$. Evaporation of the solvent gave a residue which was purified by flash silica gel column chromatography. Elution with $CH_2Cl_2$ yielded the corresponding ester 11 as an off-white solid. Yield: 89%; $^1H$ NMR (300 MHz, $CDCl_3$): δ 3.66 (s, 3 H), 3.68 (s, 2 H), 7.18-7.21 (m, 4 H); MS (APCI), m/z 269.2 $[M+H]^+$.

2-(5-Bromo-1H-indol-3-yl)ethanol (13). The method of Bascop, S. I.; Laronze, J. Y.; Sapi, J. Synthesis of 2-amino-propyle-3-indole-acetic(propionic) acid derivatives. ARKIVOC 2003, 46-61, was followed. To a solution of ester 12 (4 mmol, 1 equiv) in anhydrous THF (50 mL) was added lithium aluminium hydride ($LiAlH_4$; 16 mmol, 4 equiv) in portions with the temperature maintained at 0° C. The reac- 2-(5-Bromo-1H-indol-3-yl)propanenitrile (14). The method of Bascop, S. I.; Laronze, J. Y.; Sapi, J. Synthetis of 2-aminopropyle-3-indole-acetic(propionic) acid derivatives. ARKIVOC 2003, 46-61, was followed. Methane sulphonyl chloride (MsCl, 0.55 mL, 2 equiv) was added to a stirred solution of 13 (3.2 mmol, 1 equiv), triethylamine (0.9 mL, 2 equiv) and anhydrous $CH_2Cl_2$ (20 mL) maintained at 0° C. The reaction mixture was then stirred for 30 min at 0° C. under $N_2$, after which it was treated with 2M NaOH and extracted with $CH_2Cl_2$. The combined organic layer was washed with water, dried (anhydrous $Na_2SO_4$) and evaporated to dryness under reduced pressure. The residue was dissolved in anhydrous DMSO (20 mL), KCN (3.25 mmol, 3 equiv) was added and the reaction mixture was heated at 100° C. in an oil bath for 1 h. It was diluted with a water-ice mixture, extracted with chloroform, the combined organic layer was washed with water, dried (anhydrous $Na_2SO_4$), and evaporated to dryness under reduced pressure. The residue was purified by column chromatography with $CHCl_3$ as eluting solvent and 14 was obtained. Yield: 75%; $^1H$ NMR (300 MHz, DMSO-$d_6$): δ 2.78 (t, J=15 Hz, 2 H), 3.58 (t, J=12 Hz, 2 H), 7.14-7.17 (m, 2 H), 7.20 (d, J=27 Hz, 1 H), 7.68 (s, 1 H), 11.01 (s, 1 H); MS (APCI): m/z 261.3 $[M+H]^+$.

2-(5-Bromo-1H-indol-3-yl)propanamide (15). Amide 15 was prepared from the nitrile 14 by the method described for A-2. Yield: 82%; $^1$H NMR (300 MHz, CDCl$_3$): δ 2.44 (t, J=15 Hz, 2 H), 2.96 (t, J=15 Hz, 2 H), 7.09-7.58 (m, 4 H); MS (APCI): m/z 268.1 [M+H]$^+$.

3-(5-m-Tolyl-1H-indol-3-yl)propanamide (16). Amide 16 was prepared from the 15 by the method described for 3-6 and 3-7. Yield: 50%; $^1$H NMR (300 MHz, CDCl$_3$): δ 2.38 (s, 3 H), 2.49 (t, J=18 Hz, 2 H), 3.02 (t, J=15 Hz, 2 H), 7.12-7.61 (m, 8 H); MS (APCI), m/z 279.4 [M+H]$^+$.

3-(1-Octyl-5-m-tolyl-1H-indol-3-yl)propanamide (5-2). Amide 5-2 was prepared from 16 by the method described for 1-8. Yield: 77%; $^1$H NMR (300 MHz, CDCl$_3$): δ 0.78 (t, J=12 Hz, 3 H), 1.18-1.21 (m, 10 H), 1.69 (t, J=9 Hz, 2 H), 2.35 (s, 3 H), 2.49 (t, J=15 Hz, 2 H), 3.01 (t, J=15 Hz, 2 H), 3.92 (t, J=15 Hz, 2 H), 6.84 (s, 1 H), 7.02 (d, J=9 Hz, 1H), 7.22 (d, J=12 Hz, 2 H), 7.35-7.38 (m, 3 H), 7.68 (s, 1 H); $^{13}$C NMR (75 MHz, CDCl$_3$): δ 14.1, 21.0, 21.6, 22.6, 27.0, 29.2, 29.2, 30.3, 31.8, 36.7, 46.3, 109.7, 113.6, 117.3, 121.4, 124.5, 126.1, 127.1, 128.0, 128.2, 128.6, 132.4, 135.9, 138.2, 142.6, 175.4; MS (APCI), m/z=391.5 [M+H]$^+$.

Synthesis of 6-3 and 6-6

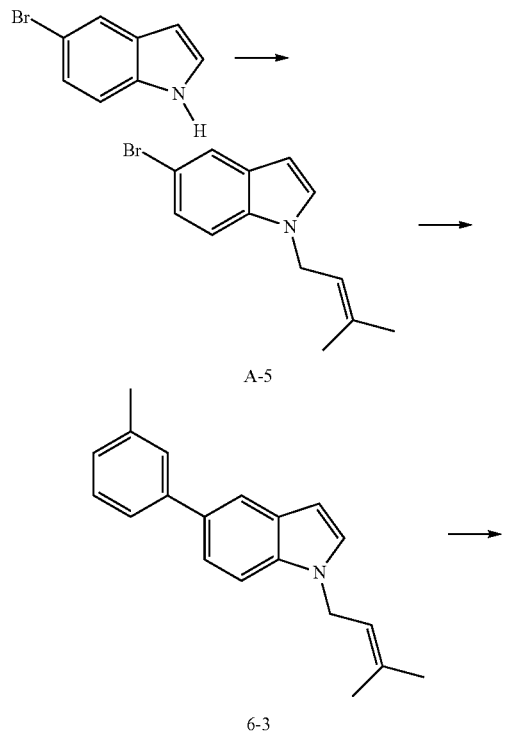

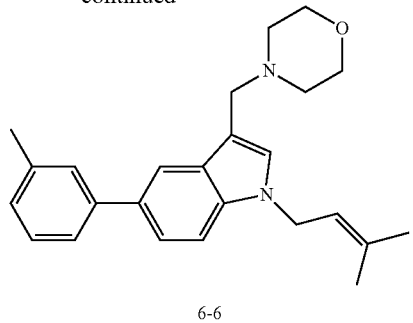

5-Bromo-1-(3-methylbut-2-enyl)-1H-indole (A-5). 5-Bromo-1H-indole was reacted with 1-chloro-3-methylbutene by the method described for 6-8. Yield: 96%; $^1$H NMR (300 MHz, CDCl$_3$): δ7.32 (d, J=1.5 Hz, 1H), 7.23 (d, J=1.5 Hz), 7.23 (d, J=1.5 Hz, 1H), 7.16 (s, 1 H), 7.06 (d, J=3 Hz, 1H), 6.39 (d, J=Hz, 1 H), 5.32 (t, J=6.9 Hz, 1 H), 4.61 (d, J=6.9 Hz, 2 H), 1.78 (s, 3H), 1.74 (s, 3H); $^{13}$C NMR (75 MHz, CDCl$_3$) δ 136.7, 134.6, 130.4, 128.5, 124.1, 123.3, 119.5, 112.5, 110.9, 100.5, 44.3, 25.6, 18.0.

1-(3-Methylbut-2-enyl)-5-m-tolyl-1H-indole (6-3). A-5 was reacted with m-tolylboronic acid as described for 3-6 and 3-7. 6-3 was obtained in 75%; $^1$H NMR (300 MHz, CDCl$_3$): δ7.87 (d, J=0.9 Hz, 1 H), 7.45-7.28 (m, 5 H), 7.11-7.09 (m, 2 H), 6.57 (dd, J$_1$=3.0 Hz, J$_2$=0.6 Hz, 1 H), 5.46-5.43 (m, 1 H), 4.76 (d, J=6.9 Hz, 2 H), 2.47 (s, 3 H), 1.89 (s, 3 H), 1.82 (s, 3 H); $^{13}$C NMR (75 MHz, CDCl$_3$) δ 142.70, 138.14, 136.34, 135.55, 132.98, 129.25, 128.57, 128.26, 128.06, 127.01, 124.54, 121.31, 119.99, 119.47, 109.71, 101.39, 44.30, 25.70, 21.66, 18.08. LC-MS (APCI), m/z=276.5 [M+H]$^+$.

4-((1-(3-methylbut-2-enyl)-5-m-tolyl-1H-indol-3-yl)methyl)morpholine (6-6). Morpholine (1 mmol, 1 equiv.), zinc chloride (ZnCl$_2$; 1.5 mmol, 1.5 equiv.), formaldehyde (HCHO; 1 mmol, 36% aq., 1 equiv.), indole 6-3 (1 mmol, 1 equiv.) and EtOH (3 mL) were stirred together in a round bottom flask for 10 h at room temperature. Distilled water was added to the mixture which was made alkaline by the addition of 4 M sodium hydroxide (NaOH). The mixture was extracted with EtOAc, the solvent was removed under reduced pressure and the residue purified by column chromatography with CH$_2$Cl$_2$/MeOH or EtOAc/hexane as eluting solvents. Yield: 68%; $^1$H NMR (300 MHz, CDCl$_3$): δ 7.76 (s, 1 H), 7.44-7.40 (m, 3 H), 7.34-7.30 (m, 3 H), 7.10 (d, J=7.5 Hz, 1 H), 5.35 (t, J=6.6 Hz, 1 H), 4.67 (J=6.6 Hz, 2 H), 3.93 (s, 2 H), 2.68 (br. s, 2 H), 2.41 (s, 3 H), 1.80 (s, 3 H), 1.74 (s, 3 H), 1.71 (t, J=8.7 Hz, 4 H); $^{13}$C NMR (75 MHz, CDCl$_3$) δ 142.45, 138.22, 136.60, 135.54, 133.33, 129.73, 129.26, 128.58, 128.22, 127.17, 124.53, 121.56, 119.62, 117.27, 110.27, 110.02, 100.61, 53.32, 44.41, 25.66, 24.69, 23.40, 21.59, 18.09. LC-MS (APCI) m/z 375.4 [M+H]$^+$; Found (calcd. for C$_{25}$H$_{30}$N$_2$O): C, 79.92% (80.17); H, 8.10 (8.07).

Purity Determination

| Compound | Mobile Phase A | | | Mobile Phase B | | |
| --- | --- | --- | --- | --- | --- | --- |
| | Composition[a] | RT (min)[c] | Area (%)[d] | Composition[b] | RT (min)[c] | Area (%)[d] |
| 1-8 | A2 | 2.0 | 93.5 | B2 | 2.1 | 93.3 |
| 3-7 | Combustion Analysis[e] | | | Combustion Analysis[e] | | |
| 3-6 | A2 | 3.5 | 92.1 | B2 | 4.0 | 92.8 |
| 5-1 | A5 | 3.6 | 99.0 | B6 | 3.4 | 99 |
| 5-2 | A1 | 6.0 | 97.5 | B1 | 4.1 | 96.9 |

-continued

| Compound | Mobile Phase A | | | Mobile Phase B | | |
|---|---|---|---|---|---|---|
| | Composition[a] | RT (min)[c] | Area (%)[d] | Composition[b] | RT (min)[c] | Area (%)[d] |
| 6-3 | A4 | 3.7 | 96 | B5 | 5.8 | 95.3 |
| 6-6 | Combustion Analysis[e] | | | Combustion Analysis[e] | | |
| 6-8 | A2 | 1.8 | 93.2 | B2 | 2.0 | 93.0 |

[a]Composition of Mobile Phase A: Methanol and Water
A1: 90% methanol
A2: 95% methanol + 0.1% triethylamine (TEA)
A4: 92% methanol + 0.1% TEA
A5: 100% methanol
[b]Composition of Mobile Phase B: Acetonitrile and Water
B1: 90% acetonitrile
B2: 95% acetonitrile + 0.1% triethylamine (TEA)
B5: 92% acetonitrile + 0.1% TEA
B6: 100% acetonitrile
[c]Retention time of Major Peak in chromatogram. Chromatogram was run for at least 15 min for the detection of the major peak
[d]Area (%) of Major Peak = [Area of Major Peak/Total Area of All Peaks] × 100
[e]Combustion analysis for carbon were within 0.4% of calculated values and are stated in the respective compound monographs.

Biological Evaluation

Measurement of ICMT Activity. Icmt activity was determined by following incorporation of $^3$H from [$^3$H]AdoMet (Amersham Biosciences) into the small molecule substrate biotin-S-farnesyl L-cysteine (BFC). Inhibitors were first incubated at 37° C. for 20 min, with the Sf9 membranes containing ICMT. An assay mixture containing 4 µM BFC and 5 µM [$^3$H]AdoMet in 100 mM Hepes, pH 7.4 and 5 mM $MgCl_2$ was added to initiate the reaction. Reactions were carried out at 37° C. for 20 min, and terminated by addition of 10% Tween 20 and streptavidin beads (GE Healthcare, 10 uL of packed beads suspended in 500 µL of 20 mM $NaH_2PO_4$, pH 7.4, containing 150 mM NaCl). The mixtures were mixed by gentle agitation overnight at 4° C. The beads were harvested by centrifugation in a tabletop microcentrifuge at 10,000 rpm for 5 min and washed three times with 500 µL of 20 mM $NaH_2PO_4$, pH 7.4, containing 150 mM NaCl. The beads were then suspended in the same buffer, transferred to scintillation vials, and radioactivity determined.

Cell Culture and Proliferation Assays. The MDA-MB-231 human breast cells were maintained at 37° C. with 5% $CO_2$ in DMEM (Sigma) supplemented with 10% fetal bovine serum (FBS, Hyclone), 50 U/ml penicillin (Gibco), and 50 µg/ml streptomycin (Gibco). For proliferation assays, cells were seeded at 20% confluency in DMEM containing 5% FBS in 96-well plates for 24 h prior to treatment with specific agents (e.g. cysmethynil) or vehicle at various concentrations for 72 h. The relative number of the live cells was determined using the CellTiter® 96 AQueous One Solution Cell Proliferation Assay (Promega). Each condition was performed in triplicate, and data presented represent that obtained from at least two separate experiments.

Example 11

Synthetic Scheme for 5-Fluoro-1-geranyl-1H-indole analogs (6-13)

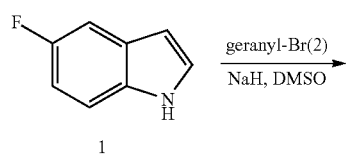

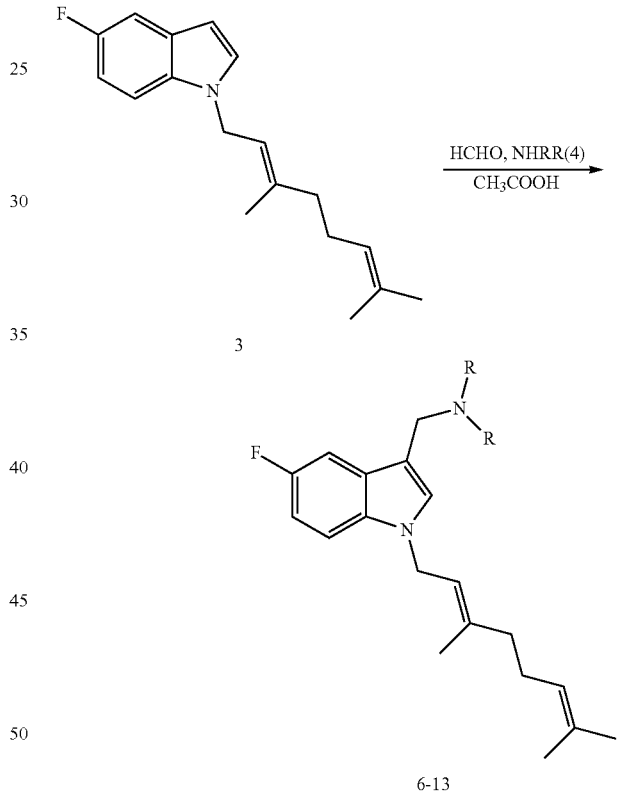

Structures of 5-fluoro-1-geranyl-1H-Indole analogs

| Entry | *—NRR |
|---|---|
| 6-13a | *—N(CH3)2 structure |
| 6-13b | *—N(pyrrolidine) structure |

-continued

| Entry | *—NRR |
|---|---|
| 6-13c | *—N(piperidine) |
| 6-13d | *—N(thiomorpholine, S) |
| 6-13e | *—N(morpholine, O) |
| 6-13f | *—N(pyrrolidine) |
| 6-13g | *—N(piperazine)N— |
| 6-13h | *—N(methyl)(propyl) |
| 6-13i | *—N(ethyl)(propyl) |
| 6-13j | *—N(butyl)(pentyl) |
| 6-13k | *—N(piperazine)N-ethyl |

Experimental Section

Reagents were purchased from Sigma-Aldrich Chemical Company Inc or Alfa Aesar and used without further purification. $^1$H NMR (300 MHz) and $^{13}$C NMR (75 MHz) spectra were measured on a Bruker Spectrospin 300 Ultrashield magnetic resonance spectrometer using CDCl$_3$ as the solvent. Chemical shifts ($\delta$) were reported in ppm and referenced to residual deuterated solvents. Coupling constants (J) were reported in Hz. Reactions were monitored by thin layer chromatography (TLC, Silica Gel 60 F254, Merck) with ultraviolet light as visualizing agent. Column chromatography was carried out with Silica Gel 60 (0.04-0.06 mm).

General Procedure for the Synthesis of (E)-1-(3,7-dimethylocta-2,6-dienyl)-5-fluoro-1H-indole (3)

The general procedure for the synthesis of E)-1-(3,7-dimethylocta-2,6-dienyl)-5-fluoro-1H-indole (3) can be carried out as described in Na, Y. M et al., *Eur. J. Med. Chem.* 2003, 38, 75-87. To the solution of 5-fluore-1H-indole (1, 5 mmol, 1 equiv.) in anhydrous dimethylsulfoxide (DMSO) was added NaH (60% in mineral oil dispersion, 6 mmol, 1.2 equiv.) at room temperature. The mixture was stirred for about 1 h at the same temperature, then geranyl bromide (2, 6 mmol, 1.2 equiv.) was added and the mixture was stirred for 4 h. Water was added to stop the reaction. The mixture was extracted by dichloromethane and the organic layer was washed with brine, dried (Na$_2$SO$_4$), filtered, and evaporated. The residue was purified by column chromatography of silica gel to get off-yellow oil. Yield: 85.0%. $^1$H NMR (300 MHz, CDCl$_3$): $\delta$ 1.62 (s, 3 H), 1.70 (s, 3 H), 1.83 (s, 3 H), 2.05-2.14 (m, 4 H), 4.70 (d, J=6.6 Hz, 2 H), 5.09 (t, J=6.0 Hz, 1 H), 5.40 (t, J=6.6 Hz, 1 H), 6.45 (d, J=2.7 Hz, 1 H), 6.91-7.00 (m, 1H), 7.16 (d, J=3.0 Hz, 1 H), 7.23-7.31 (m, 1H). $^{13}$C NMR (75 MHz, CDCl$_3$) $\delta$ 27.9, 28.9, 35.4, 35.9, 46.6, 50.6, 96.2, 99.9, 100.1, 103.4, 103.7, 111.4, 114.8, 118.9, 121.4, 122.0, 128.1, 141.1, 143.6.

General Procedure for the Synthesis of N-substituted 5-fluoro-1-geranyl-1H-indole methylamine (6-13a to 6-13k)

This procedure can be carried out as described in Brehm, W. J.; Lindwall, H. G. The preparation of Mannich bases related to gramine. *J. Org. Chem.* 1950, 15, 685-687. To the mixture of appropriate secondary amine (4, 1.2 equiv.), 36% aqueous formaldehyde (1.2 equiv.) in acetic acid (5 mL) was added (E)-1-(3,7-dimethylocta-2,6-dienyl)-5-fluoro-1H-indole (3, 200 mg, 1 equiv.) 0° C. The reaction mixture was stirred at room temperature overnight. After the reaction was completed, the reaction mixture was basified by 50% NaOH aqueous solution to pH 9 and extracted with dichloromethane (10 mL×3). The combined extracts were washed with brine (20 mL) and dried over Na$_2$SO$_4$. The organic layer was concentrated under reduced pressure. The crude product was purified by column chromatography of silica gel using or ethyl acetate/hexane or dichloromethane/methanol as eluting solvents.

(E)-1-(1-(3,7-dimethylocta-2,6-dienyl)-5-fluoro-1H-indol-3-yl)-N,N-dimethylmethanamine (6-13a). Yellow oil. Yield: 37.2%. $^1$H NMR (300 MHz, CDCl$_3$): $\delta$ 1.59 (s, 3 H), 1.67 (s, 3 H), 1.80 (s, 3 H), 2.09 (br, 4 H), 2.27 (s, 6 H), 3.56 (s, 2 H), 4.65 (d, J=6.3 Hz, 2 H), 5.07 (br, 1 H), 5.36 (t, J=6.3 Hz, 1 H), 6.90-6.96 (m, 1 H), 7.09 (s, 1H), 7.17-7.22 (m, 1 H), 7.31-7.34 (m, 1H). $^{13}$C NMR (75 MHz, CDCl$_3$) $\delta$ 16.3, 17.7, 25.6, 26.2, 39.4, 44.2, 45.2, 54.4, 104.0, 104.3, 109.5, 109.8, 109.9, 110.1, 111.6, 119.5, 123.6, 128.5, 128.8, 131.8, 132.9, 139.9, 156.1, 159.2.

(E)-N-((1-(3,7-dimethylocta-2,6-dienyl)-5-fluoro-1H-indol-3-yl)methyl)-N-ethylethanamine (6-13b). Yellow oil. Yield: 43.4%. $^1$H NMR (300 MHz, CDCl$_3$): $\delta$ 1.09 (t, J=6.9 Hz, 6 H), 1.59 (s, 3 H), 1.67 (s, 3 H), 1.80 (s, 3 H), 2.09 (br, 4 H), 2.55 (q, J=6.9 Hz, 4 H), 3.72 (s, 2 H), 4.65 (d, J=6.6 Hz, 2 H), 5.07 (br, 1 H), 5.36 (t, J=6.0 Hz, 1 H), 6.90-6.96 (m, 1 H), 7.08 (s, 1H), 7.17-7.21 (m, 1 H), 7.35-7.38 (m, 1H). $^{13}$C NMR (75 MHz, CDCl$_3$) $\delta$ 11.8, 16.4, 17.7, 25.6, 26.2, 39.4, 44.3, 46.5, 48.0, 104.3, 104.6, 109.4, 109.7, 109.9, 110.0, 111.8, 119.7, 123.6, 128.4, 128.9, 131.8, 132.9, 139.8, 156.0, 159.1.

(E)-1-(3,7-dimethylocta-2,6-dienyl)-5-fluoro-3-(piperidin-1-ylmethyl)-1H-indole (6-13c). Yellow oil. Yield: 14.7%. $^1$H NMR (300 MHz, CDCl$_3$): $\delta$ 1.42 (br, 2 H), 1.59 (br, 7 H), 1.66 (s, 3 H), 1.80 (s, 3 H), 2.08 (br, 4 H), 2.45 (br, 4 H), 3.64 (s, 2 H), 4.65 (d, J=6.3 Hz, 2 H), 5.06 (br, 1 H), 5.36 (t, J=6.3 Hz, 1 H), 6.90-6.96 (m, 1 H), 7.11 (s, 1H), 7.17-7.21 (m, 1 H), 7.33-7.36 (m, 1H). $^{13}$C NMR (75 MHz, CDCl$_3$) $\delta$ 16.4, 17.7, 24.3, 25.7, 25.9, 26.2, 39.4, 44.3, 53.9, 54.2, 104.2, 104.5, 109.4, 109.8, 109.9, 110.1, 110.7, 119.6, 123.6, 128.9, 129.1, 129.3, 131.9, 132.8, 156.1, 159.2.

(E)-4-((1-(3,7-dimethylocta-2,6-dienyl)-5-fluoro-1H-indol-3-yl)methyl) thiomorpholine (6-13d). Yellow oil. Yield: 43.2%. $^1$H NMR (300 MHz, CDCl$_3$): $\delta$ 1.59 (s, 3 H), 1.67 (s, 3 H), 1.80 (s, 3 H), 2.09 (br, 4 H), 2.68-2.69 (m, 4 H), 2.73-2.75 (m, 4 H), 3.66 (s, 2 H), 4.65 (d, J=6.6 Hz, 2 H), 5.06 (br, 1 H), 5.36 (t, J=6.6 Hz, 1 H), 6.90-6.97 (m, 1 H), 7.17 (s, 1H), 7.19-7.22 (m, 1 H), 7.34-7.38 (m, 1H). $^{13}$C NMR (75

MHz, CDCl$_3$) δ 16.4, 17.7, 25.7, 26.2, 28.0, 39.4, 44.3, 54.4, 54.7, 104.4, 104.7, 109.6, 109.7, 109.9, 110.0, 110.4, 119.5, 123.6, 128.6, 128.9, 131.9, 133.0, 139.9, 156.1, 159.2.

(E)-4-((1-(3,7-dimethylocta-2,6-dienyl)-5-fluoro-1H-indol-3yl)methyl)morpholine (6-13e). Yellow oil. Yield: 58.6%. $^1$H NMR (300 MHz, CDCl$_3$): δ 1.59 (s, 3 H), 1.67 (s, 3 H), 1.80 (s, 3 H), 2.05-2.13 (m, 4 H), 2.49 (br, 4 H), 3.64 (s, 2 H), 3.70-3.73 (m, 4 H), 4.65 (d, J=6.6 Hz, 2 H), 5.06 (d, J=6.0 Hz, 1 H), 5.36 (t, J=6.0 Hz, 1 H), 6.90-6.97 (m, 1 H), 7.08 (s, 1H), 7.19-7.22 (m, 1 H), 7.36-7.40 (m, 1H). $^{13}$C NMR (75 MHz, CDCl$_3$) δ 16.4, 17.7, 25.7, 26.2, 39.4, 44.3, 53.5, 54.0, 67.0, 104.3, 104.6, 109.6, 109.9, 110.0, 110.2, 110.4, 119.5, 123.6, 128.6, 128.9, 131.9, 133.0, 140.0, 156.1, 159.2.

(E)-1-(3,7-dimethylocta-2,6-dienyl)-5-fluoro-3-(pyrrolidin-1-ylmethyl)-1H-indole (6-13f) Yellow oil. Yield: 45.9%. $^1$H NMR (300 MHz, CDCl$_3$): δ 1.58 (s, 3 H), 1.66 (s, 3 H), 1.79 (br, 7 H), 2.04-2.12 (m, 4 H), 2.59 (br, 4 H), 3.78 (s, 2 H), 4.65 (d, J=6.6 Hz, 2 H), 5.06 (t, J=6.3 Hz, 1 H), 5.36 (t, J=6.6 Hz, 1 H), 6.89-6.96 (m, 1 H), 7.14 (s, 1H), 7.17-7.21 (m, 1 H), 7.31-7.35 (m, 1H). $^{13}$C NMR (75 MHz, CDCl$_3$) δ 11.9, 16.4, 17.7, 25.6, 26.3, 39.4, 44.3, 46.5, 48.0, 104.3, 104.6, 109.4, 109.7, 109.9, 110.0, 111.8, 119.7, 123.6, 128.4, 128.9, 131.9, 132.9, 139.8, 156.0, 159.2.

(E)-1-(3,7-dimethylocta-2,6-dienyl)-5-fluoro-34(4-methylpiperazin-1-yl)methyl)-1H-indole (6-13g). Yellow oil. Yield: 17.7%. $^1$H NMR (300 MHz, CDCl$_3$): δ 1.58 (s, 3 H), 1.66 (s, 3 H), 1.79 (s, 3 H), 2.08-2.10 (m, 4 H), 2.28 (s, 3 H), 2.45 (br, 8 H), 3.64 (s, 2 H), 4.63 (d, J=6.3 Hz, 2 H), 5.06 (d, J=6.3 Hz, 1 H), 5.35 (t, J=6.3 Hz, 1 H), 6.89-6.96 (m, 1 H), 7.07 (s, 1H), 7.16-7.20 (m, 1 H), 7.34-7.38 (m, 1H). $^{13}$C NMR (75 MHz, CDCl$_3$) δ 16.4, 17.7, 25.7, 26.2, 39.4, 44.3, 45.9, 52.9, 53.4, 55.1, 104.3, 104.7, 109.5, 109.8, 109.9, 110.1, 110.7, 110.8, 119.6, 123.6, 128.6, 128.9, 131.9, 132.9, 139.9, 156.1, 159.2.

(E)-N-((1-(3,7-dimethylocta-2,6-dienyl)-5-fluoro-1H-indol-3-yl)methyl)-N-methylpropan-1-amine (6-13h). Yellow oil. Yield: 66.6%. $^1$H NMR (300 MHz, CDCl$_3$): δ 0.92 (t, J=7.5 Hz, 3 H), 1.51-1.70 (m, 5 H), 1.72 (s, 3 H), 1.80 (s, 3 H), 2.05-2.14 (m, 4 H), 2.21 (s, 3 H), 2.37 (t, J=7.5 Hz, 2 H), 3.62 (s, 2 H), 4.65 (d, J=6.6 Hz, 2 H), 5.05 (br, 1 H), 5.36 (t, J=6.6 Hz, 1 H), 6.90-7.00 (m, 1 H), 7.11 (s, 1H), 7.17-7.21 (m, 1 H), 7.32-7.36 (m, 1H). $^{13}$C NMR (75 MHz, CDCl$_3$) δ 11.9, 16.4, 17.7, 20.7, 25.7, 26.2, 39.4, 42.1, 44.2, 52.7, 59.5, 104.2, 104.5, 109.4, 109.7, 109.9, 110.0, 111.8, 119.6, 123.6, 128.4, 128.9, 131.9, 132.9, 139.8, 156.0, 159.2.

N-ethyl-N-((5-fluoro-1-octyl-1H-indol-3-yl)methyl)propan-1-amine (6-13i). Yellow oil. Yield: 61.5%. NMR (300 MHz, CDCl$_3$): δ 0.88 (t, J=7.5 Hz, 3 H), 1.07 (t, J=7.2 Hz, 3 H), 1.48-1.80 (m, 11 H), 2.05-2.11 (m, 4 H), 2.42 (t, J=7.2 Hz, 2 H), 2.53 (q, J=7.2 Hz, 2 H), 3.71 (s, 2 H), 4.65 (d, J=6.6 Hz, 2 H), 5.06 (br, 1 H), 5.36 (t, J=6.6 Hz, 1 H), 6.89-6.96 (m, 1 H), 7.06 (s, 1H), 7.16-7.21 (m, 1 H), 7.35-7.39 (m, 1H). $^{13}$C NMR (75 MHz, CDCl$_3$) δ 11.8, 12.0, 16.4, 17.7, 20.2, 25.7, 26.2, 39.4, 44.2, 47.1, 48.7, 55.1, 104.4, 104.7, 109.4, 109.7, 109.8, 110.0, 112.1, 119.7, 123.7, 128.2, 128.9, 131.9, 132.9, 139.7, 156.0, 159.1. Elemental analysis: calc./found (C, H): 77.79; 9.52; 78.26; 9.66.

(E)-N-butyl-N-((1-(3,7-dimethylocta-2,6-dienyl)-5-fluoro-1H-indol-3-yl)methyl)butan-1-amine (6-13j). Yellow oil. Yield: 41.8%. NMR (300 MHz, CDCl$_3$): δ 0.88 (t, J=7.2 Hz, 6 H), 1.23-1.35 (m, 4 H), 1.44-1.54 (m, 4 H), 1.67 (s, 3 H), 1.72 (s, 3 H), 1.80 (s, 3 H), 2.05-2.12 (m, 4 H), 2.43 (t, J=7.5 Hz, 4 H), 3.69 (s, 2 H), 4.65 (d, J=6.6 Hz, 2H), 5.07 (br, 1 H), 5.36 (t, J=6.6 Hz, 1 H), 6.89-6.95 (m, 1 H), 7.04 (s, 1H), 7.16-7.20 (m, 1 H), 7.34-7.38 (m, 1H). $^{13}$C NMR (75 MHz, CDCl$_3$) δ 14.1, 16.4, 17.7, 20.7, 25.7, 26.2, 29.2, 39.4, 44.2, 49.4, 53.4, 104.4, 104.7, 109.3, 109.7, 109.8, 110.0, 112.4, 119.7, 123.7, 128.2, 128.9, 131.9, 133.0, 139.8, 156.0, 159.0.

(E)-1-(3,7-dimethylocta-2,6-dienyl)-34(4-ethylpiperazin-1-yl)methyl)-5-fluoro-1H-indole (6-13k). Yellow oil. Yield: 51.9%. $^1$H NMR (300 MHz, CDCl$_3$): δ 1.07 (t, J=6.9 Hz, 3 H), 1.58 (s, 3 H), 1.66 (s, 3 H), 1.79 (s, 3 H), 2.01-2.12 (m, 4 H), 2.37-2.53 (m, 10H), 3.65 (s, 2 H), 4.63 (t, J=6.63 Hz, 2 H), 5.06 (t, J=6.0 Hz, 1 H), 5.35 (t, J=6.6 Hz, 1 H), 6.88-6.95 (m, 1 H), 7.06 (s, 1H), 7.15-7.20 (m, 1 H), 7.34-7.38 (m, 1H). $^{13}$C NMR (75 MHz, CDCl$_3$) δ 11.9, 16.3, 17.7, 25.7, 26.1, 39.4, 44.2, 52.2, 52.8, 52.9, 53.4, 104.3, 104.6, 109.5, 109.8, 109.9, 110.0, 110.7, 110.8, 119.6, 123.6, 128.5, 128.9, 131.8, 132.9, 139.9, 156.0, 159.1.

Synthetic scheme for 5-Tolyl-1-isoprenyl-indole Analogs Related to J38 G

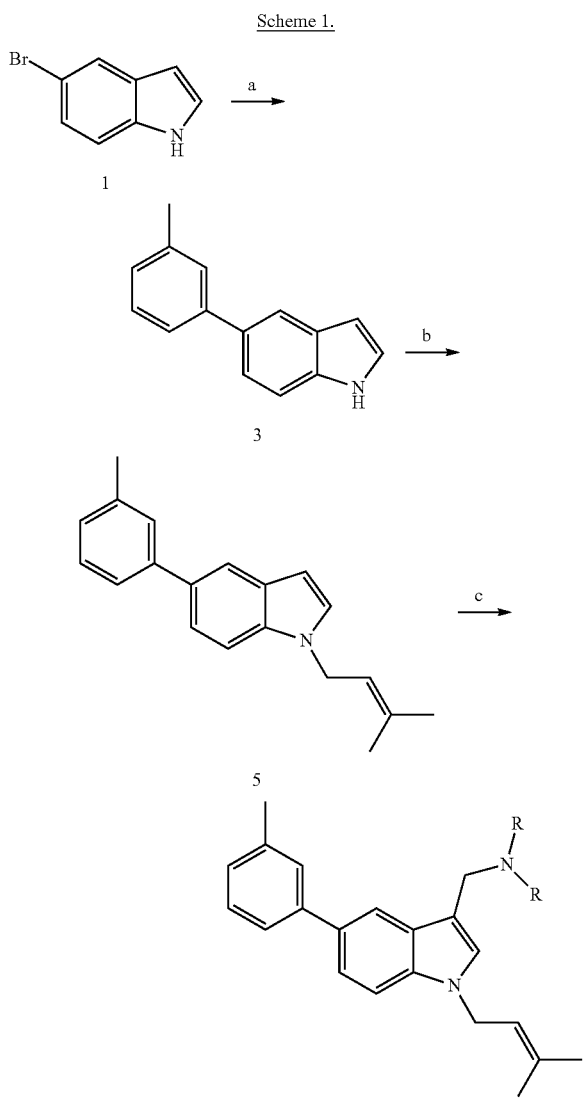

Reagents and conditions:
a 3-tolylboronic acid (2), Pd(dppf)Cl$_2$, K$_2$CO$_3$(aqueous), 1,4-dioxane, microwave, 130, 25 min, twice;
b 1-chloro-3-methylbut-2-ene (4),NaH(60%), DMF, rt, 4 h;
c formadehyde, secondary amine (RRNH), acetic acid, rt, overnight.

Structures of 5-tolyl-1-isoprenyl-1H-Indole Analogs

| Entry | *—NRR |
|---|---|
| 6-14 | *-N(CH₃)₂ |
| 6-15 | *-N(thiomorpholine) |
| 6-16 | *-N(pyrrolidine) |
| 6-17 | *-N(piperazine)N— |
| 6-18 | *-N(methyl)(propyl) |
| 6-19 | *-N(ethyl)(propyl) |
| 6-20 | *-N(propyl)(butyl) |
| 6-21 | *-N(methyl)(butyl) |

Experimental Section

Reagents were purchased from Sigma-Aldrich Chemical Company Inc or Alfa Aesar and used without further purification. $^1$H NMR (300 MHz) and $^{13}$C NMR (75 MHz) spectra were measured on a Bruker Spectrospin 300 Ultrashield magnetic resonance spectrometer using CDCl$_3$ as the solvent. Chemical shifts (δ) were reported in ppm and referenced to residual deuterated solvents. Coupling constants (J) were reported in Hz. Reactions were monitored by thin layer chromatography (TLC, Silica Gel 60 F254, Merck) with ultraviolet light as visualizing agent. Column chromatography was carried out with Silica Gel 60 (0.04-0.06 mm). Mass spectra were recorded in positive ion mode using electro spray ionization (ESI) or high-resolution LC-MS (IT TOF). Nominal mass spectra were captured on an LCQ Finnigan MAT equipped with an atmospheric pressure chemical ionization (APCI) probe and m/z values for the molecular ion were reported. Purity of final compounds was verified by reverse phase HPLC on two different solvent systems (isocratic mode) and found to be ≥95%. Elemental analysis had carbon and hydrogen values that were within ±5% of theoretical values.

General Procedure for the Synthesis of 5-m-tolyl-1H-indole (3)

To the mixture of 5-bromo-1H-indole (1, 5 mmol, 1 equiv.), 3-tolylboronic acid (2, 5.5 mmol, 1.1 equiv.) and Pd(dppf)Cl$_2$ (0.25 mmol, 0.05 equiv.) in 12 mL 1,4-dioxane was added 4 mL aqueous solution of K$_2$CO$_3$ (15 mmol, 3 equiv.). The mixture was stirred under argon for about 15 min then stirred under microwave in 130□ for about 25 min twice. On cooling, the solvent was evaporated and the resulting residue was extracted with CH$_2$Cl$_2$ (20 mL×3), the dichloromethane layer was washed with brine, dried (Na$_2$SO$_4$) and filtered. The residue obtained on removal of the solvent was purified by column chromatography on silica gel with EtOAc/hexane as eluting solvents to give the target compound 5-m-tolyl-1H-indole (3). Yield: 55.0%. $^1$H NMR (300 MHz, CDCl$_3$): δ 2.31 (s, 3 H), 6.47 (s, 1 H), 6.92-7.12 (m, 2 H), 7.18-7.23 (m, 1 H), 7.29-7.35 (m, 4H), 7.74 (s, 1 H), 7.99 (br, 1H). $^{13}$C NMR (75 MHz, CDCl$_3$) δ 21.5, 102.9, 111.1, 119.2, 121.9, 124.4, 124.8, 127.0, 128.2, 128.3, 128.5, 133.4, 135.2, 138.1, 142.5.

General Procedure for the Synthesis of 1-(3-methylbut-2-enyl)-5-m-tolyl-1H-indole (5)

To the solution of 5-m-tolyl-1H-indole (3, 4 mmol, 1 equiv.) in anhydrous dimethylsulfoxide(DMSO) was added NaH (60% in mineral oil dispersion, 4.8 mmol, 1.2 equiv.) at room temperature. The mixture was stirred for about 1 h at the same temperature, then 1-chloro-3-methylbut-2-ene (4, 4.8 mmol, 1.2 equiv.) was added and the mixture was stirred for 4 h. Water was added to stop the reaction. The mixture was extracted by dichloromethane and the organic layer was washed with brine, dried (Na$_2$SO$_4$), filtered, and evaporated. The residue was purified by column chromatography of silica gel to get off-yellow oil. Yield: 87.1%. $^1$H NMR (300 MHz, CDCl$_3$): δ 1.82 (s, 3 H), 1.88 (s, 3 H), 2.48 (s, 3 H), 4.74 (d, J=6.6 Hz, 2 H), 5.45 (t, J=6.9 Hz, 1 H), 6.57 (d, J=2.4 Hz, 1 H), 7.17 (t, J=3.3 Hz, 2 H), 7.34-7.43 (m, 2H), 7.49-7.52 (m, 3H), 7.89 (s, 1H). $^{13}$C NMR (75 MHz, CDCl$_3$) δ 18.0, 21.6, 25.6, 44.2, 101.3, 109.6, 119.4, 119.9, 121.2, 124.4, 126.9, 128.0, 128.2, 128.5, 129.2, 132.9, 135.5, 136.3, 138.1, 142.6.

General Procedure for the Synthesis of N-substituted 1-isoprenyl-5-m-tolyl-1H-indole methylamines (6-14 to 6-21)

To the mixture of appropriate secondary amine (1.2 equiv.), 36% aqueous formaldehyde (1.2 equiv.) in acetic acid (5 mL) was added 1-(3-methylbut-2-enyl)-5-m-tolyl-1H-indole (5, 200 mg, 1 equiv.) 0° C. The reaction mixture was stirred at room temperature overnight. After the reaction was completed, the reaction mixture was basified by 50% NaOH aqueous solution to pH=9 and extracted by dichloromethane (10 mL×3). The combined extracts were washed with brine (20 mL) and dried over Na$_2$SO$_4$. The organic layer was concentrated under reduced pressure. The crude product was purified by column chromatography of silica gel using ethyl acetate/hexane or dichloromethane/methanol as eluting solvents.

N,N-dimethyl-1-(1-(3-methylbut-2-enyl)-5-m-tolyl-1H-indol-3-yl)methanamine (6-14). Yellow oil. Yield: 33.1%. $^1$H NMR (300 MHz, CDCl$_3$): δ 1.79 (s, 3 H), 1.85 (s, 3 H), 2.33 (s, 6 H), 2.45 (s, 3 H), 3.69 (s, 2 H), 4.70 (d, J=6.6 Hz, 2 H), 5.41 (t, J=6.6 Hz, 1 H), 7.11-7.15 (m, 2 H), 7.32-7.38 (m, 2 H), 7.45-7.49 (m, 3H), 7.86 (s, 1H). 13C NMR (75 MHz, CDCl$_3$) δ 18.0, 21.6, 25.6, 44.1, 45.2, 54.2, 109.6, 111.8, 117.7, 119.9, 121.3, 124.6, 126.9, 127.7, 128.2, 128.5, 129.0, 132.8, 135.7, 136.3, 138.1, 142.7.

4-((1-(3-methylbut-2-enyl)-5-m-tolyl-1H-indol-3-yl)methyl)thiomorpholine (6-15). Yellow oil. Yield: 52.9%. $^1$H NMR (300 MHz, CDCl$_3$):δ 1.79 (s, 3 H), 1.85 (s, 3 H), 2.46 (s, 3 H), 2.68-2.71 (m, 4H), 2.80-2.81 (m, 4H), 3.77 (s, 2 H), 4.69 (d, J=6.9 Hz, 2 H), 5.40 (t, J=6.9 Hz, 1 H), 7.08 (s, 1 H), 7.15 (d, J=7.2 Hz, 1 H), 7.32-7.37 (m, 2 H), 7.45-7.47 (m, 3H), 7.89 (s, 1H). $^{13}$C NMR (75 MHz, CDCl$_3$) δ 18.0, 21.6, 25.7, 28.0, 44.2, 54.3, 54.8, 109.7, 110.7, 118.1, 119.9, 121.4, 124.5, 127.0, 127.8, 128.2, 128.5, 129.1, 132.8, 135.8, 136.3, 138.1, 142.7. Elemental analysis: calc./found (C, H): 76.88; 7.74; 75.95; 7.57.

1-(3-methylbut-2-enyl)-3-(pyrrolidin-1-ylmethyl)-5-m-tolyl-1H-indole (6-16). Yellow oil. Yield: 31.1%. $^1$H NMR (300 MHz, CDCl$_3$): δ 1.78-1.81 (m, 7 H), 1.84 (s, 3 H), 2.454 (s, 3 H), 2.63 (br, 4H), 3.88 (s, 2 H), 4.687 (d, J=6.9 Hz, 2 H), 5.40 (t, J=6.9 Hz, 1 H), 7.12-7.17 (m, 2 H), 7.26-7.36 (m, 2 H), 7.44-7.48 (m, 3H), 7.86 (s, 1H). $^{13}$C NMR (75 MHz, CDCl$_3$) δ 18.0, 21.6, 23.5, 25.7, 44.1, 50.2, 54.1, 109.6, 112.3, 117.7, 119.9, 121.2, 124.5, 126.9, 127.4, 128.2, 128.5, 128.9, 132.7, 135.6, 136.2, 138.1, 142.8.

1-(3-methylbut-2-enyl)-34(4-methylpiperazin-1-yl)methyl)-5-m-tolyl-1H-indole (6-17). Yellow oil. Yield: 38.4%. $^1$H NMR (300 MHz, CDCl$_3$): δ 1.78 (s, 3 H), 1.84 (s, 3 H), 2.29 (s, 3 H), 2.45-2.60 (m, 11H), 3.77 (s, 2 H), 4.67 (d, J=6.6 Hz, 2 H), 5.39 (br, 1 H), 7.11-7.15 (m, 2 H), 7.33-7.36 (m, 2H), 7.44-7.47 (m, 3H), 7.89 (s, 1H). $^{13}$C NMR (75 MHz, CDCl$_3$) δ 18.0, 21.6, 25.6, 44.1, 45.9, 52.8, 53.2, 55.0, 109.6, 110.9, 118.0, 119.9, 121.3, 124.5, 127.0, 127.9, 128.2, 128.5, 129.1, 132.7, 135.7, 136.3, 138.1, 142.7.

N-methyl-N-((1-(3-methylbut-2-enyl)-5-m-tolyl-1H-indol-3-yl)methyl)propan-1-amine (6-18). Yellow oil. Yield: 59.2%. $^1$H NMR (300 MHz, CDCl$_3$): δ 0.94 (t, J=7.2 Hz, 3 H), 1.56-1.65 (m, 2 H), 1.78 (s, 3 H), 1.84 (s, 3 H), 2.42 (s, 3 H), 2.45-2.47 (m, 5 H), 3.76 (s, 2 H), 4.69 (d, J=6.6 Hz, 2 H), 5.41 (t, J=5.7 Hz, 1 H), 7.08-7.15 (m, 2 H), 7.32-7.37 (m, 2H), 7.44-7.48 (m, 3H), 7.88 (s, 1H). $^{13}$C NMR (75 MHz, CDCl$_3$) δ 11.9, 18.0, 20.6, 21.6, 25.7, 42.0, 44.1, 52.5, 59.3, 109.6, 111.6, 118.0, 119.9, 121.3, 124.5, 127.0, 117.7, 128.2, 128.5, 129.1, 132.7, 135.7, 136.2, 138.0, 142.7.

N-ethyl-N-((1-(3-methylbut-2-enyl)-5-m-tolyl-1H-indol-3-yl)methyl)propan-1-amine (6-19). Yellow oil. Yield: 36.8%. $^1$H NMR (300 MHz, CDCl$_3$): δ$^1$H NMR (300 MHz, CDCl$_3$): δ 0.93 (t, J=7.2 Hz, 3 H), 1.11 (t, J=7.2 Hz, 3 H), 1.54-1.66 (m, 2 H), 1.79 (s, 3 H), 1.85 (s, 3 H), 2.42 (s, 3 H), 2.46-2.51 (m, 5 H), 2.59 (q, J=7.2 Hz, 2 H), 3.83 (s, 2 H), 4.69 (d, J=6.6 Hz, 2 H), 5.42 (t, J=6.3 Hz, 1 H), 7.08 (s, 1 H), 7.14 (d, J=7.5 Hz, 1 H), 7.32-7.37 (m, 2H), 7.45-7.49 (m, 3H), 7.93 (s, 1H). $^{13}$C NMR (75 MHz, CDCl$_3$) δ 11.9, 12.0, 18.0, 20.3, 21.6, 25.6, 44.1, 47.1, 48.6, 55.2, 109.5, 112.6, 118.2, 120.1, 121.1, 124.5, 126.9, 127.3, 128.2, 128.5, 129.2, 132.5, 135.8, 136.1, 138.1, 142.8.

N-butyl-N-((1-(3-methylbut-2-enyl)-5-m-tolyl-1H-indol-3-yl)methyl)butan-1-amine (6-20). Yellow oil. Yield: 42.1%. $^1$H NMR (300 MHz, CDCl$_3$): δ$^1$H NMR (300 MHz, CDCl$_3$): δ 0.91 (t, J=7.2 Hz, 6 H), 1.28-1.40 (m, 4 H), 1.49-1.59 (m, 4 H), 1.79 (s, 3 H), 1.85 (s, 3 H), 2.45-2.52 (m, 7 H), 3.81 (s, 2 H), 4.69 (d, J=6.6 Hz, 2 H), 5.41 (t, J=6.3 Hz, 1 H), 7.06 (s, 1 H), 7.14 (d, J=7.5 Hz, 1H), 7.32-7.36 (m, 2H), 7.44-7.49 (m, 3H), 7.93 (s, 1H). $^{13}$C NMR (75 MHz, CDCl$_3$) δ 14.1, 18.0, 20.8, 21.6, 25.6, 29.3, 44.1, 49.2, 53.5, 109.4, 112.8, 118.3, 120.1, 121.1, 124.4, 126.8, 127.3, 128.2, 128.5, 129.2, 132.4, 135.8, 136.1, 138.0, 142.8. Elemental analysis: calc./found (C, H): 83.60; 9.68; 83.54; 9.82.

N-((1-(3-methylbut-2-enyl)-5-m-tolyl-1H-indol-3-yl)methyl)-N-propylpropan-1-amine (6-21). Yellow oil. Yield: 57.4%. $^1$H NMR (300 MHz, CDCl$_3$): δ$^1$H NMR (300 MHz, CDCl$_3$): δ 0.91 (t, J=7.2 Hz, 6 H), 1.52-1.64 (m, 4 H), 1.79 (s, 3 H), 1.85 (s, 3 H), 2.44-2.49 (m, 7 H), 3.82 (s, 2 H), 4.69 (d, J=6.6 Hz, 2 H), 5.42 (t, J=6.6 Hz, 1 H), 7.07 (s, 1 H), 7.14 (d, J=7.5 Hz, 1 H), 7.32-7.37 (m, 2H), 7.45-7.49 (m, 3H), 7.94 (s, 1H). $^{13}$C NMR (75 MHz, CDCl$_3$) δ 12.0, 18.0, 20.3, 21.6, 25.6, 44.1, 49.3, 55.8, 109.5, 112.8, 118.3, 120.1, 121.1, 124.4, 126.8, 127.3, 128.2, 128.5, 129.1, 132.4, 135.8, 136.1, 138.1, 142.8.

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

What is claimed is:

1. A compound of Formula I

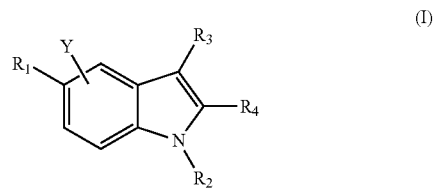

or a pharmaceutically acceptable salt thereof,
wherein
R$_1$ is (CH$_3$)$_m$-aryl, wherein m is 1;
Y is hydrogen;
R$_2$ is C$_{1-20}$alkyl;
R$_3$ is selected from the group consisting of CH$_2$NH$_2$, CH$_2$N(CH$_3$)$_2$, CH$_2$N(C$_2$H$_5$)$_2$, CH$_2$N(C$_3$H$_7$)$_2$,

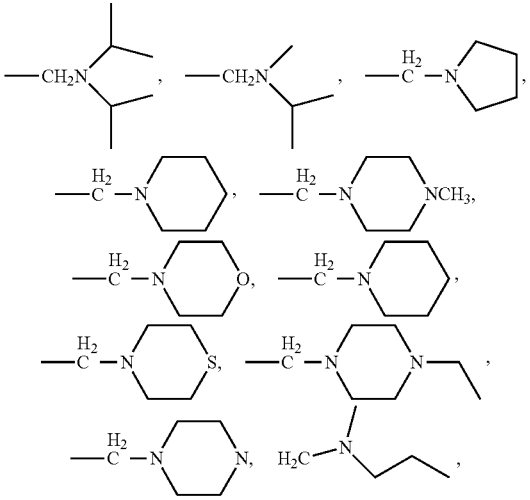

-continued $H_2C-N(C_2H_5)(C_3H_7)$ and $H_2C-N(C_4H_9)_2$; and $R_4$ is hydrogen or $C_1$-$C_4$ alkyl.

2. The compound according to claim 1, wherein $R_2$ is $C_{1-8}$alkyl.

3. The compound according to claim 2, wherein $R_2$ is selected from the group consisting of methyl, ethyl, n-propyl, propyl, isopropyl, butyl, n-butyl, isobutyl, sec-butyl, tert-butyl, tert-amyl, pentyl, hexyl, heptyl, and octyl.

4. The compound according to claim 1, wherein $R_2$ is octyl.

5. The compound according to claim 1, wherein the aryl is phenyl or naphthyl.

6. The compound according to claim 1, wherein $R_1$ is selected from the group consisting of 2'-$CH_3$—$C_6H_5$, 3'-$CH_3$—$C_6H_5$ and 4'-$CH_3$—$C_6H_5$.

7. The compound according to claim 1, wherein the compound is selected from the group consisting of:

1-octyl-5-m-tolyl-1H-indol-3-yl methanamine (J18);
N,N-dimethyl(1-octyl-5-m-tolyl-1H-indol-3-yl) methanamine (J25G);
N-ethyl-N-((1-octyl-5-m-tolyl-1H-indol-3-yl) methyl) ethanamine (J17G);
N-((1-octyl-5-m-tolyl-1H-indol-3-yl) methyl)-N-propyl-propan-1-amine) (J27G);
N-isopropyl-N-((1-octyl-5-m-tolyl-1H-indol-3-yl) methyl) propan-2-amine (J26G);
N-methyl-N-((1-octyl-5-m-tolyl-1H-indol-3-yl) methyl) propan-2-amine (J29G);
1-octyl-3-(pyrrolidin-1-ylmethyl)-5-m-tolyl-1H-indole (J31G);
1-octyl-3-(piperidin-1-ylmethyl)-5-m-tolyl-1H-indole (J32G);
3-((4-methylpiperazin-1-yl) methyl)-1-octyl-5-m-tolyl-1H-indole (J30G);
3-(morpholinomethyl)-1-octyl-5-m-tolyl-1H-indole (J34G);
N-ethyl-N-((1-octyl-5-o-tolyl-1H-indol-3-yl) methyl) ethanamine (J36G); and
N-ethyl-N-((1-octyl-5-p-tolyl-1H-indol-3-yl) methyl) ethanamine (J37G).

8. A method of preparing a compound of formula I, the method comprising:

i) adding a phosphine compound to a solution containing a compound of formula II (II)

[structure of formula II: indole with Z substituent, $R_4$ at 2-position, $R_2$ on N]

wherein Z is a leaving group, under conditions to form a compound of formula III (III)

[structure of formula III: 5-(m-tolyl)indole with $R_4$ at 2-position, $R_2$ on N]

and ii) adding an amine and an aldehyde to the solution obtained in step i) to form a compound of formula I, wherein the compound of Formula I is (I)

[structure of formula I: indole with $R_1$, Y, $R_3$, $R_4$, $R_2$ substituents]

or a pharmaceutically acceptable salt thereof,
wherein
$R_1$ is $(CH_3)_m$-aryl, wherein m is 1;
Y is hydrogen;
$R_2$ is $C_{1-20}$alkyl;
$R_3$ is selected from the group consisting of $CH_2NH_2$, $CH_2N(CH_3)_2$, $CH_2N(C_2H_5)_2$, $CH_2N(C_3H_7)_2$, —$CH_2N(iPr)_2$, —$CH_2N(iPr)_2$, —$CH_2$—N(pyrrolidine), —$CH_2$—N(piperidine), —$CH_2$—N(N-methylpiperazine), —$CH_2$—N(morpholine), —$CH_2$—N(piperidine), —$CH_2$—N(thiomorpholine), —$CH_2$—N(N-ethylpiperazine), —$CH_2$—N(piperazine), $H_2C$—N(Et)(Pr), $H_2C-N(C_2H_5)(C_3H_7)$ and $H_2C-N(C_4H_9)_2$; and $R_4$ is hydrogen or $C_1$-$C_4$ alkyl.

9. A method of preparing a compound of formula I, the method comprising:
   i) adding a sulphonyl compound to a solution containing a compound of formula IV

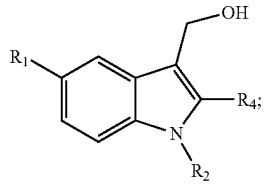

under conditions to form a sulphonate ester compound; and
   ii) adding an amine to the solution containing the sulphonate ester compound under conditions to form a compound of formula I,
wherein the compound of Formula I is

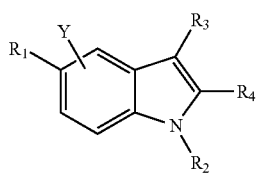

or a pharmaceutically acceptable salt thereof,
wherein
   $R_1$ is $(CH_3)_m$-aryl, wherein m is 1;
   Y is hydrogen;
   $R_2$ is $C_{1-20}$alkyl;
   $R_3$ is selected from the group consisting of $CH_2NH_2$, $CH_2N(CH_3)_2$, $CH_2N(C_2H_5)_2$, $CH_2N(C_3H_7)_2$,

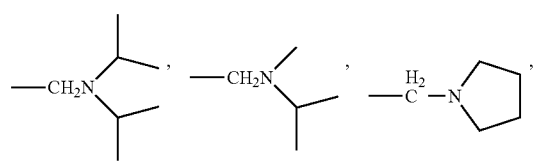

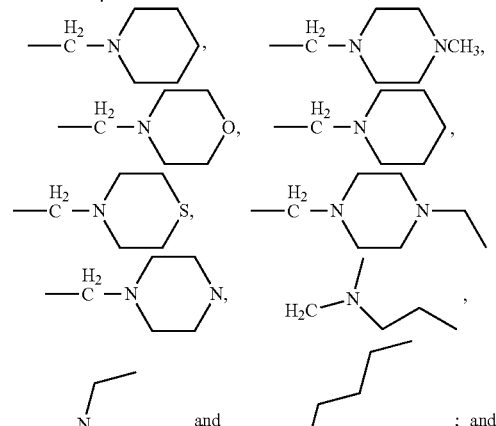

$R_4$ is hydrogen or $C_1$-$C_4$ alkyl.

10. The method according to claim 9, wherein the sulphonyl compound is methanesulphonyl chloride or p-toluenesulfonyl chloride.

11. A method of preparing a compound of formula I, the method comprising:
   i) adding a methylating agent into a solution containing a compound of formula V

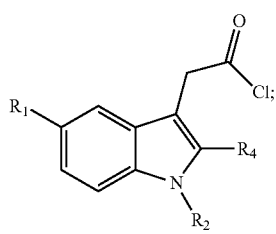

under conditions to form a compound of formula VI

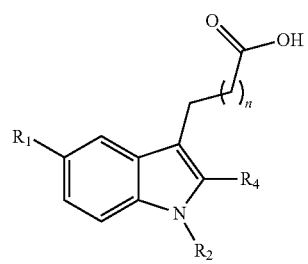

wherein n corresponds to the number of times step i) is repeated;
   ii) adding a sulphonyl compound to the solution containing the compound of formula VI, under conditions to form a sulphonyl ester compound; and
   iii) adding an amine to the solution containing the sulphonyl ester compound to form a compound of formula I,
wherein the compound of Formula I is

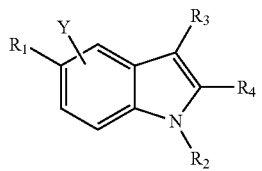

or a pharmaceutically acceptable salt thereof,
wherein
   $R_1$ is $(CH_3)_m$-aryl, wherein m is 1;
   Y is hydrogen;
   $R_2$ is $C_{1-20}$alkyl;
   $R_3$ is selected from the group consisting of $CH_2NH_2$, $CH_2N(CH_3)_2$, $CH_2N(C_2H_5)_2$, $CH_2N(C_3H_7)_2$,

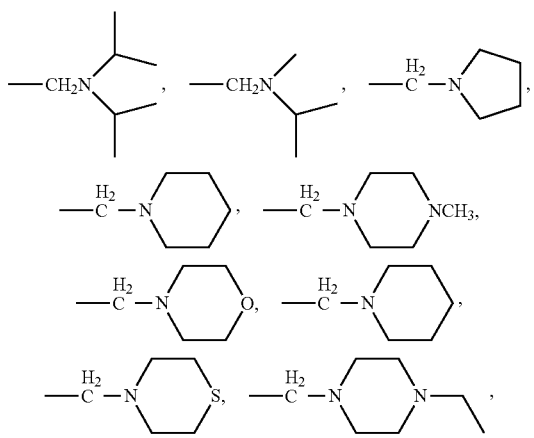
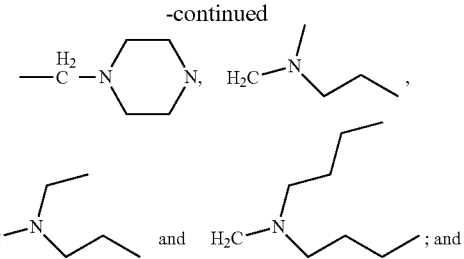
$R_4$ is hydrogen or $C_1$-$C_4$ alkyl.
12. The method according to claim 11, wherein the methylating agent is diazomethane.
13. The method according to claim 11, wherein the sulphonyl compound is methanesulphonyl chloride or p-toluenesulfonyl chloride.
* * * * *